(12) United States Patent
Malecha et al.

(10) Patent No.: US 9,903,830 B2
(45) Date of Patent: Feb. 27, 2018

(54) ACCURATE ANALYTE MEASUREMENTS FOR ELECTROCHEMICAL TEST STRIP BASED ON SENSED PHYSICAL CHARACTERISTIC(S) OF THE SAMPLE CONTAINING THE ANALYTE

(71) Applicant: LifeScan Scotland Limited, Inverness (GB)

(72) Inventors: Michael Malecha, Muir of Ord (GB); Antony Smith, Inverness-shire (GB); David McColl, Inverness-shire (GB)

(73) Assignee: LifeScan Scotland Limited, Inverness (GB)

( * ) Notice: Subject to any disclaimer, the term of this patent is extended or adjusted under 35 U.S.C. 154(b) by 460 days.

(21) Appl. No.: 14/353,870

(22) PCT Filed: Dec. 18, 2012

(86) PCT No.: PCT/GB2012/053276
§ 371 (c)(1),
(2) Date: Apr. 24, 2014

(87) PCT Pub. No.: WO2013/098563
PCT Pub. Date: Jul. 4, 2013

(65) Prior Publication Data
US 2014/0332408 A1    Nov. 13, 2014

Related U.S. Application Data

(60) Provisional application No. 61/581,087, filed on Dec. 29, 2011, provisional application No. 61/581,089, (Continued)

(51) Int. Cl.
*G01N 27/327* (2006.01)
*G01N 27/26* (2006.01)
*G06F 19/24* (2011.01)

(52) U.S. Cl.
CPC ......... *G01N 27/3274* (2013.01); *G01N 27/26* (2013.01); *G01N 27/3272* (2013.01); *G06F 19/24* (2013.01)

(58) Field of Classification Search
CPC .................................................. G01N 27/3274
See application file for complete search history.

(56) References Cited

U.S. PATENT DOCUMENTS

| | | |
|---|---|---|
| 4,919,770 A | 4/1990 | Preidel et al. |
| 5,429,735 A | 7/1995 | Johnson et al. |

(Continued)

FOREIGN PATENT DOCUMENTS

| | | |
|---|---|---|
| CN | 1558235 A | 12/2004 |
| CN | 1914511 A | 2/2007 |

(Continued)

OTHER PUBLICATIONS

First Office Action issued in related Chinese Patent Application No. 201280070979.9, dated Sep. 6, 2015, 29 pages.
(Continued)

*Primary Examiner* — Jill Warden
*Assistant Examiner* — Matthew Krcha

(57) ABSTRACT

Various embodiments for methods and systems that allow for a more accurate analyte concentration with a biosensor by determining at least one physical characteristic of the sample containing the analyte and deriving one of a batch slope, sampling time, or combinations thereof to attain accurate glucose concentration.

15 Claims, 40 Drawing Sheets

Related U.S. Application Data filed on Dec. 29, 2011, provisional application No. 61/581,099, filed on Dec. 29, 2011, provisional application No. 61/581,100, filed on Dec. 29, 2011, provisional application No. 61/654,013, filed on May 31, 2012.

(56) References Cited

U.S. PATENT DOCUMENTS

| | | | |
|---|---|---|---|
| 5,708,247 A | 1/1998 | McAleer et al. | |
| 5,792,668 A | 8/1998 | Fuller et al. | |
| 5,951,836 A | 9/1999 | McAleer et al. | |
| 6,179,979 B1 | 1/2001 | Hodges et al. | |
| 6,193,873 B1 | 2/2001 | Ohara et al. | |
| 6,241,862 B1 | 6/2001 | McAleer et al. | |
| 6,284,125 B1 | 9/2001 | Hodges et al. | |
| 6,287,451 B1 | 9/2001 | Winarta et al. | |
| 6,304,767 B1 | 10/2001 | Soller et al. | |
| 6,391,645 B1 | 5/2002 | Huang et al. | |
| 6,413,410 B1 | 7/2002 | Hodges et al. | |
| 6,475,372 B1 | 11/2002 | Ohara et al. | |
| 6,517,482 B1 | 2/2003 | Elden et al. | |
| 6,576,117 B1 | 6/2003 | Iketaki et al. | |
| 6,645,368 B1 | 11/2003 | Beaty et al. | |
| 6,685,633 B2 | 2/2004 | Albert et al. | |
| 6,716,577 B1 | 4/2004 | Yu et al. | |
| 6,733,655 B1 | 5/2004 | Davies et al. | |
| 6,749,887 B1 | 6/2004 | Dick et al. | |
| 6,841,389 B2 | 1/2005 | Novikov et al. | |
| 6,863,801 B2 | 3/2005 | Hodges et al. | |
| 6,890,421 B2 | 5/2005 | Ohara et al. | |
| 7,018,843 B2 | 3/2006 | Heller | |
| 7,045,046 B2 | 5/2006 | Chambers et al. | |
| 7,050,847 B2 | 5/2006 | Ollmar et al. | |
| 7,258,769 B2 | 8/2007 | Cui et al. | |
| 7,291,256 B2 | 11/2007 | Teodorczyk et al. | |
| 7,338,639 B2 | 3/2008 | Burke et al. | |
| 7,390,667 B2 | 6/2008 | Burke et al. | |
| 7,407,811 B2 | 8/2008 | Burke et al. | |
| 7,452,457 B2 | 11/2008 | Burke et al. | |
| 7,488,601 B2 | 2/2009 | Burke et al. | |
| 7,494,816 B2 | 2/2009 | Burke et al. | |
| 7,498,132 B2 | 3/2009 | Yu et al. | |
| 7,597,793 B2 | 10/2009 | Burke et al. | |
| 7,601,249 B2 | 10/2009 | Iyengar et al. | |
| 7,604,721 B2 | 10/2009 | Groll et al. | |
| 7,645,373 B2 | 1/2010 | Groll et al. | |
| 7,645,421 B2 | 1/2010 | Groll | |
| 7,678,250 B2 | 3/2010 | Bell et al. | |
| 7,718,439 B2 | 5/2010 | Groll | |
| 7,727,467 B2 | 6/2010 | Burke et al. | |
| 7,749,437 B2 | 7/2010 | Mosoiu et al. | |
| 7,829,023 B2 | 11/2010 | Burke et al. | |
| 7,879,618 B2 | 2/2011 | Mosoiu et al. | |
| 7,892,849 B2 | 2/2011 | Burke et al. | |
| 7,923,258 B2 | 4/2011 | Heller | |
| 7,927,882 B2 | 4/2011 | Heller | |
| 7,955,492 B2 | 6/2011 | Fujiwara et al. | |
| 7,964,089 B2 | 6/2011 | Harding et al. | |
| 7,972,851 B2 | 7/2011 | Wang et al. | |
| 7,972,861 B2 | 7/2011 | Deng et al. | |
| 8,080,153 B2 | 12/2011 | Feldman et al. | |
| 8,083,925 B2 | 12/2011 | Feldman et al. | |
| 8,088,271 B2 | 1/2012 | Fujiwara et al. | |
| 2003/0106809 A1* | 6/2003 | Kermani | G01N 27/3273 205/775 |
| 2004/0079652 A1 | 4/2004 | Vreeke et al. | |
| 2004/0157275 A1 | 8/2004 | Marfurt | |
| 2004/0157338 A1* | 8/2004 | Burke | G01N 27/3274 436/147 |
| 2004/0157339 A1 | 8/2004 | Burke et al. | |
| 2005/0176133 A1 | 8/2005 | Miyashita et al. | |
| 2007/0084734 A1 | 4/2007 | Roberts et al. | |
| 2007/0087397 A1 | 4/2007 | Kraft et al. | |
| 2007/0138026 A1 | 6/2007 | Fujiwara et al. | |
| 2007/0227912 A1 | 10/2007 | Chatelier et al. | |
| 2007/0231914 A1* | 10/2007 | Deng | G01N 27/3274 436/70 |
| 2008/0083618 A1* | 4/2008 | Neel | A61B 5/14535 204/403.14 |
| 2008/0105568 A1 | 5/2008 | Wu | |
| 2008/0318259 A1 | 12/2008 | Ranby | |
| 2009/0177406 A1 | 7/2009 | Wu | |
| 2009/0194432 A1 | 7/2009 | Wu | |
| 2009/0223834 A1 | 9/2009 | Cai et al. | |
| 2009/0236237 A1 | 9/2009 | Shinno et al. | |
| 2009/0245994 A1 | 10/2009 | Ritola | |
| 2010/0005865 A1 | 1/2010 | Miura | |
| 2010/0032316 A1 | 2/2010 | Wu | |
| 2010/0089775 A1 | 4/2010 | Chen et al. | |
| 2010/0170807 A1 | 7/2010 | Diebold et al. | |
| 2010/0206749 A1 | 8/2010 | Choi | |
| 2010/0276303 A1 | 11/2010 | Fujiwara et al. | |
| 2010/0283488 A1 | 11/2010 | Nakamura et al. | |
| 2010/0320097 A1 | 12/2010 | Miyazaki et al. | |
| 2011/0030093 A1 | 2/2011 | Dhugga | |
| 2011/0036729 A1 | 2/2011 | Matsuda et al. | |
| 2011/0155585 A1 | 6/2011 | Chatelier et al. | |
| 2011/0168575 A1 | 7/2011 | Lica et al. | |
| 2011/0294554 A1 | 12/2011 | Barratt et al. | |
| 2011/0297557 A1 | 12/2011 | Wu et al. | |
| 2011/0301857 A1 | 12/2011 | Huang et al. | |
| 2012/0031777 A1 | 2/2012 | Burke et al. | |
| 2012/0043227 A1 | 2/2012 | Miyazaki et al. | |
| 2012/0129423 A1 | 5/2012 | Finizza | |
| 2013/0250525 A1 | 9/2013 | Kraft et al. | |

FOREIGN PATENT DOCUMENTS

| | | |
|---|---|---|
| EP | 749332 B1 | 3/1995 |
| EP | 691539 B1 | 6/1995 |
| EP | 1828759 B1 | 10/2005 |
| EP | 1804048 B1 | 12/2005 |
| EP | 2372356 A1 | 10/2011 |
| JP | 2007271622 A | 10/2007 |
| JP | 2011145291 A | 7/2011 |
| JP | 2011158483 A | 8/2011 |
| JP | 2011174943 A | 9/2011 |
| WO | 2004074827 A1 | 9/2004 |
| WO | WO 2006/070200 A1 | 7/2006 |
| WO | WO 2008/040998 A2 | 4/2008 |
| WO | WO 2008/049075 A2 | 4/2008 |
| WO | 2009015077 A1 | 1/2009 |
| WO | WO 2010/049669 A1 | 5/2010 |
| WO | 2011030093 A1 | 3/2011 |
| WO | 2011079938 A2 | 7/2011 |
| WO | 2011082820 A1 | 7/2011 |
| WO | 2011156325 A2 | 12/2011 |

OTHER PUBLICATIONS

International Preliminary Report on Patentability issued in related International Patent Application No. PCT/GB2012/053276, dated Jul. 1, 2014, 11 pages.

U.S. Appl. No. 61/530,795, McColl et al. Not Published.

U.S. Appl. No. 61/530,808, McColl et al. Not Published.

International Application No. PCT/GB2012/053276, PCT International Search Report and Written Opinion, 13 pages, dated May 3, 2013.

"Electric Cell—Substrate Impedance Sensing (ECIS) as a Noninvasive Means to Monitor the Kinetics of Cell Spreading to Artificial Surfaces" by Joachim Wegener, Charles R. Keese, and Ivar Giaever and published by Experimental Cell Research 259, 158-166 (2000) doi:10.1006/excr.2000.4919, available online at http://www.idealibrary.coml.

"Utilization of AC Impedance Measurements for Electrochemical Glucose Sensing Using Glucose Oxidase to Improve Detection Selectivity" by Takuya Kohma, Hidefumi Hasegawa, Daisuke Oyamatsu, and Susumu Kuwabata and published by Bull. Chem. Soc. Jpn. vol. 80, No. 1, 158-165 (2007).

(56) References Cited

OTHER PUBLICATIONS

"Blood Rheology and Hemodynamics" by Oguz K. Baskurt, M.D., Ph.D.,1 and Herbert J. Meiselman, Sc.D., Seminars in Thrombosis and Hemostasis, vol. 29, No. 5, 2003.
Notice of Reasons for Rejection issued in related Japanese Patent Application No. 2014-549534, dated Nov. 8, 2016, 6 pages.
European Search Report issued in related European Patent Application No. 16189622.0, dated Apr. 11, 2017, 13 pages.
Patent Examination Report No. 2 issued in related Australian Patent Application No. 2012321100, dated Nov. 6, 2015, 3 pages.

* cited by examiner

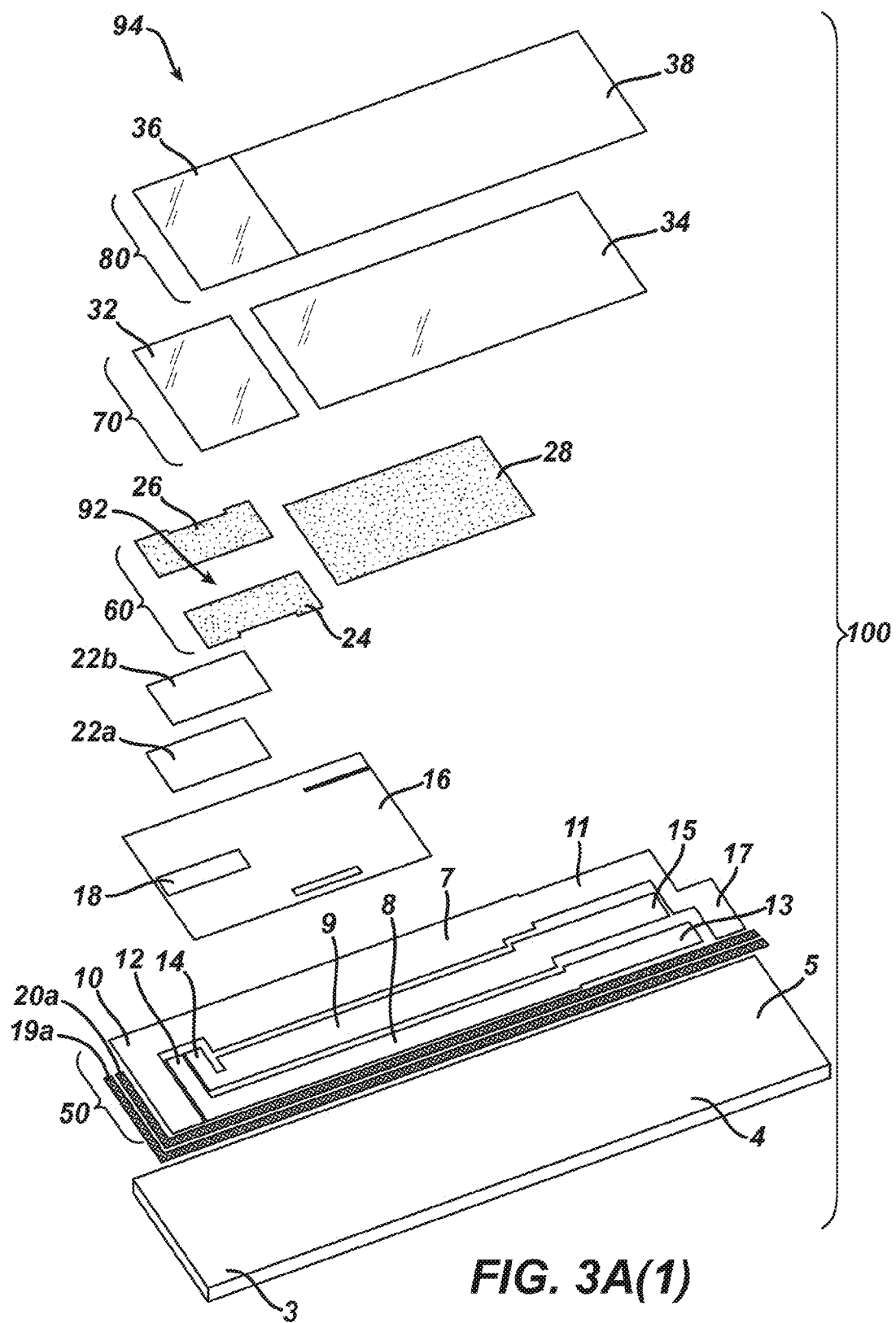
FIG. 3A(1)

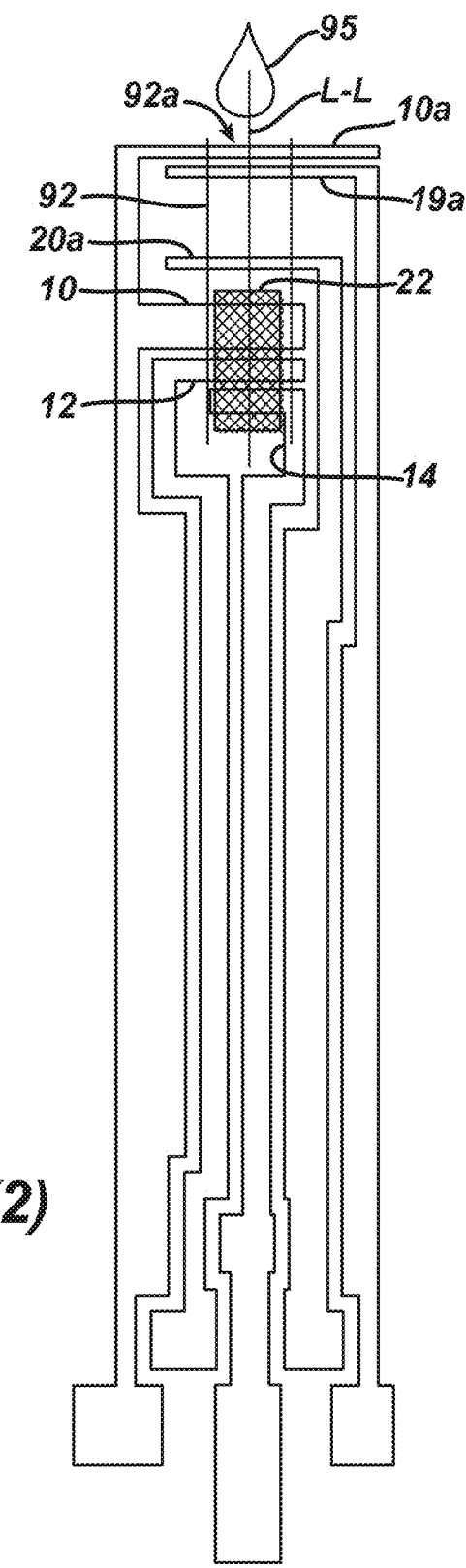
FIG. 3A(2)

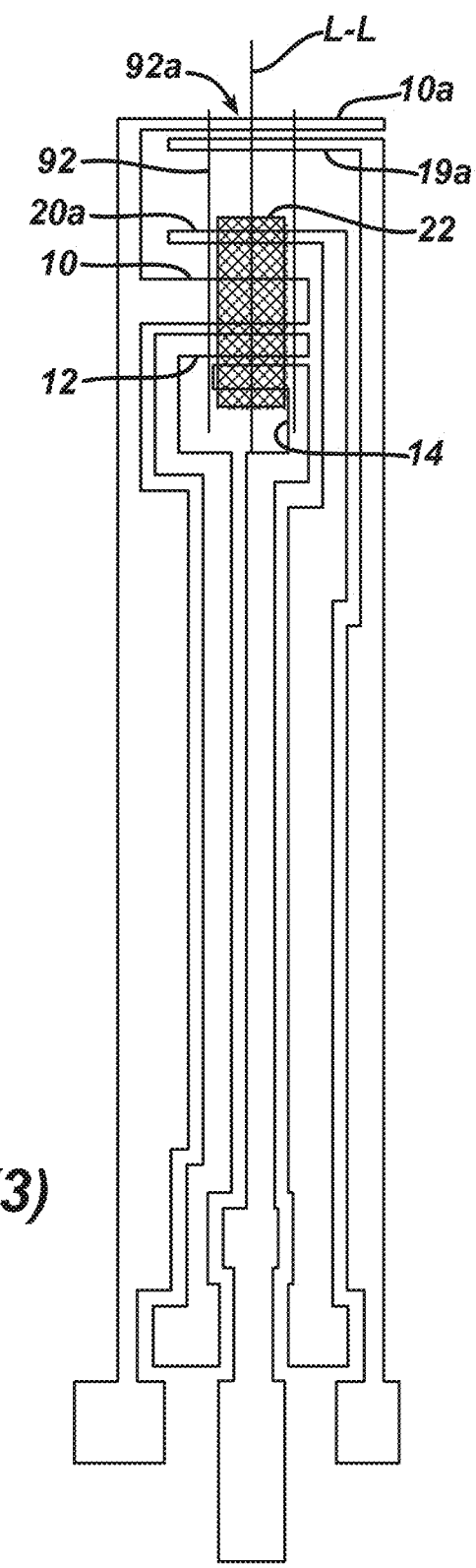
FIG. 3A(3)

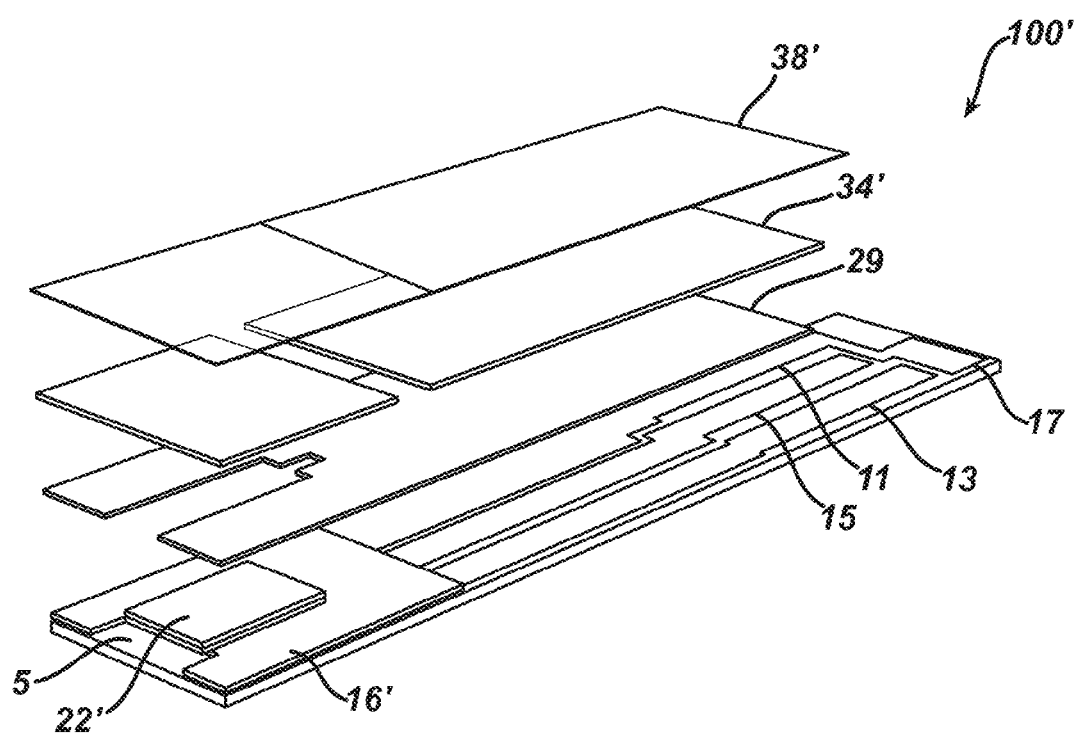
FIG. 3A(4)

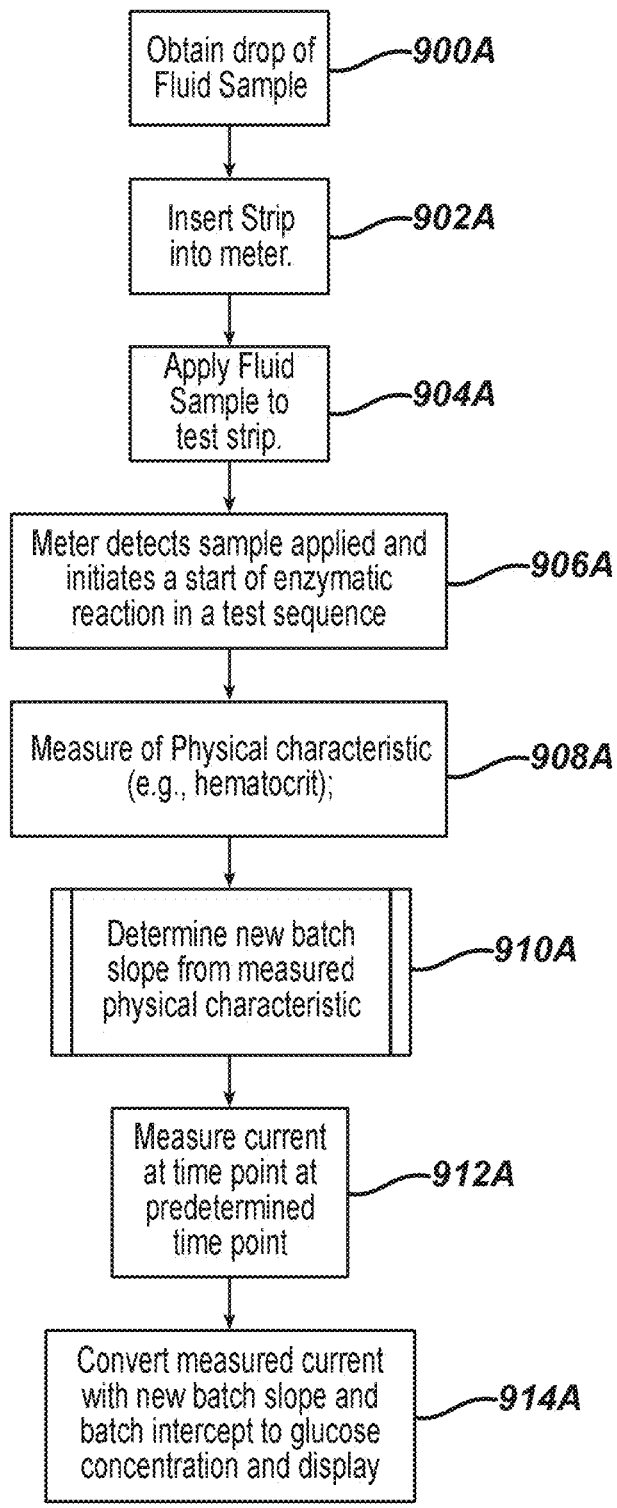
FIG. 6A(1)

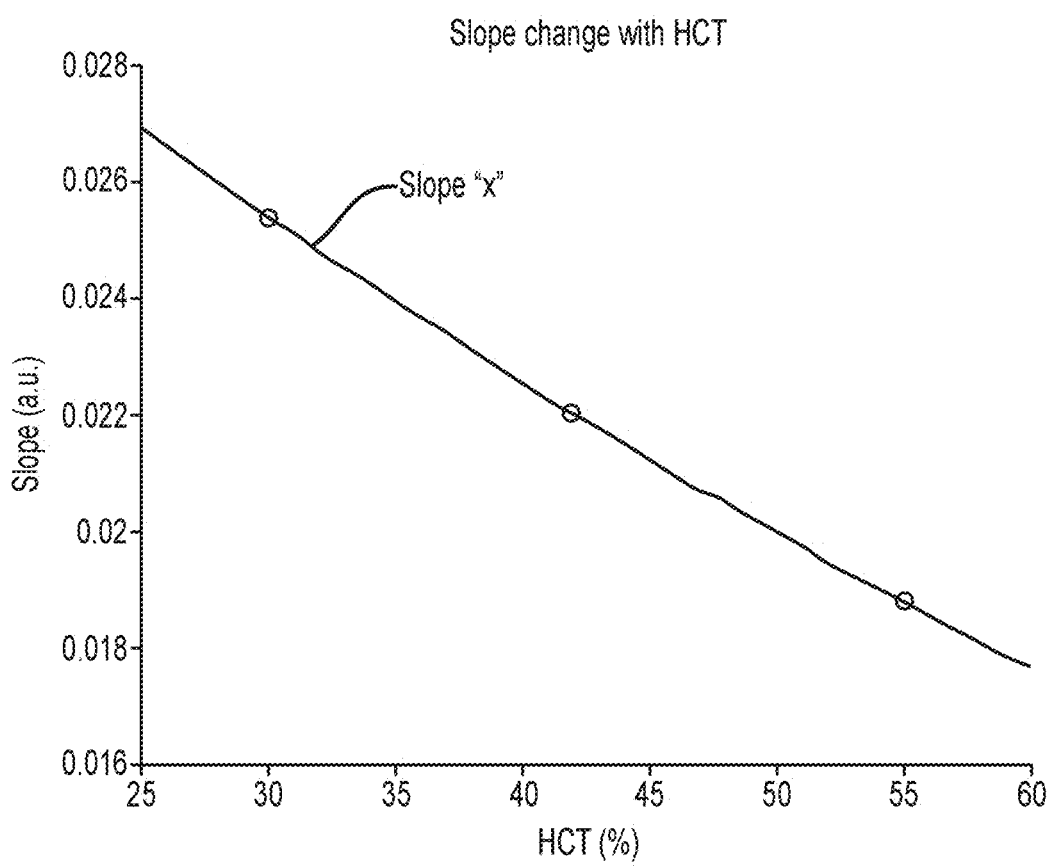
*FIG. 6A(2)*

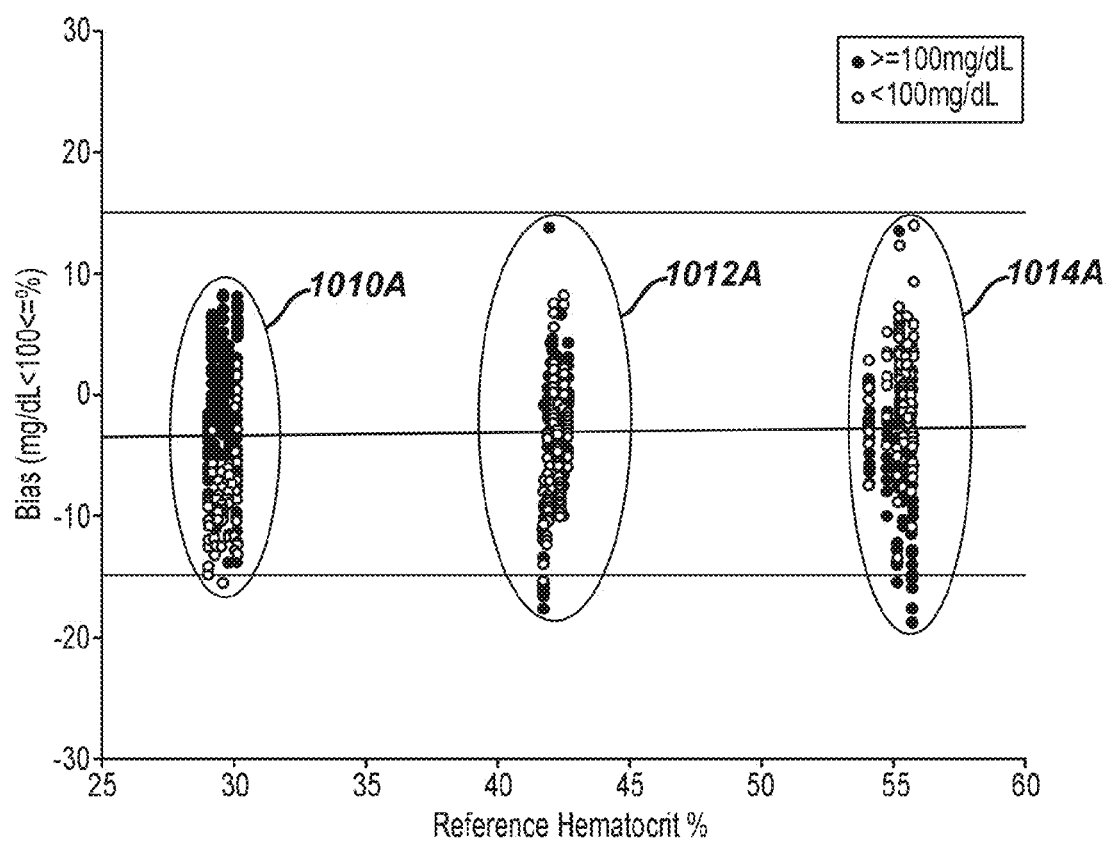
FIG. 6A(3)

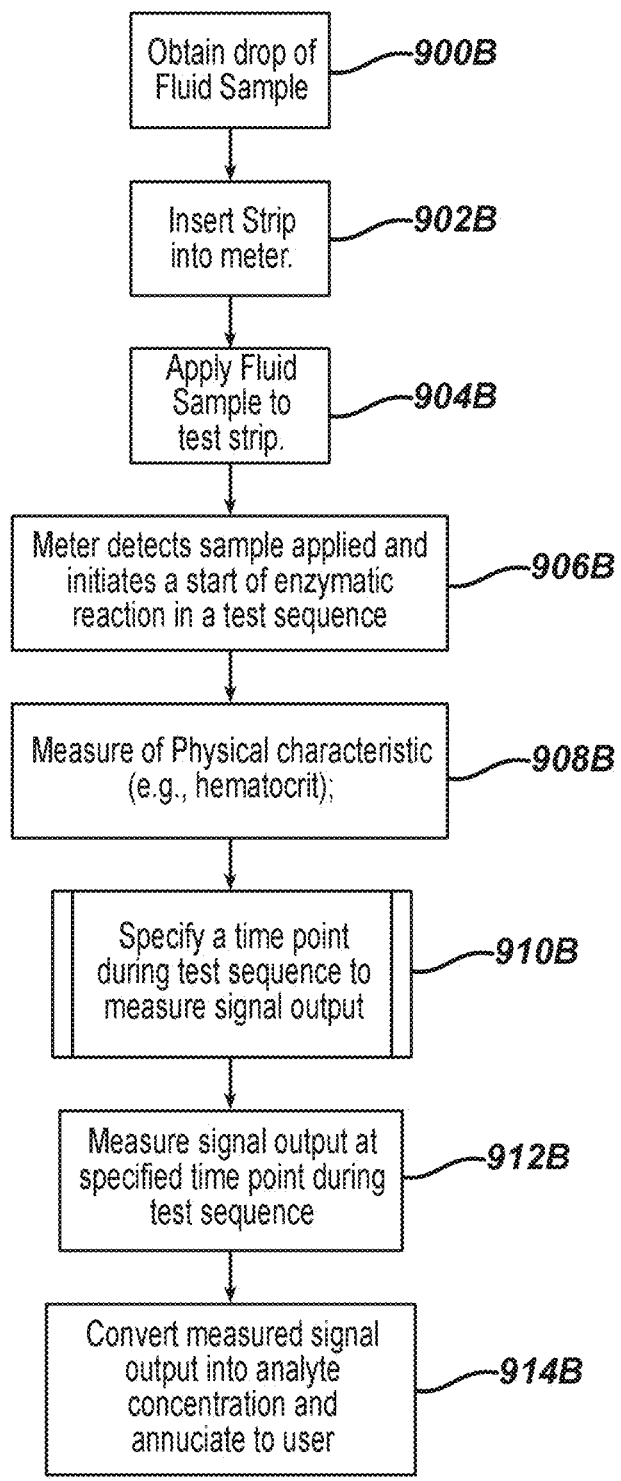
FIG. 6B(1)

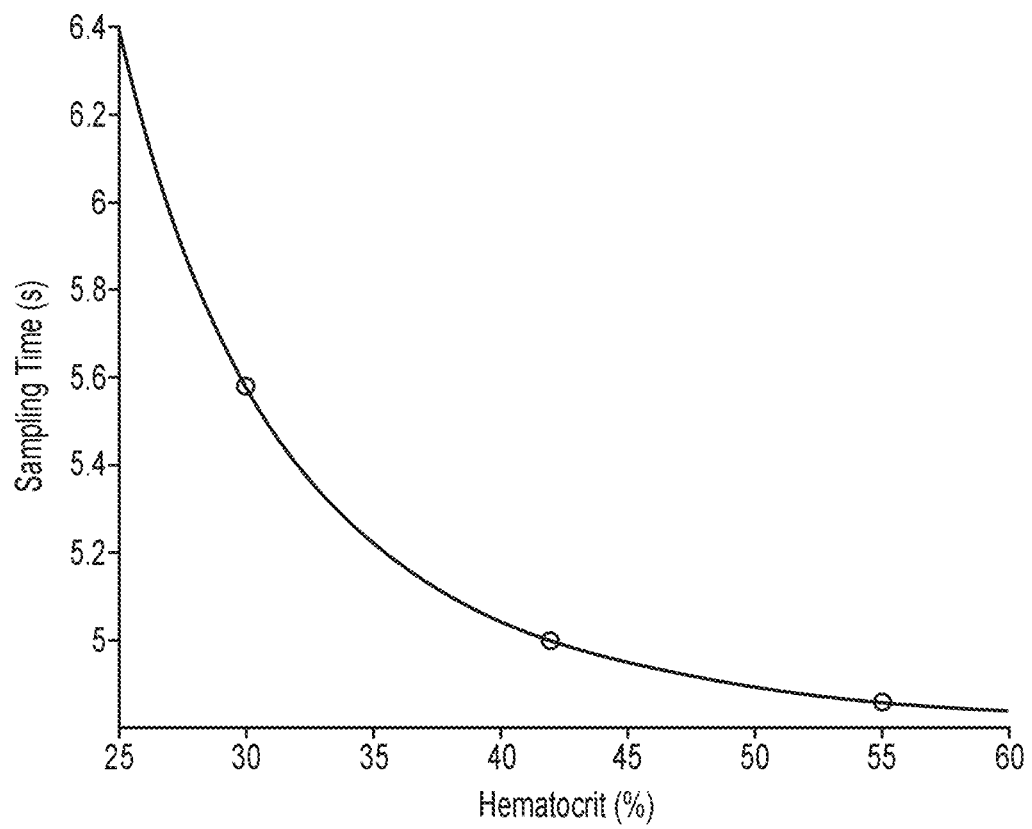
FIG. 6B(2)

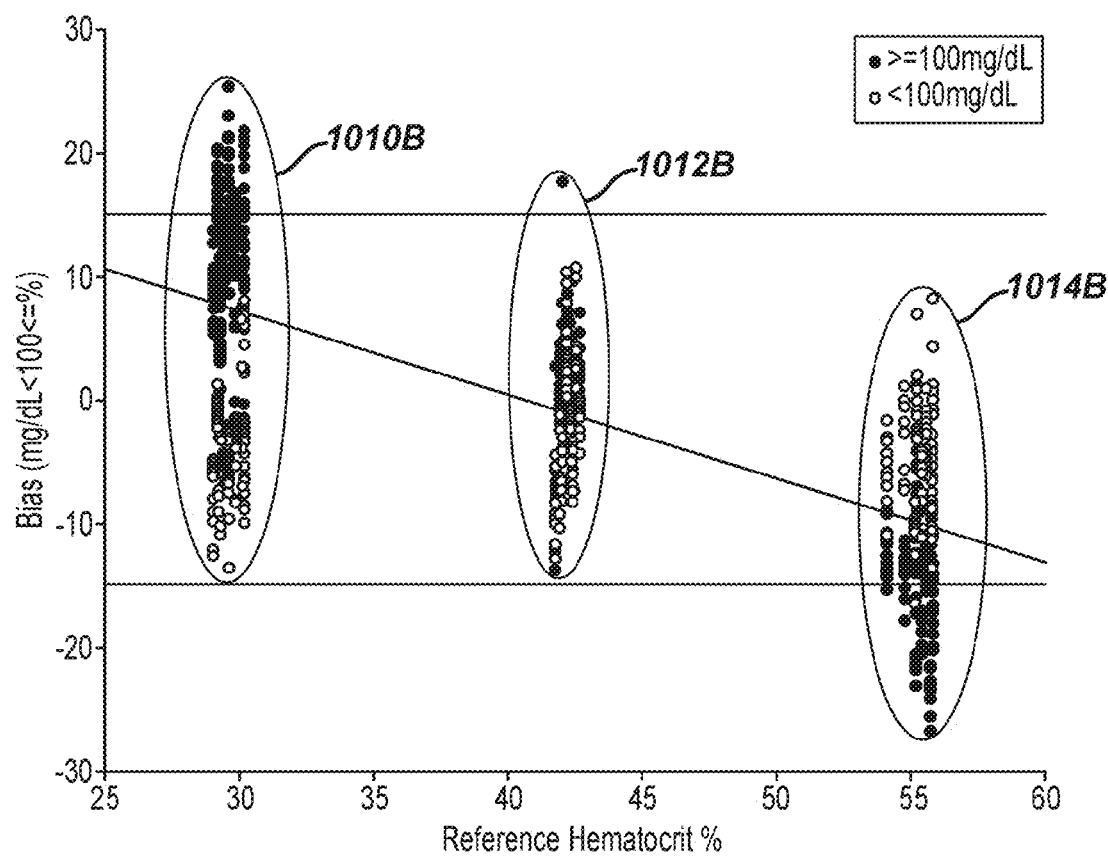
FIG. 6B(3)

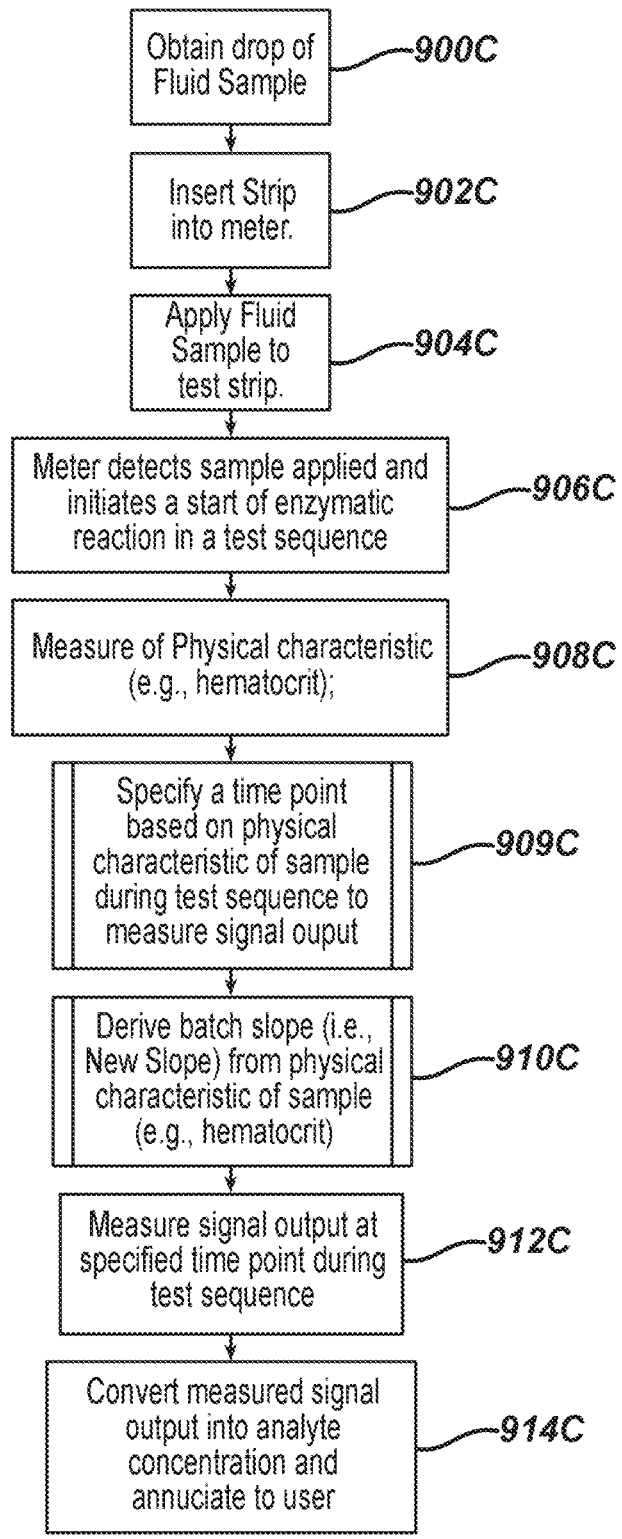
FIG. 6C(1)

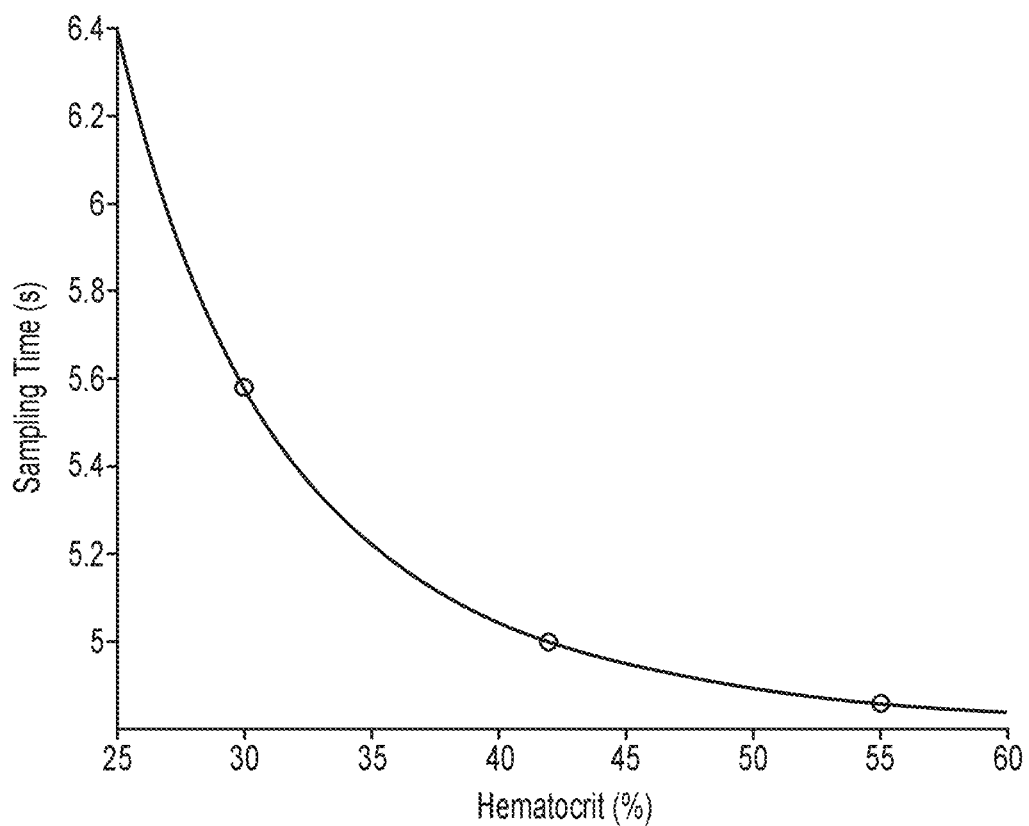
*FIG. 6C(2)*

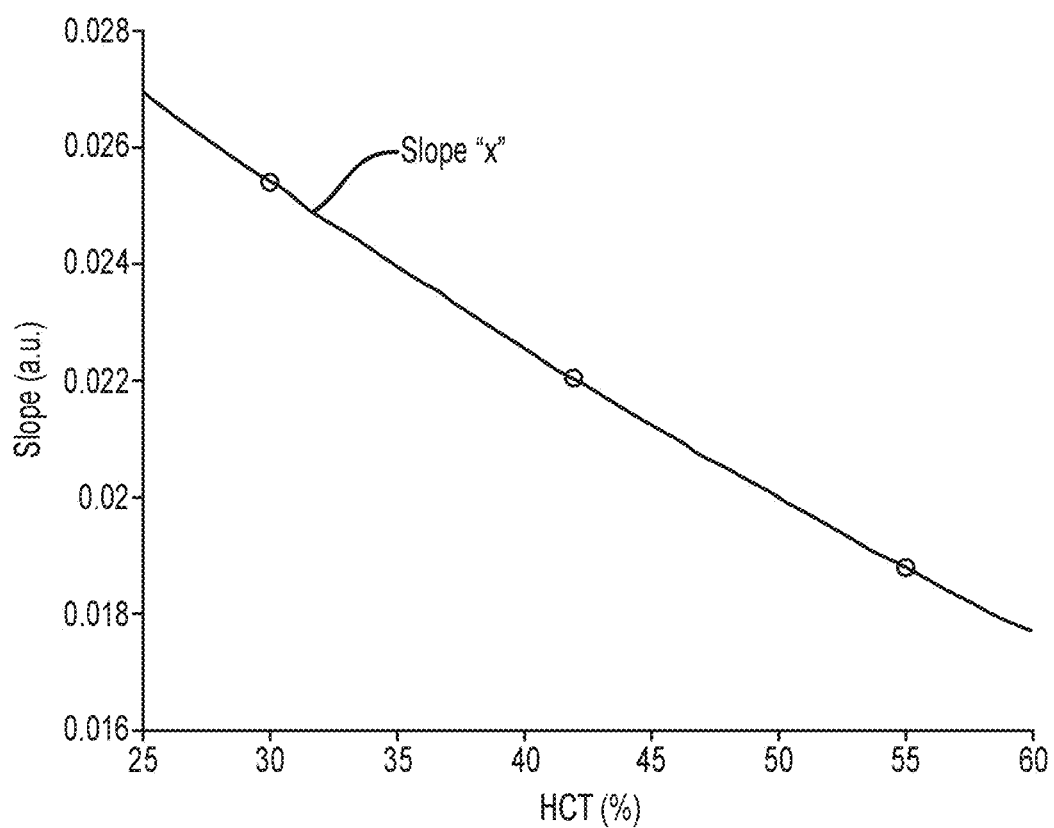
FIG. 6C(3)

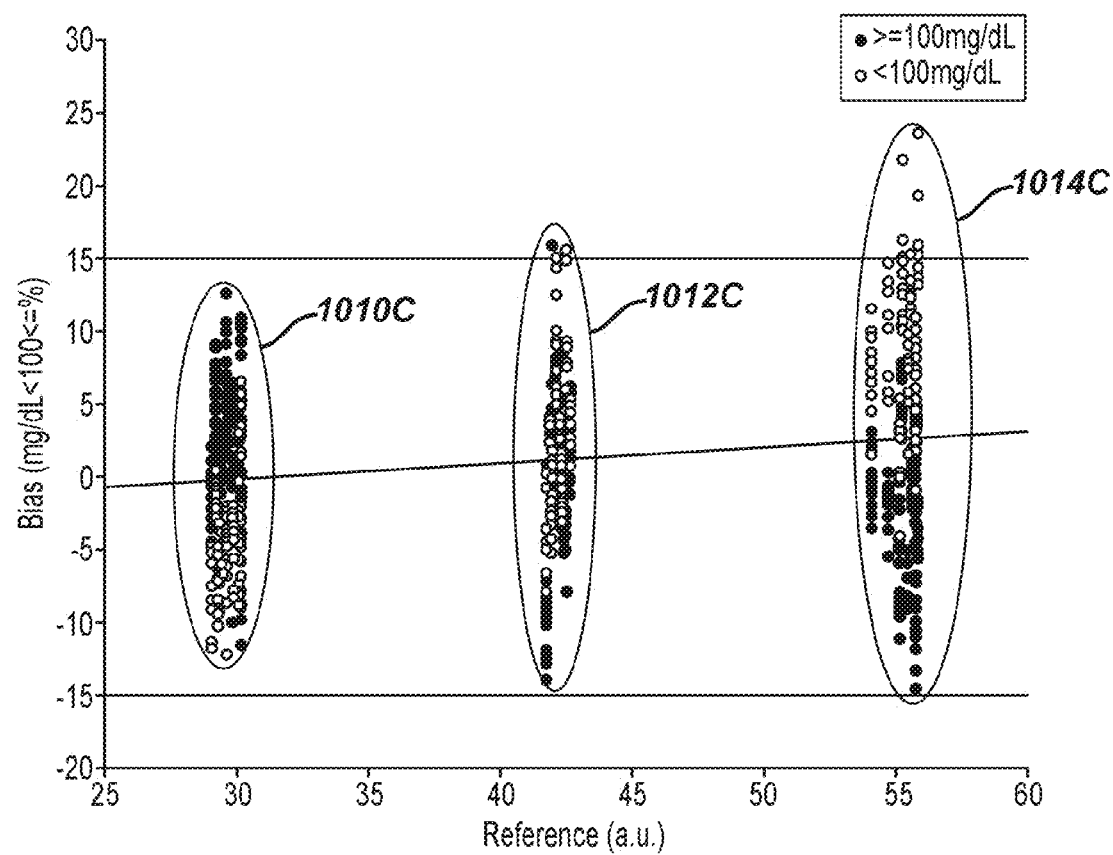
FIG. 6C(4)

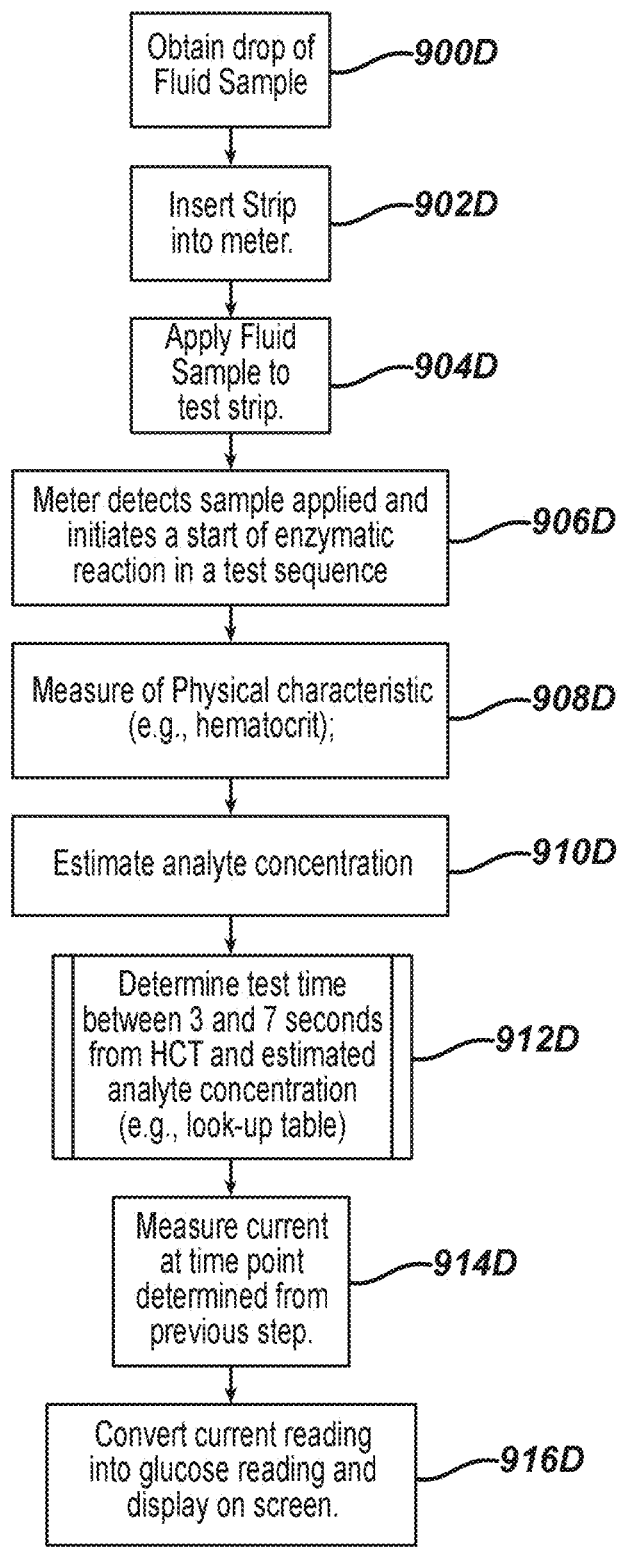
FIG. 6D(1)

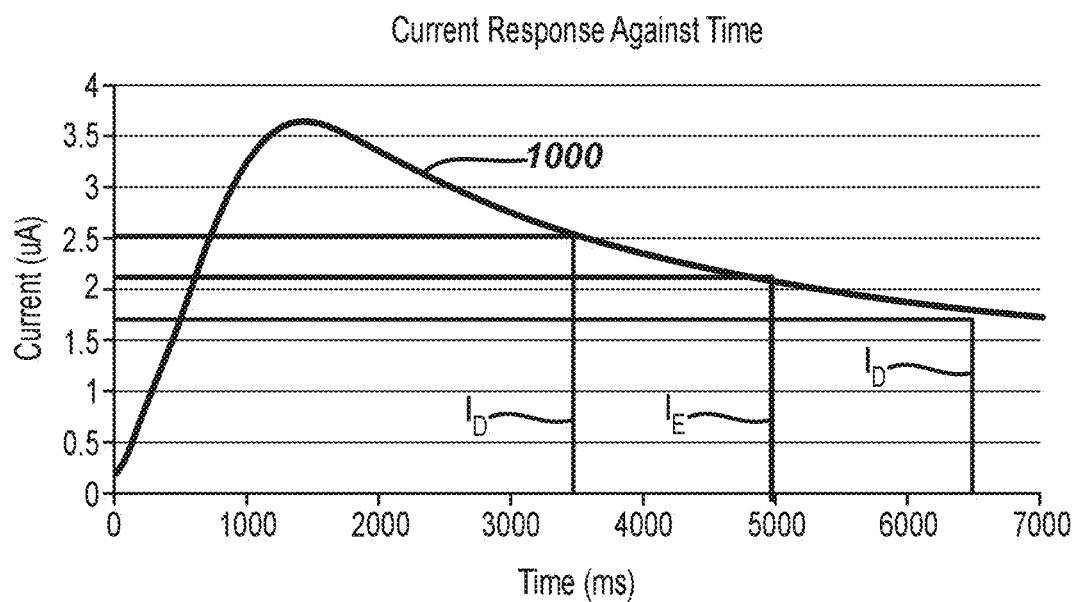
FIG. 6D(2)
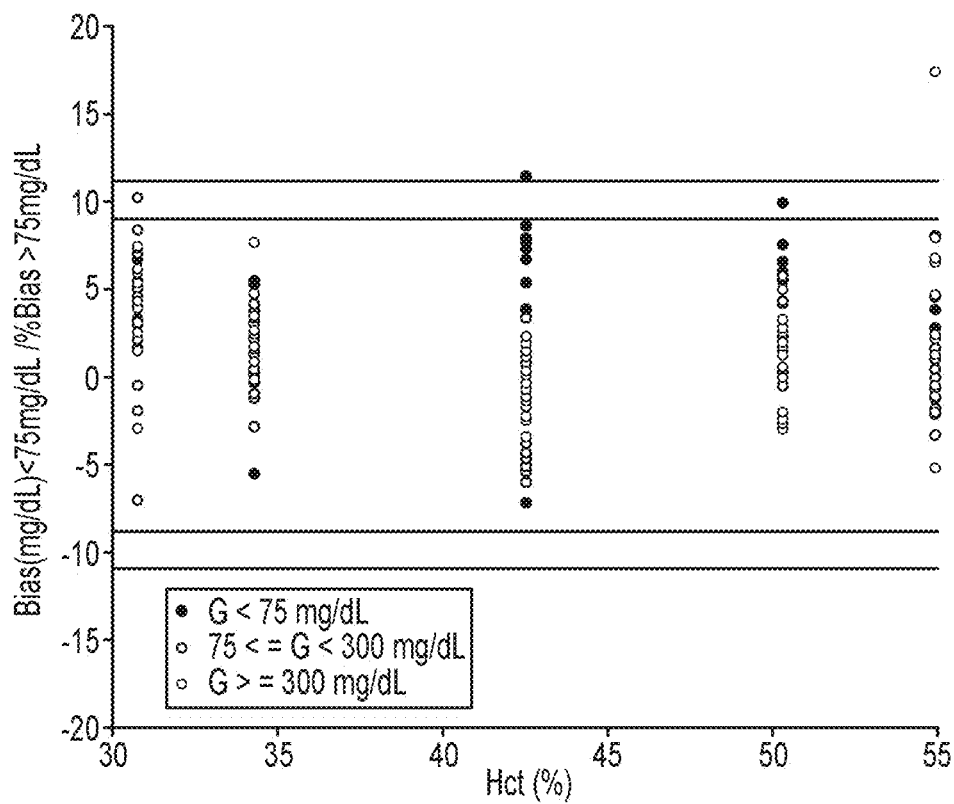
FIG. 6D(3)

ACCURATE ANALYTE MEASUREMENTS FOR ELECTROCHEMICAL TEST STRIP BASED ON SENSED PHYSICAL CHARACTERISTIC(S) OF THE SAMPLE CONTAINING THE ANALYTE

PRIORITY

This National Stage application of International Application PCT/GB2012/053276 filed on Dec. 28, 2012 claims the benefits of priority of prior filed International Patent Applications PCT/GB2012/053277 and PCT/GB2012/053279 on Dec. 28, 2012, in which each of the referenced herein International Patent Applications claims benefits of priority to U.S. Provisional Patent Application Ser. Nos. 61/581,087 filed Dec. 29, 2011; 61/581,089 filed Dec. 29, 2011; 61/581,099 filed Dec. 29, 2011; and 61/581,100 filed Dec. 29, 2011, and U.S. Provisional Patent Application Ser. No. 61/654,013, filed on 31 May 2012, in which all the prior patent applications referenced herein are hereby incorporated by reference as if fully set forth herein this application.

BACKGROUND

Electrochemical glucose test strips, such as those used in the OneTouch® Ultra® whole blood testing kit, which is available from LifeScan, Inc., are designed to measure the concentration of glucose in a physiological fluid sample from patients with diabetes. The measurement of glucose can be based on the selective oxidation of glucose by the enzyme glucose oxidase (GO). The reactions that can occur in a glucose test strip are summarized below in Equations 1 and 2.

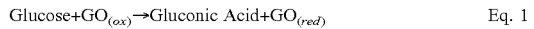

$$\text{Glucose} + \text{GO}_{(ox)} \rightarrow \text{Gluconic Acid} + \text{GO}_{(red)} \quad \text{Eq. 1}$$

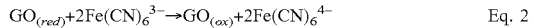

$$\text{GO}_{(red)} + 2\text{Fe(CN)}_6^{3-} \rightarrow \text{GO}_{(ox)} + 2\text{Fe(CN)}_6^{4-} \quad \text{Eq. 2}$$

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test signal applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose signal.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there is less plasma volume to solvate the chemical reactants, and slow diffusion of the mediator. These factors can result in a lower than expected glucose reading as less signal is produced during the electrochemical process. Conversely, at low hematocrit, fewer red blood cells may affect the electrochemical reaction than expected, and a higher measured signal can result. In addition, the physiological fluid sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cells and attenuate the effect of low hematocrit on concentration determinations. Other test strips have included lysis agents and systems configured to determine hemoglobin concentration in an attempt to correct hematocrit. Further, biosensors have been configured to measure hematocrit by measuring an electrical response of the fluid sample via alternating current signals or change in optical variations after irradiating the physiological fluid sample with light, or measuring hematocrit based on a function of sample chamber fill time. These sensors have certain disadvantages. A common technique of the strategies involving detection of hematocrit is to use the measured hematocrit value to correct or change the measured analyte concentration, which technique is generally shown and described in the following respective US Patent Application Publication Nos. 2010/0283488; 2010/0206749; 2009/0236237; 2010/0276303; 2010/0206749; 2009/0223834; 2008/0083618; 2004/0079652; 2010/0283488; 2010/0206749; 2009/0194432; or U.S. Pat. Nos. 7,972,861 and 7,258,769, all of which are incorporated by reference herein to this application.

SUMMARY OF THE DISCLOSURE

Applicants have provided various embodiments of a technique to allow for improved glucose measurement using a relationship between batch slope and physical characteristic (e.g., hematocrit) to derive a new batch slope that can be used to determine the analyte concentration based on this derived batch slope of an electrochemical biosensor. Advantageously, this new technique does not rely on correction(s)

or modification(s) to be made to an analyte measurement, thereby reducing test time while at the same time improving accuracy.

In a first aspect of applicants' disclosure, a method of determining an analyte concentration from a fluid sample (which may be a physiological sample) with a biosensor (which may be in the form of a test strip but is not limited to a test strip) is provided. The biosensor has at least two electrodes and a reagent disposed on at least one of the electrodes. The method can be achieved by: depositing a fluid sample (which may be a physiological sample) on the at least two electrodes to start an analyte test sequence; applying a first signal to the sample to measure or estimate a physical characteristic of the sample; deriving a batch slope for the biosensor based on the measured or estimated physical characteristic from an equation of the form:

$$x = aH^2 + bH + c$$

where
  x represents a derived batch slope;
  H is measured or estimated physical characteristic;
  a represents about 1.4e−6, or is equal to 1.4e−6, or is equal to 1.4e−6+/−10%, 5% or 1% of 1.4e−6;
  b represents about −3.8e−4, or is equal to −3.8e−4, or is equal to −3.8e−4+/−10%, 5% or 1% of −3.8e−4;
  c represents about 3.6e−2, or is equal to 3.6e−2, or is equal to −3.6e−2+/−10%, 5% or 1% of 3.6e−2;
driving a second signal to the sample; and measuring an output signal from at least one of the at least two electrodes; calculating an analyte concentration based on the measured output signal and derived batch slope with an equation of the form:

$$G_0 = \left[\frac{I_E - \text{Intercept}}{x}\right]$$

where
  $G_0$ represents an analyte concentration
  $I_E$ represents, or is, a signal (value or measurement; proportional to analyte concentration) measured at a predetermined or specified sampling time, which may be the total signal measured at the predetermined or specified sampling time;
  Intercept represents a calibration parameter for a batch of biosensors;
  x represents, or is, the derived batch slope from the deriving step.

In a second aspect of applicants' disclosure, a method of determining an analyte concentration from a fluid sample (which may be a physiological sample) with a biosensor (which may be in the form of a test strip but is not limited to a test strip) is provided. The biosensor has at least two electrodes and a reagent disposed on at least one of the electrodes. The method can be achieved by: depositing a fluid sample (which may be a physiological sample) on the at least two electrodes to start an analyte test sequence; applying a first signal to the sample to measure a physical characteristic of the sample; deriving a batch slope for the biosensor based on the measured or estimated physical characteristic; driving a second signal to the sample; and measuring an output signal from at least one of the at least two electrodes; calculating an analyte concentration based on the measured output signal and derived batch slope from the measured or estimated physical characteristic of the sample.

In any of the aspects described herein the following features may also be utilized in various combinations with the previously disclosed aspects: the applying of the first signal and the driving of the second signal may be in sequential order; the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density of the sample; the directing may include driving first and second alternating signals at different respective frequencies in which a first frequency is lower than the second frequency; the first frequency may be at least one order of magnitude lower than the second frequency; and/or the first frequency may include any frequency in the range of about 10 kHz to about 250 kHz, or about 10 kHz to about 90 kHz.

In these aspects, the deriving may include calculating a batch slope from an equation of the form:

$$x = aH^2 + bH + c$$

where
  x represents, or is, a derived batch slope from the deriving step;
  H represents, or is, measured or estimated physical characteristic (e.g. hematocrit);
  a represents about 1.4e−6, or is equal to 1.4e−6, or is equal to 1.4e−6+/−10%, 5% or 1% of the numerical value provided hereof;
  b represents about −3.8e−4, or is equal to −3.8e−4, or is equal to −3.8e−4+/−10%, 5% or 1% of the numerical value provided hereof;
  c represents about 3.6e−2, or is equal to 3.6e−2, or is equal to −3.6e−2+/−10%, 5% or 1% of the numerical value provided hereof;

Furthermore, the calculating of the analyte concentration may include utilizing an equation of the form:

$$G_0 = \left[\frac{I_E - \text{Intercept}}{x}\right]$$

where
  $G_0$ represents, or is, an analyte concentration
  $I_E$ represents, or is, a signal (proportional to analyte concentration) which may be the total signal measured at a predetermined time, for example at least one of 2.5 seconds or 5 seconds, or at one of 2.5 seconds or 5 seconds (about or exactly) after a start of the test sequence; and wherein the total signal means one signal from each electrode summed or the signal from one electrode being doubled;
  Intercept represents, or is, a calibration parameter for a batch of biosensors;
  x represents, or is, a derived batch slope from the deriving step.

In a third aspect of applicants' disclosure, an analyte measurement system is provided that includes a test strip and an analyte meter. The test strip includes a substrate with a plurality of electrodes connected to respective electrode connectors. The analyte meter includes a housing, a test strip port, and a processor. The strip port connector is configured to connect to the respective electrode connectors of the test strip. The microprocessor is in electrical communication with the test strip port connector to apply electrical signals or sense electrical signals from the plurality of electrodes during a test sequence. The microprocessor is configured to, during the test sequence: (a) apply a first signal to the plurality of electrodes so that a batch slope defined by a physical characteristic of a physiological fluid sample is derived and (b) apply a second signal to the plurality of electrodes so that an analyte concentration is determined based on the derived batch slope.

And for these aspects, the following features may also be utilized in various combinations with these previously disclosed aspects: the plurality of electrodes may include at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; the at least two electrodes may include two electrodes to measure the physical characteristic and the analyte concentration; the plurality of electrodes may include two electrodes to measure the physical characteristic and the analyte concentration; alternatively, all of the electrodes are disposed on the same plane defined by the substrate; a reagent is disposed proximate the at least two other electrodes and no reagent is disposed on the at least two electrodes; and/or the batch slope may be calculated from an equation of the form:

$$x = aH^2 + bH + c$$

where
 x represents, or is, a derived batch slope from the deriving step;
 H represents, or is, measured or estimated physical characteristic (e.g. hematocrit);
 a represents about 1.4e−6, or is equal to 1.4e−6, or is equal to 1.4e−6+/−10%, 5% or 1% of the numerical value provided hereof;
 b represents about −3.8e−4, or is equal to −3.8e−4, or is equal to −3.8e−4+/−10%, 5% or 1% of the numerical value provided hereof;
 c represents about 3.6e−2, or is equal to 3.6e−2, or is equal to −3.6e−2+/−10%, 5% or 1% of the numerical value provided herein.

Furthermore, in these aspects, the analyte concentration may be determined from an equation of the form:

$$G_0 = \left[\frac{I_E - \text{Intercept}}{x}\right]$$

where
 $G_0$ represents, or is, an analyte concentration
 $I_E$ represents, or is, a signal (proportional to analyte concentration) measured at a predetermined or specified sampling time, which may be the total signal measured at the predetermined or specified sampling time;
 Intercept represents, or is, the calibration parameter for a batch of test strips;
 x represents, or is, the derived batch slope from the deriving step.

In a fourth aspect of applicants' disclosure, an analyte measurement system is provided that includes a test strip and an analyte meter. The test strip includes a substrate with a plurality of electrodes connected to respective electrode connectors. The analyte meter includes a housing, a test strip port, and a processor. The strip port connector is configured to connect to the respective electrode connectors of the test strip. The microprocessor is in electrical communication with the test strip port connector to apply electrical signals or sense electrical signals from the plurality of electrodes during a test sequence. The microprocessor is configured to, during a test sequence: (a) apply a first signal to the plurality of electrodes so that a batch slope defined by a physical characteristic of a physiological fluid sample is derived and (b) apply a second signal to the plurality of electrodes so that an analyte concentration is determined based on the derived batch slope obtained from the physical characteristic of the sample within about 10 seconds of a start of the test sequence.

And for these aspects, the following features may also be utilized in various combinations with these previously disclosed aspects: the plurality of electrodes may include at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; the at least two electrodes may include two electrodes to measure the physical characteristic and the analyte concentration; the plurality of electrodes may include two electrodes to measure the physical characteristic and the analyte concentration; all of the electrodes may be disposed on the same plane defined by the substrate; a reagent is disposed proximate the at least two other electrodes and no reagent disposed on the at least two electrodes; and/or the batch slope may be calculated from an equation of the form:

$$x = aH^2 + bH + c$$

where
 x represents, or is, a derived batch slope from the deriving step;
 H represents, or is, measured or estimated physical characteristic (e.g. hematocrit);
 a represents about 1.4e−6, or is equal to 1.4e−6, or is equal to 1.4e−6+/−10%, 5% or 1% of the numerical value provided hereof;
 b represents about −3.8e−4, or is equal to −3.8e−4, or is equal to −3.8e−4+/−10%, 5% or 1% of the numerical value provided hereof;
 c represents about 3.6e−2, or is equal to 3.6e−2, or is equal to −3.6e−2+/−10%, 5% or 1% of the numerical value provided hereof.

In these aspects, the analyte concentration may be calculated from an equation of the form:

$$G_0 = \left[\frac{I_E - \text{Intercept}}{x}\right]$$

where
 $G_0$ represents, or is, an analyte concentration
 $I_E$ represents, or is, a signal (value or measurement; proportional to analyte concentration) measured at a predetermined or specified sampling time, which may be the total signal measured at the predetermined or specified sampling time;
 Intercept represents, or is, a calibration parameter for a batch of test strips;

x represents, or is, a derived batch slope from the deriving step.

In a fifth aspect of applicants' disclosure, a method of demonstrating increased accuracy of a test strip is provided. The method can be achieved by: providing a batch of test strips; introducing a referential sample containing a referential concentration of an analyte to each test strip of the batch of test strips to initiate a test sequence; reacting the analyte with a reagent on each test strip to cause a physical transformation of the analyte proximate the two electrodes (which may be between the two electrodes); determining a physical characteristic of the referential sample; deriving a batch slope for the batch of test strips based on the determined physical characteristic of the referential sample; sampling an electrical output of the referential sample at a predetermined time point during the test sequence; calculating an analyte concentration based on the defined batch slope and sampled electrical output to provide for a final analyte concentration value for each test strip of the batch of test strips such that at least 95% of the final analyte concentration values of the batch of test strips are within ±15% of the referential analyte concentration.

And for these aspects, the following features may also be utilized in various combinations with these previously disclosed aspects: the determining may include applying a first signal to the sample to measure a physical characteristic of the sample; the sampling may include driving a second signal to the sample; the applying of the first signal and the driving of the second signal may be in sequential order; the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density; the directing may include driving first and second alternating signals at different respective frequencies in which a first frequency is lower than the second frequency; the first frequency may be at least one order of magnitude lower than the second frequency; the first frequency may include any frequency in the range of about 10 kHz to about 250 kHz, or about 10 kHz to about 90 kHz; and/or the deriving may include calculating a batch slope from an equation of the form:

$$x = aH^2 + bH + c$$

where
  x represents, or is, a derived batch slope from the deriving step;
  H represents, or is, measured, determined or estimated physical characteristic (e.g. hematocrit);
  a represents about 1.4e−6, or is equal to 1.4e−6, or is equal to 1.4e−6+/−10%, 5% or 1% of the numerical value provided hereof;
  b represents about −3.8e−4, or is equal to −3.8e−4, or is equal to −3.8e−4+/−10%, 5% or 1% of the numerical value provided hereof;
  c represents about 3.6e−2, or is equal to 3.6e−2, or is equal to −3.6e−2+/−10%, 5% or 1% of the numerical value provided hereof;

In these aspects, the calculating of the analyte concentration may include utilizing an equation of the form:

$$G_0 = \left[ \frac{I_E - \text{Intercept}}{x} \right]$$

where
  $G_0$ represents, or is, an analyte concentration
  $I_E$ represents, or is, a signal (value or measurement; proportional to analyte concentration) measured at a predetermined or specified sampling time, which may be the total signal measured at the predetermined or specified sampling time;
  Intercept represents, or is, a calibration parameter for a batch of test strips;
  x represents, or is, a derived batch slope from the deriving step.

In a sixth aspect of applicants' disclosure, a method of determining an analyte concentration from a fluid sample (which may be a physiological sample) is provided. The method can be achieved by: depositing a fluid sample (which may be a physiological sample) on a biosensor; applying signals to the sample to transform the analyte into a different material; measuring or estimating a physical characteristic of the sample; evaluating signal output from the sample; deriving a parameter of the biosensor from the measured or estimated physical characteristic; and determining an analyte concentration based on the derived parameter of the biosensor and the signal output of the sample.

And for these aspects, the following features may also be utilized in various combinations with these previously disclosed aspects: the measuring may include applying a first signal to the sample to measure a physical characteristic of the sample; the evaluating may include driving a second signal to the sample; the applying of the first signal and the driving of the second signal may be in sequential order; the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density; the directing may include driving first and second alternating signals at different respective frequencies in which a first frequency is lower than the second frequency; the first frequency may be at least one order of magnitude lower than the second frequency; the first frequency may include any frequency in the range of about 10 kHz to about 250 kHz, or about 10 kHz to about 90 kHz; the derived parameter may be a batch slope; and/or the deriving may include calculating a batch slope from an equation of the form:

$$x = aH^2 + bH + c$$

where
  x represents, or is, a derived batch slope from the deriving step;
  H represents, or is, measured or estimated physical characteristic (e.g. hematocrit);
  a represents about 1.4e−6, or is equal to 1.4e−6, or is equal to 1.4e−6+/−10%, 5% or 1% of the numerical value provided hereof;
  b represents about −3.8e−4, or is equal to −3.8e−4, or is equal to −3.8e−4+/−10%, 5% or 1% of the numerical value provided hereof;

c represents about 3.6e−2, or is equal to 3.6e−2, or is equal to −3.6e−2+/−10%, 5% or 1% of the numerical value provided herein.

In these aspects, the calculating of the analyte concentration may include utilizing an equation of the form:

$$G_0 = \left[\frac{I_E - \text{Intercept}}{x}\right]$$

where
G₀ represents, or is, an analyte concentration
$I_E$ represents, or is, a signal (value or measurement; proportional to analyte concentration) measured at a predetermined or specified sampling time, which may be the total signal measured at the predetermined or specified sampling time;
Intercept represents, or is, a calibration parameter for a batch of test strips;
x represents a derived batch slope from the deriving step.

In a seventh aspect of applicants' disclosure, a method of determining an analyte concentration from a fluid sample (which may be a physiological sample) with a biosensor (e.g. a test strip) is provided. The biosensor has at least two electrodes and a reagent disposed on at least one electrode of the electrodes. The method can be achieved by: depositing a fluid sample (which may be a physiological sample) on the at least two electrodes to start an analyte test sequence; applying a first signal to the sample to derive a physical characteristic of the sample; obtaining a physical characteristic of the sample; specifying a sampling time based on the obtained physical characteristic; driving a second signal to the sample; and measuring an output signal at the specified sampling time from at least one electrode of the at least two electrodes; and calculating an analyte concentration based on the measured output signal.

For the seventh aspect of applicants' disclosure, the following features may also be utilized in various combinations: the applying of the first signal and the driving of the second signal may be in sequential order; the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density of the sample; the directing may include driving first and second alternating signals at different respective frequencies in which a first frequency is lower than the second frequency; the first frequency may be at least one order of magnitude lower than the second frequency; the first frequency may include any frequency in the range of about 10 kHz to about 250 kHz, or about 10 kHz to about 90 kHz; and/or the specified sampling time may be calculated using an equation of the form:

SpecifiedSamplingTime=$x_1 H^{x_2} + x_3$ where
"SpecifiedSamplingTime" is designated as a time point from the start of the test sequence at which to sample or measure the output signal (e.g. output signal) of the test strip, H represents the physical characteristic of the sample;
$x_1$ is about 4.3e5, or is equal to 4.3e5, or is equal to 4.3e5+/−10%, 5% or 1% of the numerical value provided hereof;
$x_2$ is about −3.9, or is equal to −3.9, or is equal to −3.9+/−10%, 5% or 1% of the numerical value provided hereof; and
$x_3$ is about 4.8, or is equal to 4.8, or is equal to 4.8+/−10%, 5% or 1% of the numerical value provided herein.

Additionally, in the seventh aspect of applicants' disclosure, the calculating of the analyte concentration may be computed with an equation of the form:

$$G_0 = \left[\frac{I_E - \text{Intercept}}{\text{Slope}}\right]$$

where
G₀ represents, or is, an analyte concentration
$I_E$ represents, or is, a signal (proportional to analyte concentration) measured at the SpecifiedSamplingTime, which may be the total signal measured at the SpecifiedSamplingTime;
Slope represents, or is, the value obtained from calibration testing of a batch of test strips of which this particular strip comes from; and
Intercept represents, or is, the value obtained from calibration testing of a batch of test strips from which this particular strip comes.

In an eighth aspect of applicants' disclosure, an analyte measurement system is provided that includes a test strip and a test meter. The test strip includes a substrate and a plurality of electrodes connected to respective electrode connectors. The analyte meter includes a housing, a test strip port connector configured to connect to the respective electrode connectors of the test strip and a microprocessor. The microprocessor is in electrical communication with the test strip port connector to apply electrical signals or sense electrical signals from the plurality of electrodes during a test sequence. The microprocessor is configured to, during the test sequence: (a) apply a first signal to the plurality of electrodes so that a specified sampling time determined from a physical characteristic of a physiological fluid sample is derived, (b) apply a second signal to the plurality of electrodes, and (c) measure a signal output from one of the plurality of electrodes at the specified sampling time so that an analyte concentration is determined.

And for these aspects, the following features may also be utilized in various combinations with these previously disclosed aspects: the plurality of electrodes may include at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; the at least two electrodes may comprise two electrodes to measure the physical characteristic and the analyte concentration; the plurality of electrodes may comprise two electrodes to measure the physical characteristic and the analyte concentration; all of the electrodes may be disposed on the same plane defined by the substrate; a reagent may be disposed proximate the at least two other electrodes and no reagent disposed on the at least two electrodes; and/or the specified sampling time may be calculated using an equation of the form:

$$\text{SpecifiedSamplingTime} = x_1 H^{x_2} + x_3$$

where
"SpecifiedSamplingTime" is designated as a time point from the start of the test sequence at which to sample the output signal (e.g. output signal) of the test strip,
H represents the physical characteristic of the sample;
$x_1$ is about 4.3e5, or is equal to 4.3e5, or is equal to 4.3e5+/−10%, 5% or 1% of the numerical value provided hereof;
$x_2$ is about −3.9, or is equal to −3.9, or is equal to −3.9+/−10%, 5% or 1% of the numerical value provided hereof; and
$x_3$ is about 4.8, or is equal to 4.8, or is equal to 4.8+/−10%, 5% or 1% of the numerical value provided herein.

Additionally, in these aspects, the analyte concentration is determined from an equation of the form:

$$G_0 = \left[\frac{I_E - \text{Intercept}}{\text{Slope}}\right]$$

where
$G_0$ represents, or is, an analyte concentration
$I_E$ represents, or is, a signal (value or measurement; proportional to analyte concentration) measured at the SpecifiedSamplingTime, which may be the total signal measured at the SpecifiedSamplingTime;
Slope represents, or is, the value obtained from calibration testing of a batch of test strips of which this particular strip comes from; and
Intercept represents, or is, the value obtained from calibration testing of a batch of test strips from which this particular strip comes from.

In a ninth aspect of applicants' disclosure, an analyte measurement system is provided that includes a test strip and a test meter. The test strip includes a substrate and a plurality of electrodes connected to respective electrode connectors. The analyte meter includes a housing, a test strip port connector configured to connect to the respective electrode connectors of the test strip and a microprocessor. The microprocessor is in electrical communication with the test strip port connector to apply electrical signals or sense electrical signals from the plurality of electrodes. The microprocessor is configured to, during a test sequence: (a) apply a first signal to the plurality of electrodes so that a specified sampling time determined from a physical characteristic of a physiological fluid sample is derived, (b) apply a second signal to the plurality of electrodes, and (c) measure a signal output from one of the plurality of electrodes at the specified sampling time so that an analyte concentration of the sample is determined based on the specified sampling time within about 10 seconds of a start of the test sequence.

And for these aspects, the following features may also be utilized in various combinations with these previously disclosed aspects: the plurality of electrodes may include at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; the at least two electrodes may comprise two electrodes to measure the physical characteristic and the analyte concentration; all of the electrodes may be disposed on the same plane defined by the substrate; a reagent may be disposed proximate the at least two other electrodes and no reagent disposed on the at least two electrodes; and/or the specified sampling time may be calculated using an equation of the form:

$$\text{SpecifiedSamplingTime} = x_1 H^{x_2} + x_3$$

where
"SpecifiedSamplingTime" is designated as a time point from the start of the test sequence at which to sample the output signal (e.g. output signal) of the test strip,
H represents, or is, the physical characteristic of the sample;
$x_1$ is about 4.3e5, or is equal to 4.3e5, or is equal to 4.3e5+/−10%, 5% or 1% of the numerical value provided hereof;
$x_2$ is about −3.9, or is equal to −3.9, or is equal to −3.9+/−10%, 5% or 1% of the numerical value provided hereof; and
$x_3$ is about 4.8, or is equal to 4.8, or is equal to 4.8+/−10%, 5% or 1% of the numerical value provided herein.

Additionally, for these aspects, an analyte concentration may be calculated from an equation of the form:

$$G_0 = \left[\frac{I_E - \text{Intercept}}{\text{Slope}}\right]$$

where
$G_0$ represents, or is, an analyte concentration
$I_E$ represents, or is, a signal (proportional to analyte concentration) measured at the SpecifiedSamplingTime, which may be the total signal measured at the SpecifiedSamplingTime;
Slope represents, or is, the value obtained from calibration testing of a batch of test strips of which this particular strip comes from; and
Intercept represents, or is, the value obtained from calibration testing of a batch of test strips of which this particular strip comes from.

In a tenth aspect of applicants' disclosure, a method of determining an analyte concentration from a fluid sample (which may be a physiological sample) is provided. The method can be achieved by: depositing a fluid sample (which may be a physiological sample) on a biosensor (e.g. a test strip) having a reagent deposited thereon; applying signals to the sample and the reagent to transform the analyte into a different material; obtaining a physical characteristic of the sample; specifying a time point for sampling of signal output based on the obtained physical characteristic; measuring signal output at the specified sampling time; and determining an analyte concentration based on the measured signal output of the sample.

And for these aspects, the following features may also be utilized in various combinations with these previously disclosed aspects: the obtaining may include driving a second signal to the sample to derive a physical characteristic of the sample; the applying may include applying a first signal to the sample to derive a physical characteristic of the sample, and the applying of the first signal and the driving of the second signal may be in sequential order; the applying of the first signal may overlap with the driving of the second signal; the applying may comprise applying a first signal to the sample to derive a physical characteristic of the sample, and the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density; the directing may include driving first and second alternating signal at different respective frequencies in which a first frequency is lower than the second frequency; the first frequency may be at least one order of magnitude lower than the second frequency; the first frequency may include any frequency in the range of about 10 kHz to about 250 kHz, or about 10 kHz to about 90 kHz; and/or the specified sampling time may be calculated using an equation of the form:

$$\text{SpecifiedSamplingTime} = x_1 H^{x_2} + x_3$$

where
"SpecifiedSamplingTime" is designated as a time point from the start of the test sequence at which to sample the output signal (e.g. output signal) of the test strip,
H represents, or is physical characteristic of the sample;
$x_1$ is about 4.3e5, or is equal to 4.3e5, or is equal to 4.3e5+/−10%, 5% or 1% of the numerical value provided hereof;
$x_2$ is about −3.9, or is equal to −3.9, or is equal to −3.9+/−10%, 5% or 1% of the numerical value provided hereof; and
$x_3$ is about 4.8, or is equal to 4.8, or is equal to 4.8+/−10%, 5% or 1% of the numerical value provided herein.

Additionally, the calculating of the analyte concentration may include utilizing an equation of the form:

$$G_0 = \left[\frac{I_E - \text{Intercept}}{\text{Slope}}\right]$$

where
$G_0$ represents, or is, an analyte concentration
$I_E$ represents, or is, a signal (value or measurement; proportional to analyte concentration) measured at the SpecifiedSamplingTime, which may be the total signal measured at the SpecifiedSamplingTime;
Slope represents, or is, the value obtained from calibration testing of a batch of test strips of which this particular strip comes from; and
Intercept represents, or is, the value obtained from calibration testing of a batch of test strips of which this particular strip comes from.

In addition to the above, applicants have provided various embodiments of a technique to allow for improved glucose measurement using two somewhat related relationships: (a) a relationship between sampling time point and hematocrit to derive or calculate a specified sampling time at which a measurement of the output from the biosensor is to be taken; and (b) a relationship between batch slope and physical characteristic (e.g., hematocrit) that allows derivation of a new batch slope. Both relationships are utilized to determine a more accurate analyte concentration (i.e., based on the specified sampling time and the derived batch slope). This new technique does not rely on correction(s) or modification(s) to be made to an analyte measurement, thereby reducing test time while at the same time improving accuracy.

In an eleventh aspect of applicants' disclosure, a method of determining an analyte concentration from a fluid sample (which may be a physiological sample) with a biosensor is provided. The biosensor has at least two electrodes and a reagent disposed on at least one electrode of the electrodes. The method can be achieved by: depositing a fluid sample (which may be a physiological sample) on the at least two electrodes to start an analyte test sequence; applying a first signal to the sample to derive a physical characteristic of the sample; obtaining a physical characteristic of the sample; specifying a sampling time based on the physical characteristic from the obtaining step; deriving a batch slope for the biosensor based on the physical characteristic from the obtaining step; driving a second signal to the sample; and measuring an output signal at the specified sampling time from at least one electrode of the at least two electrodes; and calculating an analyte concentration based on the measured output signal at the specified sampling time and the derived batch slope.

And for these aspects, the following features may also be utilized in various combinations with these previously disclosed aspects: the applying of the first signal and the driving of the second signal may be in sequential order; the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density of the sample; the directing may include driving first and second alternating signal at different respective frequencies in which a first frequency is lower than the second frequency; the first frequency may be at least one order of magnitude lower than the second frequency; the first frequency may include any frequency in the range of about 10 kHz to about 250 kHz, or about 10 kHz to about 90 kHz; and/or the specified sampling time may be calculated using an equation of the form:

$$\text{SpecifiedSamplingTime} = x_1 H^{x_2} + x_3$$

where
"SpecifiedSamplingTime" is designated as a time point from the start of the test sequence at which to sample the output signal of the test strip,
H represents physical characteristic of the sample;
$x_1$ is about 4.3e5, or is equal to 4.3e5, or is equal to 4.3e5+/−10%, 5% or 1% of the numerical value provided hereof;
$x_2$ is about −3.9, or is equal to −3.9, or is equal to −3.9+/−10%, 5% or 1% of the numerical value provided hereof; and
$x_3$ is about 4.8, or is equal to 4.8, or is equal to 4.8+/−10%, 5% or 1% of the numerical value provided herein.

Additionally, for these aspects noted above, the derived slope may be determined from an equation of the form:

$$\text{NewSlope} = aH^2 + bH + c$$

where
H is a measured or estimated physical characteristic (e.g., hematocrit);

a represents about 1.4e−6, or is equal to 1.35e−6, or is equal to 1.4e−6+/−10%, 5% or 1% of the numerical value provided hereof;

b represents about −3.8e−4, or is equal to −3.79e−4, or is equal to −3.8e−4+/−10%, 5% or 1% of the numerical value provided hereof;

c represents about 3.6e−2, or is equal to 3.56e−2, or is equal to −3.6e−2+/−10%, 5% or 1% of the numerical value provided herein.

Furthermore, the calculating of the analyte concentration is computed with an equation of the form:

$$G_0 = \left[\frac{I_E - \text{Intercept}}{\text{NewSlope}}\right]$$

where $G_0$ represents, or is, an analyte concentration $I_E$ represents, or is, a signal (proportional to analyte concentration) measured at the SpecifiedSamplingTime, which may be the total signal measured at the SpecifiedSamplingTime;

NewSlope represents, or is, the value derived from the measured or estimated physical characteristic; and Intercept represents, or is, the value obtained from calibration testing of a batch of test strips of which this particular strip comes from.

In a twelfth aspect of applicants' disclosure, an analyte measurement system is provided that includes a test strip and an analyte meter. The test strip includes a substrate and a plurality of electrodes connected to respective electrode connectors. The analyte meter includes a housing, a test strip port connector configured to connect to the respective electrode connectors of the test strip, and a microprocessor in electrical communication with the test strip port connector to apply electrical signals or sense electrical signals from the plurality of electrodes during a test sequence. The microprocessor is configured to, during the test sequence: (a) apply a first signal to the plurality of electrodes so that a specified sampling time and a batch slope determined from a physical characteristic of a physiological fluid sample are derived, (b) apply a second signal to the plurality of electrodes, and (c) measure a signal output from one of the plurality of electrodes at the specified sampling time so that an analyte concentration is determined based on the measured signal at the specified time point and the batch slope.

And for these aspects, the following features may also be utilized in various combinations with these previously disclosed aspects: the plurality of electrodes may include at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; the at least two electrodes may comprise two electrodes to measure the physical characteristic and the analyte concentration; the plurality of electrodes may comprise two electrodes to measure the physical characteristic and the analyte concentration; all of the electrodes may be disposed on the same plane defined by the substrate; a reagent may be disposed proximate the at least two other electrodes and no reagent disposed on the at least two electrodes; and/or the specified sampling time may be calculated using an equation of the form:

SpecifiedSamplingTime=$x_1 H^{x_2}+x_3$ where

"SpecifiedSamplingTime" is designated as a time point from the start of the test sequence at which to sample the output signal of the test strip, H represents, or is, a physical characteristic of the sample;

$x_1$ is about 4.3e5, or is equal to 4.3e5, or is equal to 4.3e5+/−10%, 5% or 1% of the numerical value provided hereof;

$x_2$ is about −3.9, or is equal to −3.9, or is equal to −3.9+/−10%, 5% or 1% of the numerical value provided hereof; and $x_3$ is about 4.8, or is equal to 4.8, or is equal to 4.8+/−10%, 5% or 1% of the numerical value provided herein.

In these aspects previously noted above, the derived slope is determined from an equation of the form:

NewSlope=$aH^2+bH+c$ where

H is measured or estimated physical characteristic (e.g., hematocrit);

a represents about 1.4e−6, or is equal to 1.35e−6, or is equal to 1.4e−6+/−10%, 5% or 1% of the numerical value provided hereof;

b represents about −3.8e−4, or is equal to −3.79e−4, or is equal to −3.8e−4+/−10%, 5% or 1% of the numerical value provided hereof;

c represents about 3.6e−2, or is equal to 3.56e−2, or is equal to −3.6e−2+/−10%, 5% or 1% of the numerical value provided herein.

Furthermore, for these aspects, the calculating of the analyte concentration is computed with an equation of the form:

$$G_0 = \left[\frac{I_E - \text{Intercept}}{\text{NewSlope}}\right]$$

where $G_0$ represents, or is, an analyte concentration $I_E$ represents, or is, a signal (proportional to analyte concentration) measured at the SpecifiedSamplingTime, which may be the total signal measured at the SpecifiedSamplingTime;

NewSlope represents, or is, the value derived from the measured or estimated physical characteristic; and Intercept represents, or is, the value obtained from calibration testing of a batch of test strips of which this particular strip comes from.

In a thirteenth aspect of applicants' disclosure, an analyte measurement system is provided that includes a test strip and an analyte meter. The test strip includes a substrate and a plurality of electrodes connected to respective electrode connectors. The analyte meter includes a housing, a test strip port connector configured to connect to the respective electrode connectors of the test strip, and a microprocessor in electrical communication with the test strip port connector to apply electrical signals or sense electrical signals from the plurality of electrodes during a test sequence. The microprocessor is configured to, during a test sequence: (a) apply a first signal to the plurality of electrodes so that a specified sampling time and a batch slope of the test strip determined from a physical characteristic of a physiological fluid sample are derived, (b) apply a second signal to the plurality of electrodes, and (c) measure a signal output from one of the plurality of electrodes at the specified sampling time point so that an analyte concentration of the sample is determined based on the specified sampling time and batch slope within about 10 seconds of a start of the test sequence.

And for these aspects, the following features may also be utilized in various combinations with these previously disclosed aspects: the plurality of electrodes may include at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; the at least two electrodes may comprise two electrodes to measure the physical characteristic and the analyte concentration; the plurality of electrodes may comprise two electrodes to measure the physical characteristic and the analyte concentration; all of the electrodes may be disposed on the same plane defined by the substrate; a reagent may be disposed proximate the at least two other electrodes and no reagent disposed on the at least two electrodes; the specified sampling time may be calculated using an equation of the form:

$$\text{SpecifiedSamplingTime} = x_1 H^{x_2} + x_3$$

where
"SpecifiedSamplingTime" is designated as a time point from the start of the test sequence at which to sample the output signal of the test strip,
H represents, or is, a physical characteristic of the sample;
$x_1$ is about 4.3e5, or is equal to 4.3e5, or is equal to 4.3e5+/−10%, 5% or 1% of the numerical value provided hereof;
$x_2$ is about −3.9, or is equal to −3.9, or is equal to −3.9+/−10%, 5% or 1% of the numerical value provided hereof; and
$x_3$ is about 4.8, or is equal to 4.8, or is equal to 4.8+/−10%, 5% or 1% of the numerical value provided herein.

For these aspects previously noted, the derived slope may be determined from an equation of the form:

$$\text{NewSlope} = aH^2 + bH + c$$

where
NewSlope represents the derived slope;
H is measured or estimated physical characteristic (e.g., hematocrit);
a represents, or is, about 1.4e−6, or is equal to 1.35e−6, or is equal to 1.4e−6+/−10%, 5% or 1% of the numerical value provided hereof;
b represents, or is, about −3.8e−4, or is equal to −3.79e−4, or is equal to −3.8e−4+/−10%, 5% or 1% of the numerical value provided hereof;
c represents, or is, about 3.6e−2, or is equal to 3.56e−2, or is equal to −3.6e−2+/−10%, 5% or 1% of the numerical value provided hereof.

Furthermore, for these aspects, the calculating of the analyte concentration is computed with an equation of the form:

$$G_0 = \left[\frac{I_E - \text{Intercept}}{\text{NewSlope}}\right]$$

where
$G_0$ represents, or is, an analyte concentration
$I_E$ represents, or is, a signal (proportional to analyte concentration) measured at the SpecifiedSamplingTime, which may be the total signal measured at the SpecifiedSamplingTime;

NewSlope represents, or is, the value derived from the measured or estimated physical characteristic; and
Intercept represents, or is, the value obtained from calibration testing of a batch of test strips of which this particular strip comes from.

In a fourteenth aspect of applicants' disclosure, a method of demonstrating increased accuracy of a test strip is provided. The method can be achieved by: providing a batch of test strips; introducing a referential sample containing a referential concentration of an analyte to each of the batch of test strips to initiate a test sequence; reacting the analyte to cause a physical transformation of the analyte proximate the two electrodes (which may be between the two electrodes); determining a physical characteristic of the referential sample; deriving a batch slope of the batch of test strips based on the determined physical characteristic; sampling an electrical output of the referential sample at a specified time point during the test sequence defined by the measured or estimated physical characteristic; and calculating an analyte concentration based on the specified time point and the derived batch slope to provide for a final analyte concentration value for each of the batch of test strips such that at least 95% of the final analyte concentration values of the batch of test strips are within ±15% of the referential analyte concentration.

And for these aspects, the following features may also be utilized in various combinations with these previously disclosed aspects: the reacting may include driving a second signal to the sample and the determining may include applying a first signal to the sample to derive a physical characteristic of the sample, and the applying of the first signal and the driving of the second signal may be in sequential order; the applying of the first signal may overlap with the driving of the second signal; the reacting may comprise driving a second signal to the sample and the determining may comprise applying a first signal to the sample to derive a physical characteristic of the sample, and the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density; the directing may include driving first and second alternating signal at different respective frequencies in which a first frequency is lower than the second frequency; the first frequency may be at least one order of magnitude lower than the second frequency; the first frequency may include any frequency in the range of about 10 kHz to about 250 kHz, or about 10 kHz to about 90 kHz; and/or the specified sampling time may be calculated using an equation of the form:

$$\text{SpecifiedSamplingTime} = x_1 H^{x_2} + x_3$$

where
"SpecifiedSamplingTime" is designated as a time point from the start of the test sequence at which to sample the output signal of the test strip,
H represents, or is, a physical characteristic of the sample;
$x_1$ is about 4.3e5, or is equal to 4.3e5, or is equal to 4.3e5+/−10%, 5% or 1% of the numerical value provided hereof;

$x_2$ is about −3.9, or is equal to −3.9, or is equal to −3.9+/−10%, 5% or 1% of the numerical value provided hereof; and $x_3$ is about 4.8, or is equal to 4.8, or is equal to 4.8+/−10%, 5% or 1% of the numerical value provided hereof Additionally, for these previously disclosed aspects, the derived slope may be determined from an equation of the form:

$$\text{NewSlope} = aH^2 + bH + c$$

where

H is measured or estimated physical characteristic (e.g., hematocrit);

a represents, or is, about 1.4e−6, or is equal to 1.35e−6, or is equal to 1.4e−6+/−10%, 5% or 1% of the numerical value provided hereof;

b represents, or is, about −3.8e−4, or is equal to −3.79e−4, or is equal to −3.8e−4+/−10%, 5% or 1% of the numerical value provided hereof;

c represents, or is, about 3.6e−2, or is equal to 3.56e−2, or is equal to −3.6e−2+/−10%, 5% or 1% of the numerical value provided hereof.

Furthermore, for these aspects, the calculating of the analyte concentration is computed with an equation of the form:

$$G_0 = \left[\frac{I_E - \text{Intercept}}{\text{NewSlope}}\right]$$

where $G_0$ represents, or is, an analyte concentration $I_E$ represents, or is a signal (proportional to analyte concentration) or signals measured at the SpecifiedSamplingTime, which may be the total signal measured at the SpecifiedSamplingTime;

NewSlope represents, or is, the value derived from the measured or estimated physical characteristic; and Intercept represents, or is, the value obtained from calibration testing of a batch of test strips of which this particular strip comes from.

In a fifteenth aspect of applicants' disclosure, a method of determining an analyte concentration from a fluid sample (which may be a physiological sample). The method can be achieved by: depositing a fluid sample (which may be a physiological sample) on a biosensor having a reagent deposited thereon; applying signals to the sample and the reagent to transform the analyte into a different material; obtaining a physical characteristic of the sample; specifying a time point for sampling of signal output based on the physical characteristic from the obtaining step; deriving a batch slope of the biosensor; measuring signal output at the specified sampling time; and determining an analyte concentration based on the measured signal output of the sample at the specified sampling time and the derived batch slope.

And for these aspects, the following features may also be utilized in various combinations with these previously disclosed aspects: the obtaining may include driving a second signal to the sample to derive a physical characteristic of the sample; the applying may include applying a first signal to the sample to derive a physical characteristic of the sample, and the applying of the first signal and the driving of the second signal may be in sequential order; the applying of the first signal may overlap with the driving of the second signal; the applying may comprise applying a first signal to the sample to derive a physical characteristic of the sample, and the applying of the first signal may overlap with the driving of the second signal; the applying of the first signal may include directing an alternating signal to the sample so that a physical characteristic of the sample is determined from an output of the alternating signal; the applying of the first signal may include directing an optical signal to the sample so that a physical characteristic of the sample is determined from an output of the optical signal; the physical characteristic may include hematocrit and the analyte may include glucose; the physical characteristic may include at least one of viscosity, hematocrit, temperature and density; the directing may include driving first and second alternating signal at different respective frequencies in which a first frequency is lower than the second frequency; the first frequency may be at least one order of magnitude lower than the second frequency; the first frequency may include any frequency in the range of about 10 kHz to about 250 kHz, or about 10 kHz to about 90 kHz; and/or the specified sampling time may be calculated using an equation of the form:

$$\text{SpecifiedSamplingTime} = x_1 H^{x_2} + x_3$$

where

"SpecifiedSamplingTime" is designated as a time point from the start of the test sequence at which to sample the output signal of the test strip, H represents, or is, a physical characteristic of the sample;

$x_1$ is about 4.3e5, or is equal to 4.3e5, or is equal to 4.3e5+/−10%, 5% or 1% of the numerical value provided hereof;

$x_2$ is about −3.9, or is equal to −3.9, or is equal to −3.9+/−10%, 5% or 1% of the numerical value provided hereof; and $x_3$ is about 4.8, or is equal to 4.8, or is equal to 4.8+/−10%, 5% or 1% of the numerical value provided hereof.

For these aspects previously disclosed, the derived slope may be determined from an equation of the form:

$$\text{NewSlope} = aH^2 + bH + c$$

where

H is measured or estimated physical characteristic (e.g., hematocrit);

a represents, or is, about 1.4e−6, or is equal to 1.35e−6, or is equal to 1.4e−6+/−10%, 5% or 1% of the numerical value provided hereof;

b represents, or is, about −3.8e−4, or is equal to −3.79e−4, or is equal to −3.8e−4+/−10%, 5% or 1% of the numerical value provided hereof;

c represents, or is, about 3.6e−2, or is equal to 3.56e−2, or is equal to −3.6e−2+/−10%, 5% or 1% of the numerical value provided hereof.

Furthermore, the calculating of the analyte concentration is computed with an equation of the form:

$$G_0 = \left[\frac{I_E - \text{Intercept}}{\text{NewSlope}}\right]$$

where $G_0$ represents, or is, an analyte concentration $I_E$ represents, or is, a signal (proportional to analyte concentration) measured at the SpecifiedSamplingTime, which may be the total signal measured at the SpecifiedSamplingTime;

NewSlope represents, or is, the value derived from the measured or estimated physical characteristic; and Intercept represents, or is, the value obtained from calibration testing of a batch of test strips of which this particular strip comes from.

In a sixteenth aspect of applicants' disclosure, a method of determining an analyte concentration from a fluid sample (which may be a physiological sample) with a biosensor is provided. The biosensor has at least two electrodes and a reagent disposed on at least one of the electrodes. The method can be achieved by: depositing a fluid sample (which may be a physiological sample) on the at least two electrodes to start an analyte test sequence; applying a first signal to the sample to measure a physical characteristic of the sample; driving a second signal to the sample to cause an enzymatic reaction of the analyte and the reagent; estimating an analyte concentration based on a predetermined sampling time point from the start of the test sequence; selecting a sampling time point from a look-up table that includes a matrix in which different qualitative categories of the estimated analyte are set forth in the leftmost column of the matrix and different qualitative categories of the measured or estimated physical characteristic are set forth in the topmost row of the matrix and the sampling times are provided in the remaining cells of the matrix; measuring signal output from the sample at the selected sampling time point from the look-up table; calculating an analyte concentration from measured output signal sampled at said selected sampling time point in accordance with an equation of the form:

$$G_0 = \left[\frac{I_T - \text{Intercept}}{\text{Slope}}\right]$$

where $G_0$ represents, or is, an analyte concentration;

$I_T$ represents, or is, a signal (proportional to analyte concentration) measured at a specified sampling time T, which may be the total signal measured at the specified sampling time T;

Slope represents, or is the value obtained from calibration testing of a batch of test strips of which this particular strip comes from; and Intercept represents, or is, the value obtained from calibration testing of a batch of test strips of which this particular strip comes from.

In a seventeenth aspect of applicants' disclosure, a method of determining an analyte concentration from a fluid sample (which may be a physiological sample) with a biosensor is provided. The biosensor has at least two electrodes and a reagent disposed on at least one of the electrodes. The method can be achieved by: depositing a fluid sample (which may be a physiological sample) on the at least two electrodes to start an analyte test sequence; applying a first signal to the sample to measure or estimate a physical characteristic of the sample; driving a second signal to the sample to cause an enzymatic reaction of the analyte and the reagent; estimating an analyte concentration based on a predetermined sampling time point from the start of the test sequence; selecting a sampling time point from a look-up table that includes a matrix in which different qualitative categories of the estimated analyte are set forth in the leftmost column of the matrix and different qualitative categories of the measured or estimated physical characteristic are set forth in the topmost row of the matrix and the sampling times are provided in the remaining cells of the matrix; measuring signal output from the sample at the selected sampling time point; and calculating an analyte concentration from measured output signal sampled at said selected sampling time point.

And for these aspects, the following features may also be utilized in various combinations with these previously disclosed aspects: the applying of the first signal and the driving of the second signal may be sequential; the applying of the first signal may overlap with the driving of the second signal; the applying of the first signal may comprise directing an alternating signal to the sample so that a physical characteristic of the sample is determined from an output of the alternating signal; the physical characteristic may comprise hematocrit and the analyte may comprise glucose; the physical characteristic may comprise at least one of viscosity, hematocrit, temperature and density; the directing may comprise driving first and second alternating signals at different respective frequencies in which a first frequency is lower than the second frequency; the first frequency may be at least one order of magnitude lower than the second frequency; the first frequency may comprise any frequency in the range of about 10 kHz to about 250 kHz, or about 10 kHz to about 90 kHz; the measuring may comprise sampling the signal output continuously at the start of the test sequence until at least about 10 seconds after the start; which may further include the step of estimating an analyte concentration based on a measurement of the output signal at a predetermined time; the estimating may comprise comparing the estimated analyte concentration and the measured or estimated physical characteristic against a look-up table having different respective ranges of analyte concentration and physical characteristic of the sample indexed against different sample measurement times so that the point in time for measurement of the output from the sample of the second signal is obtained for the calculating step; and/or the calculating step may comprise utilizing an equation of the form:

$$G_0 = \left[\frac{I_T - \text{Intercept}}{\text{Slope}}\right]$$

where $G_0$ represents, or is, an analyte concentration;

$I_T$ represents, or is, a signal (proportional to analyte concentration) measured at a specified sampling time T, which may be the total signal measured at the specified sampling time T;

Slope represents, or is, the value obtained from calibration testing of a batch of test strips of which this particular strip comes from; and Intercept represents, or is, the value obtained from calibration testing of a batch of test strips of which this particular strip comes from.

In an eighteenth aspect of applicants' disclosure, an analyte measurement system is provided that includes a test strip and an analyte meter. The test strip includes a substrate and a plurality of electrodes connected to respective electrode connectors. The analyte meter includes a housing, a test strip port connector configured to connect to the respective electrode connectors of the test strip, and a microprocessor in electrical communication with the test strip port connector to apply electrical signals or sense electrical signals from the plurality of electrodes. The microprocessor is configured to: (a) apply a first signal to the plurality of electrodes so that a physical characteristic of a physiological fluid sample is determined; (b) estimate an analyte concentration based on a predetermined sampling time point during a test sequence; and (c) apply a second signal to the plurality of electrodes at a sampling time point during the test sequence dictated by the determined physical characteristic so that an analyte concentration is calculated from the second signal.

And for these aspects, the following features may also be utilized in various combinations with these previously disclosed aspects: the plurality of electrodes may comprise at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; all of the electrodes may be disposed on the same plane defined by the substrate; and/or a reagent may be disposed proximate the at least two other electrodes and no reagent disposed on the at least two electrodes.

In a nineteenth aspect of applicants' disclosure, an analyte measurement system is provided that includes a test strip and an analyte meter. The test strip includes a substrate and a plurality of electrodes connected to respective electrode connectors. The analyte meter includes a housing, a test strip port connector configured to connect to the respective electrode connectors of the test strip, and a microprocessor in electrical communication with the test strip port connector to apply electrical signals or sense electrical signals from the plurality of electrodes. The microprocessor is configured to: (a) apply a first signal to the plurality of electrodes so that a physical characteristic of a physiological fluid sample is determined during a test sequence; (b) estimate an analyte concentration based on a predetermined sampling time point during a test sequence; and (c) apply a second signal to the plurality of electrodes at a sampling time point during the test sequence dictated by the determined physical characteristic so that so that an analyte concentration is determined from the second signal within about 10 seconds of a start of the test sequence.

And for these aspects, the following features may also be utilized in various combinations with these previously disclosed aspects: the plurality of electrodes may comprise at least two electrodes to measure the physical characteristic and at least two other electrodes to measure the analyte concentration; the at least two electrodes and the at least two other electrodes may be disposed in the same chamber provided on the substrate; the at least two electrodes and the at least two other electrodes may be disposed in different chambers provided on the substrate; all of the electrodes may be disposed on the same plane defined by the substrate; and/or a reagent may be disposed proximate on the at least two other electrodes and no reagent disposed on the at least two electrodes.

In a twentieth aspect of applicants' disclosure, a method of demonstrating increased accuracy of a test strip is provided. The method can be achieved by: providing a batch of test strips; introducing a referential sample containing a referential concentration of an analyte to each test strip of the batch of test strips to start a test sequence; reacting the analyte with reagent disposed on each of the test strips to cause a physical transformation of the analyte proximate the two electrodes (which may be between the two electrodes); estimating an analyte concentration based on measured signal output of the sample at a predetermined time point from the start of the test sequence; determining a physical characteristic of the referential sample; sampling an electrical output of the referential sample at a dictated time point during the test sequence defined by the measured or estimated physical characteristic and the estimated analyte concentration; calculating an analyte concentration based on the dictated time point to provide for a final analyte concentration value for each test strip of the batch of test strips such that at least 95% of the final analyte concentration values of the batch of test strips are within ±10% of the referential analyte concentration for a range of hematocrit of the sample from about 30% to about 55%.

And for these aspects, the following features may also be utilized in various combinations with these previously disclosed aspects: the determining may comprise applying a first signal to the sample to measure a physical characteristic of the sample; the reacting may comprise driving a second signal to the sample; the applying of the first signal and the driving of the second signal may be sequential; the applying of the first signal may overlap with the driving of the second signal; the applying of the first signal may comprise directing an alternating signal to the sample so that a physical characteristic of the sample is determined from an output of the alternating signal; the applying of the first signal may comprise directing an electromagnetic signal to the sample so that a physical characteristic of the sample is determined from an output of the electromagnetic signal; the physical characteristic may comprise hematocrit and the analyte may comprise glucose; the physical characteristic may comprise at least one of viscosity, hematocrit, temperature and density; the directing may comprise driving first and second alternating signals at different respective frequencies in which a first frequency is lower than the second frequency; the first frequency may be at least one order of magnitude lower than the second frequency; the first frequency may comprise any frequency in the range of about 10 kHz to about 250 kHz, or about 10 kHz to about 90 kHz; and/or the measuring may comprise sampling the signal output continuously at the start of the test sequence until at least about 10 seconds after the start; which may further include the step of estimating an analyte concentration based on a measurement of the output signal at a predetermined time; the estimating may comprise comparing the estimated analyte concentration and the measured or estimated physical characteristic against a look-up table having different respective ranges of analyte concentration and physical characteristic of the sample indexed against different sample measurement times so that the point in time for measurement of the output from the sample of the second signal is obtained for the calculating step.

In a twenty-first aspect of applicants' disclosure, a method of determining an analyte concentration from a fluid sample (which may be a physiological sample) is provided. The method can be achieved by: depositing a fluid sample (which may be a physiological sample) on a biosensor to start a test sequence; causing the analyte in the sample to undergo an enzymatic reaction; estimating an analyte concentration in the sample; measuring at least one physical characteristic of the sample; defining a time point from the start of the test sequence to sample output signals of the biosensor based on the estimated analyte concentration and at least one physical characteristic from the measuring step; sampling output signals of the biosensor at the defined time point; determining an analyte concentration from sampled signals at the defined time point.

And for these aspects, the following features may also be utilized in various combinations with these previously disclosed aspects: the measuring may comprise applying a first signal to the sample to measure a physical characteristic of the sample; the causing step may comprise driving a second signal to the sample; the measuring may comprise evaluating an output signal from the at least two electrodes at a point in time after the start of the test sequence, in which the point in time is set as a function of at least the measured or estimated physical characteristic; the determining step may comprise calculating an analyte concentration from the measured output signal at said point in time; the applying of the first signal and the driving of the second signal may be sequential; the applying of the first signal may overlap with the driving of the second signal; the applying of the first signal may comprise directing an alternating signal to the sample so that a physical characteristic of the sample is determined from an output of the alternating signal; which may further include the step of estimating an analyte concentration based on a predetermined sampling time point from the start of the test sequence; the defining may comprise selecting a defined time point based on both the measured or estimated physical characteristic and the estimated analyte concentration; the physical characteristic may comprise hematocrit and the analyte may comprise glucose; the physical characteristic may comprise at least one of viscosity, hematocrit, temperature and density; the directing may comprise driving first and second alternating signal at different respective frequencies in which a first frequency is lower than the second frequency; the first frequency may be at least one order of magnitude lower than the second frequency; the first frequency may comprise any frequency in the range of about 10 kHz to about 250 kHz, or about 10 kHz to about 90 kHz; the measuring may comprise sampling the signal output continuously at the start of the test sequence until at least about 10 seconds after the start; which may further include the step of estimating an analyte concentration based on a measurement of the output signal at a predetermined time; and/or the estimating may comprise comparing the estimated analyte concentration and the measured or estimated physical characteristic against a look-up table having different respective ranges of analyte concentration and physical characteristic of the sample indexed against different sample measurement times so that the point in time for measurement of the output from the sample of the second signal is obtained for the calculating step.

In the sixteenth to the twenty-first aspects, the sampling time point could be selected from a look-up table that includes a matrix in which different qualitative categories of the estimated analyte are set forth in the leftmost column of the matrix and different qualitative categories of the measured or estimated physical characteristic are set forth in the topmost row of the matrix and the sampling times are provided in the remaining cells of the matrix. In any of the above aspects, the fluid sample may be blood. In any of the above aspects, the physical characteristic may include at least one of viscosity, hematocrit, or density of the sample, or the physical characteristic may be hematocrit, wherein, optionally, the hematocrit level is between 30% and 55%. In any of the above aspects, where H represents, or is, the physical characteristic of the sample, it may be the measured, estimated or determined hematocrit, or may be in the form of hematocrit. In any of the above aspects, the physical characteristic may be determined from a measured characteristic, such as the impedance or phase angle of the sample. In any of the above aspects, the signal represented by $I_E$ and/or $I_T$ may be current.

In the aforementioned aspects of the disclosure, the steps of determining, estimating, calculating, computing, deriving and/or utilizing (possibly in conjunction with an equation) may be performed by an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as test meters or analyte testing devices, each device or meter comprising an electronic circuit or processor configured to perform the steps of any one of the aforementioned methods.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 3A(1) illustrates the test strip 100 of the system of FIG. 1 in which there are two physical characteristic sensing electrodes upstream of the measurement electrodes.

FIG. 3A(2) illustrates a variation of the test strip of FIG. 3A(1) in which a shielding or grounding electrode is provided for proximate the entrance of the test chamber;

FIG. 3A(3) illustrates a variation of the test strip of FIG. 3A(2) in which a reagent area has been extended upstream to cover at least one of the physical characteristic sensing electrodes;

FIG. 3A(4) illustrates a variation of test strip 100 of FIGS. 3A(1), 3A(2) and 3A(3) in which certain components of the test strip have been integrated together into a single unit;

FIG. 6A1 illustrates a logic diagram of an exemplary method to achieve a more accurate analyte determination.

FIG. 6A2 illustrates one relationship between batch slope and physical characteristic (e.g., hematocrit).

FIG. 6A3 illustrates data from test measurements conducted with the exemplary technique herein such that the data show the bias of less than ±15% for the hematocrit range of about 30% to about 55%.

FIG. 6B1 illustrates a logic diagram of an exemplary method to achieve a more accurate analyte determination.

FIG. 6B2 illustrates one relationship between sampling time point and hematocrits.

FIG. 6B3 illustrates data from test measurements conducted with the exemplary technique herein such that the data show the bias of less than ±25% for the hematocrit range of about 30% to about 55%.

FIG. 6C1 illustrates a logic diagram of an exemplary method to achieve a more accurate analyte determination.

FIG. 6C2 illustrates one relationship between sampling time point and hematocrits.

FIG. 6C3 illustrates a relationship between slope and hematocrits.

FIG. 6C4 illustrates data from test measurements conducted with the exemplary technique herein such that the data show the bias of less than ±25% for the hematocrit range of about 30% to about 55%.

FIG. 6D1 illustrates a logic diagram of an exemplary method to achieve a more accurate analyte determination.

FIG. 6D2 illustrates a signal output transient of the biosensor and the range of time point utilized for determination of the analyte, as well as the estimation of the analyte concentration.

FIG. 6D3 illustrates data from test measurements conducted with the exemplary technique herein such that the data show the bias of less than about ±10% for the hematocrit range of about 30% to about 55%.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably.

Figure 1:
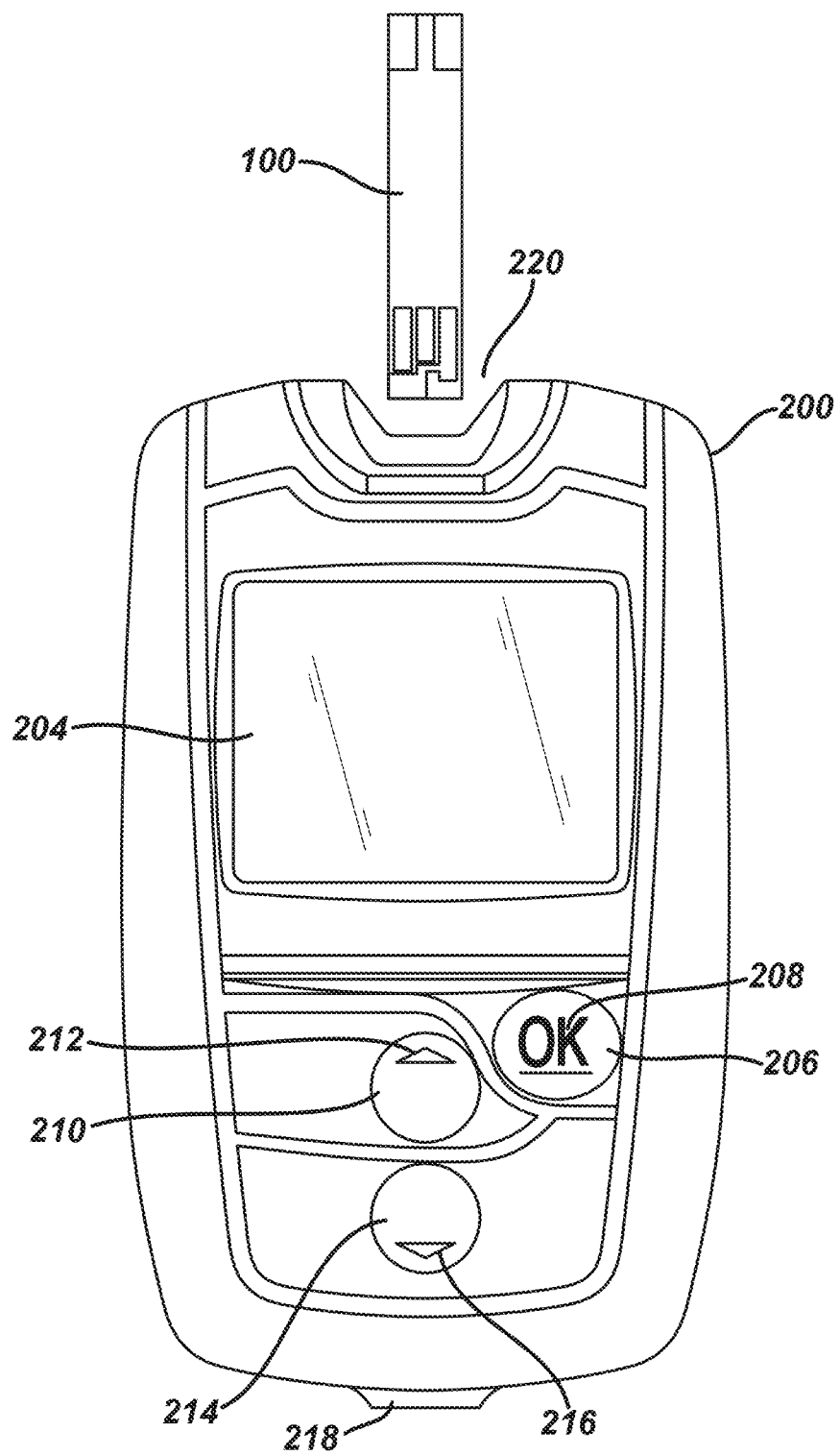
FIG. 1 illustrates an analyte measurement system.

FIG. 1 illustrates a test meter 200, for testing analyte (e.g., glucose) levels in the blood of an individual with a test strip produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 (or its variants 400, 500, or 600) into a strip port connector 220, by pressing and briefly holding first user interface input 206, or by the detection of data traffic across a data port 218. Test meter 200 can be switched off by removing test strip 100 (or its variants 400, 500, or 600), pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2A:
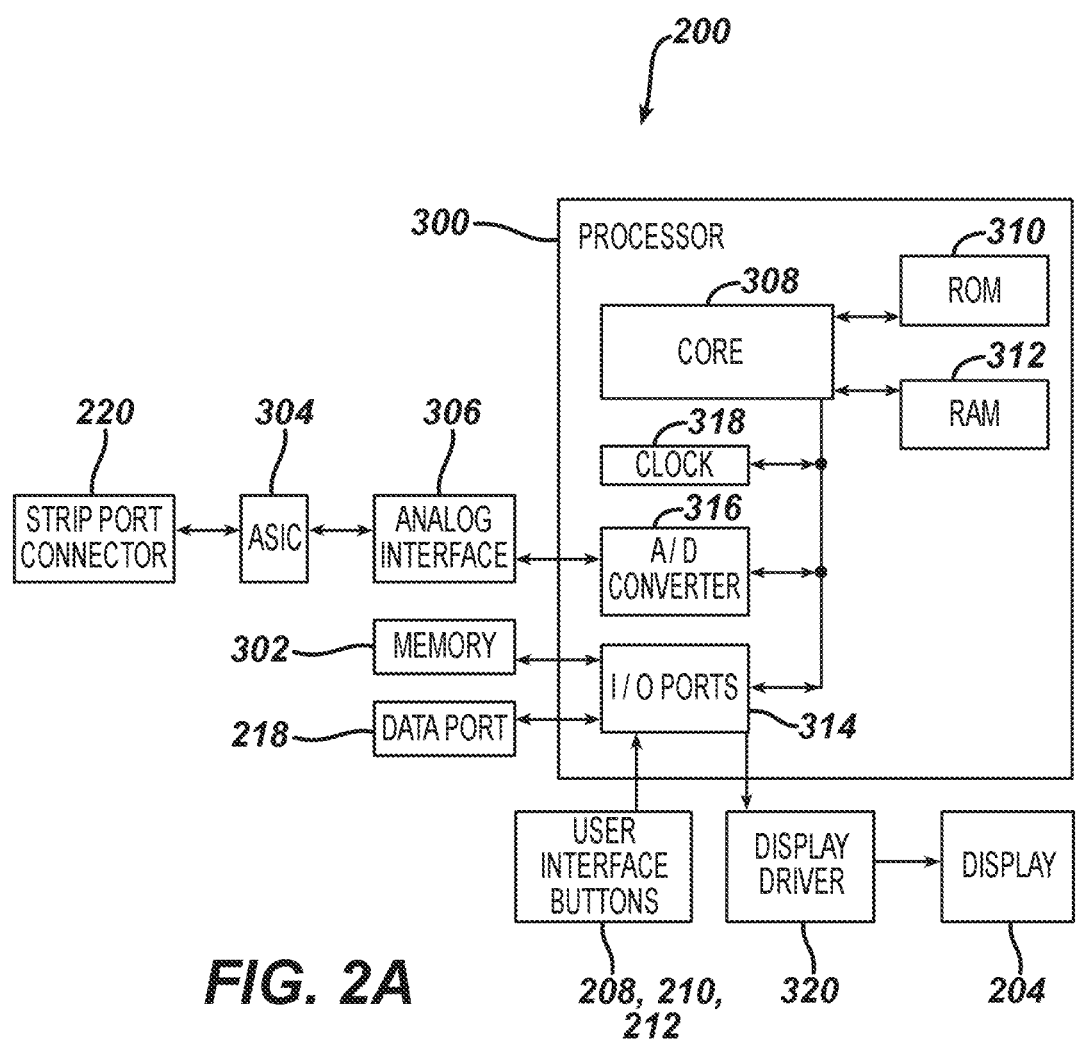
FIG. 2A illustrates in simplified schematic form the components of the meter 200.

Referring to FIG. 2A, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 (or its variants 400, 500, or 600) inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit. Detailed descriptions and illustrations of the meter 200 are shown and described in International Patent Application Publication No. WO2006070200, which is hereby incorporated by reference into this application as if fully set forth herein.

FIG. 3A(1) is an exemplary exploded perspective view of a test strip 100, which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100. Test strip 100 may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A(1).

Test strip 100 may include a sample-receiving chamber 92 through which a physiological fluid sample 95 may be drawn through or deposited (FIG. 3A(2)). The physiological fluid sample discussed herein may be blood. Sample-receiving chamber 92 can include an inlet at a proximal end and an outlet at the side edges of test strip 100, as illustrated in FIG. 3A(1). A fluid sample 95 can be applied to the inlet along axis L-L (FIG. 3A(2)) to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A(1). A bottom portion or "floor" of sample-receiving chamber 92 may include a portion of substrate 5, conductive layer 50, and insulation layer 16, as illustrated in FIG. 3A(1). A top portion or "roof" of sample-receiving chamber 92 may include distal hydrophilic portion 32, as illustrated in FIG. 3A(1). For test strip 100, as illustrated in FIG. 3A(1), substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A(1), first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100 has been properly inserted by measuring a continuity between reference contact pad 11 and strip detection bar 17, as illustrated in FIG. 3A(1).

Figure 3B:
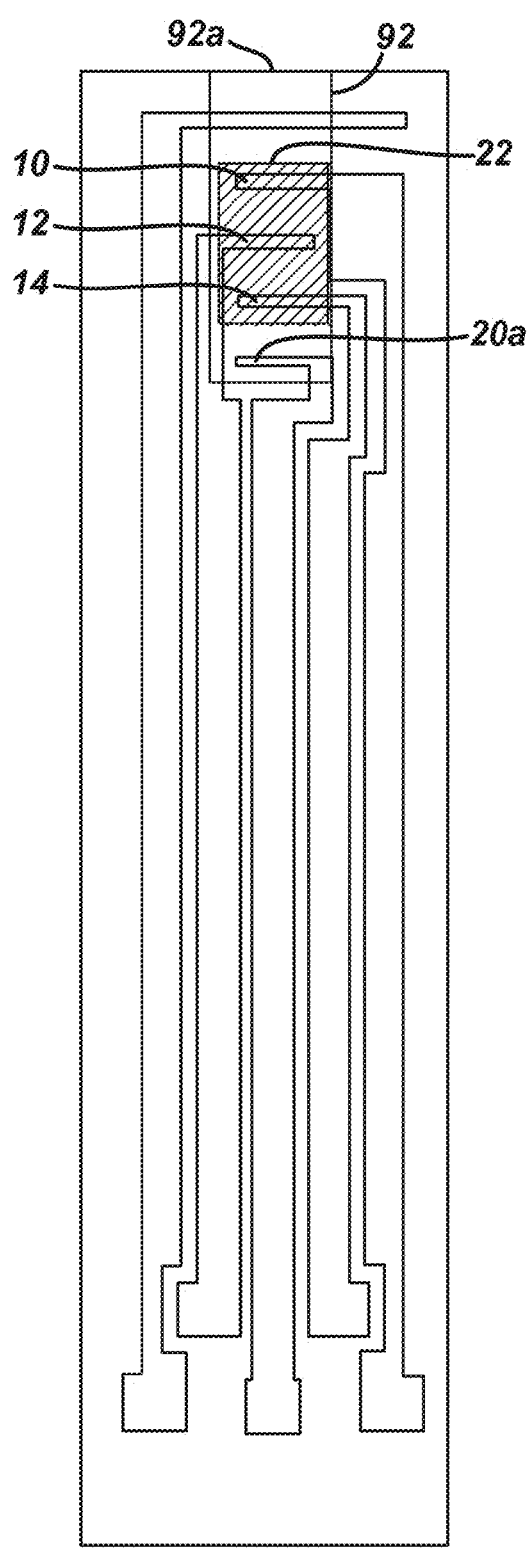
FIG. 3B illustrates a variation of the test strip of FIG. 3A(1), 3A(2), or 3A(3) in which one physical characteristic sensing electrode is disposed proximate the entrance and the other physical characteristic sensing electrode is at the terminal end of the test cell with the measurement electrodes disposed between the pair of physical characteristic sensing electrodes.
Figure 3C:
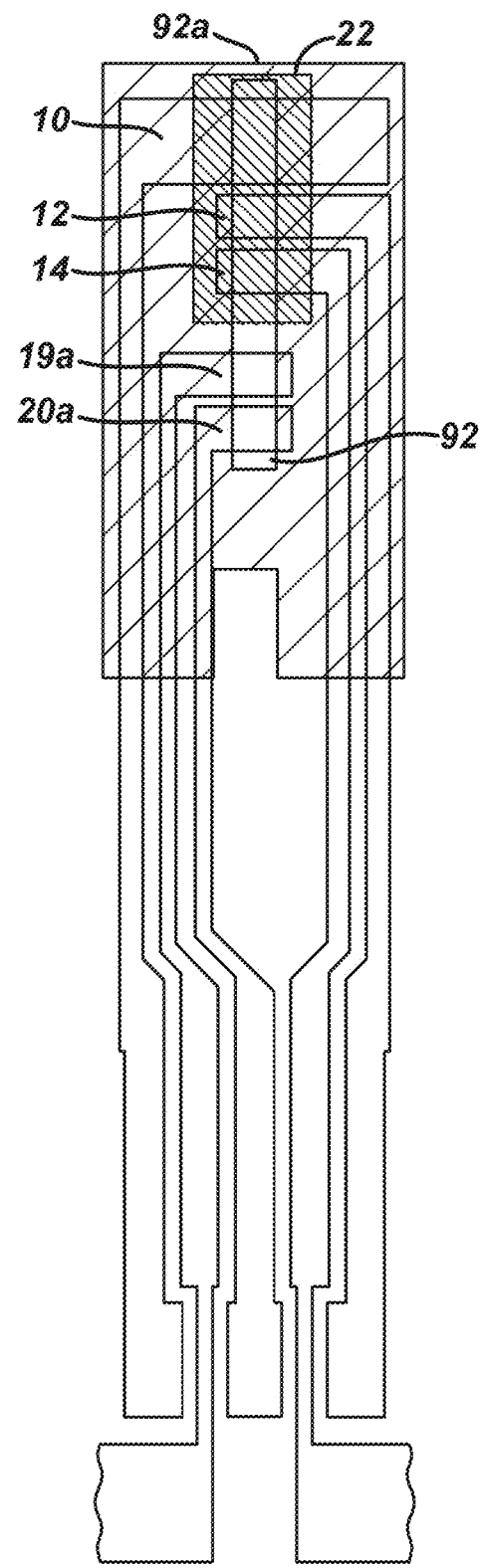
FIGS. 3C and 3D illustrate variations of FIG. 3A(1), 3A(2), or 3A(3) in which the physical characteristic sensing electrodes are disposed next to each other at the terminal end of the test chamber with the measurement electrodes upstream of the physical characteristic sensing electrodes.
Figure 3D:
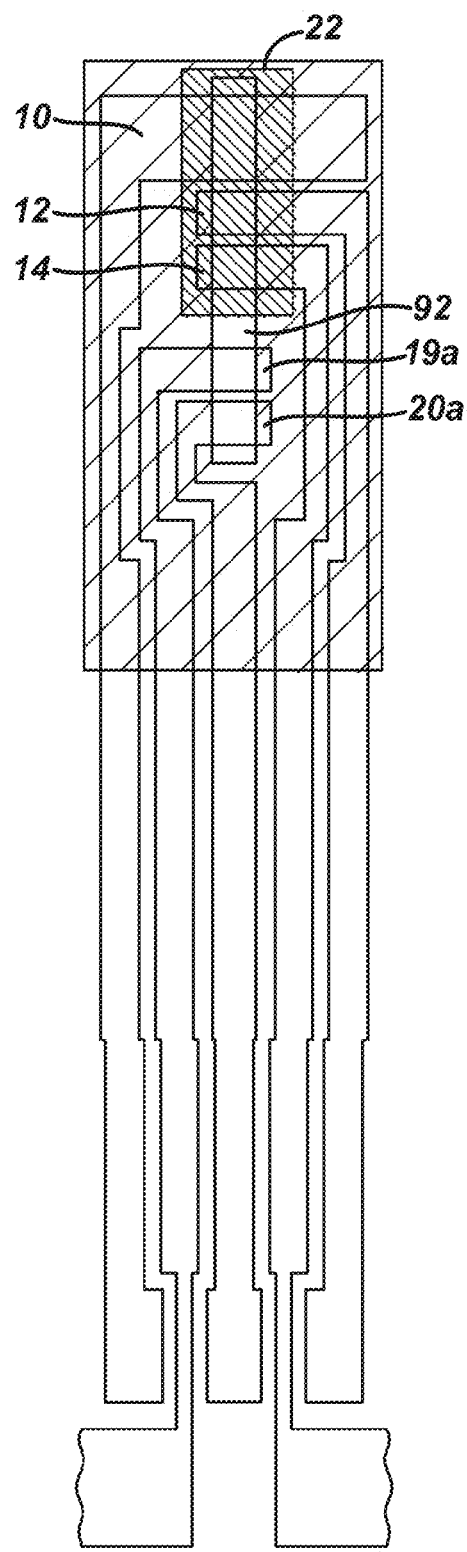
Figure 3E:
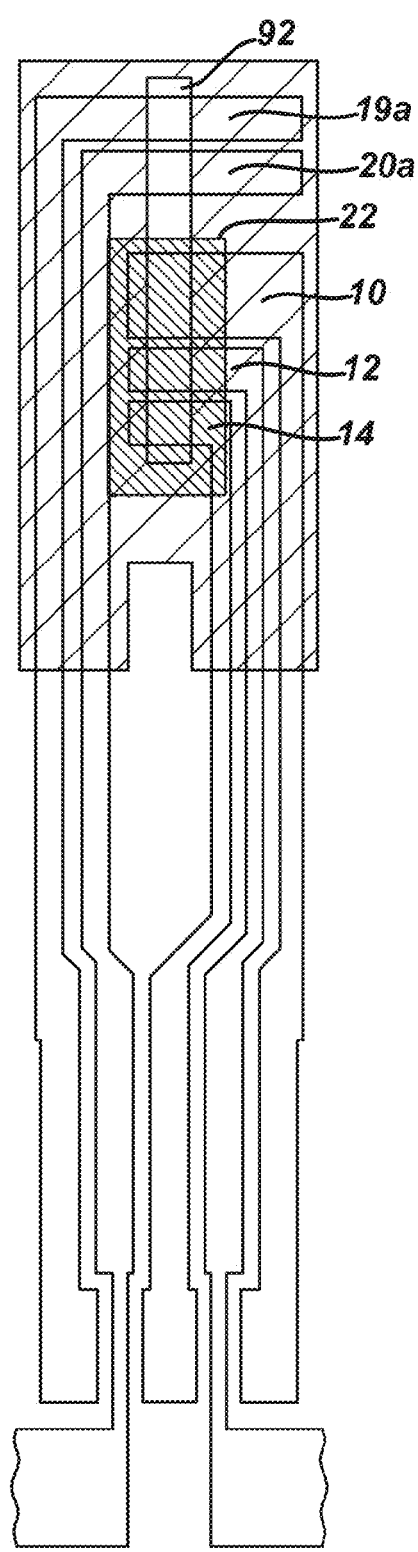
FIGS. 3E and 3F illustrates a physical characteristic sensing electrodes arrangement similar to that of FIG. 3A(1), 3A(2), or 3A(3) in which the pair of physical characteristic sensing electrodes are proximate the entrance of the test chamber.
Figure 3F:
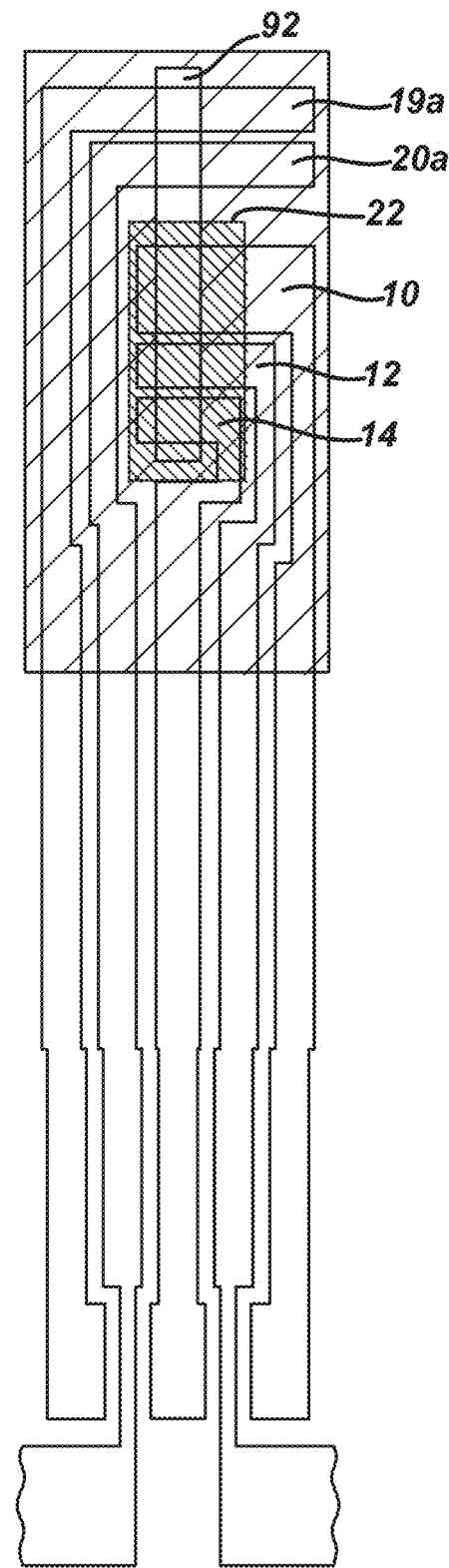
Figure 3G:
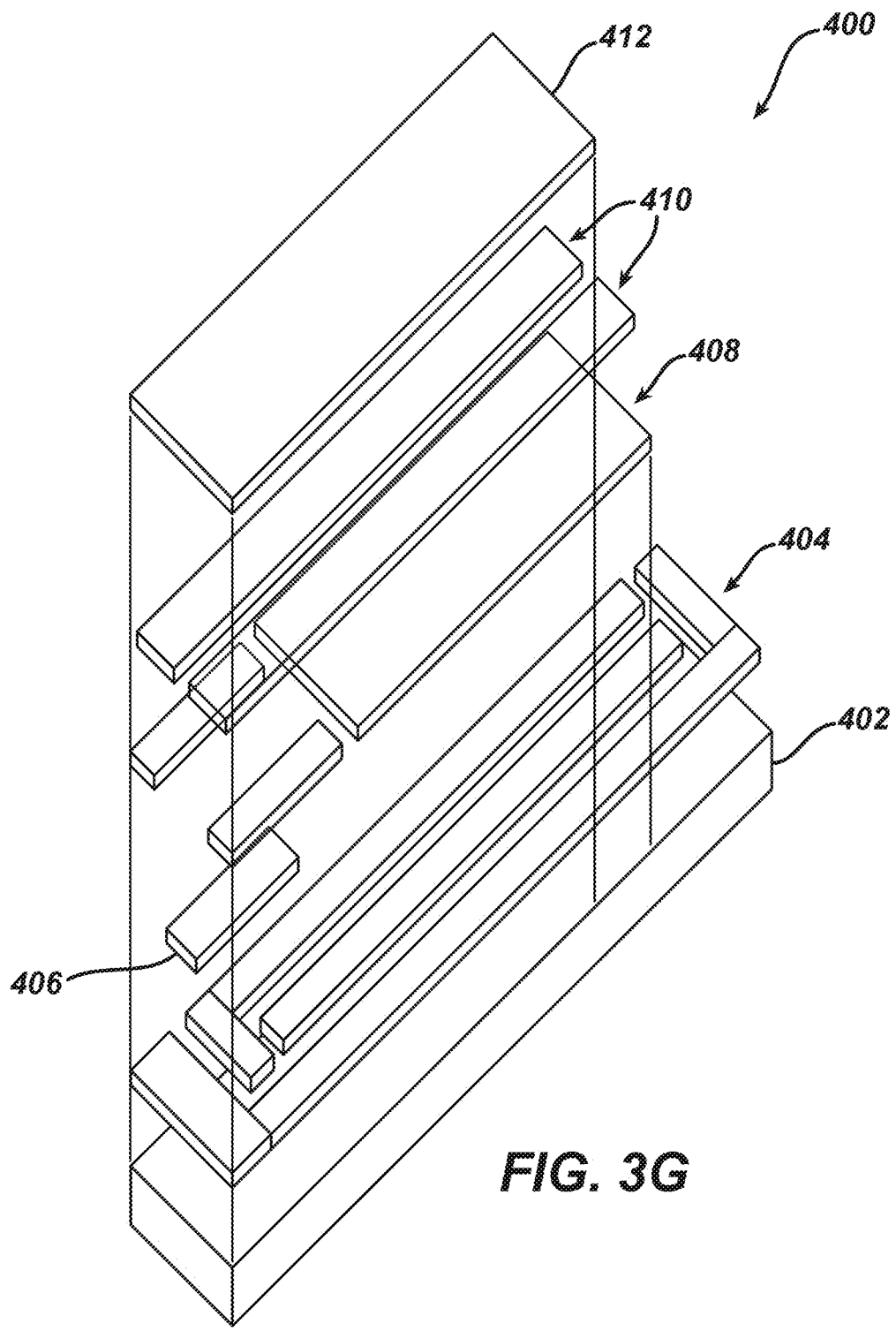
FIG. 3G is a simplified, perspective, exploded view of an analytical test strip according to an embodiment of the present disclosure.
Figure 3H:
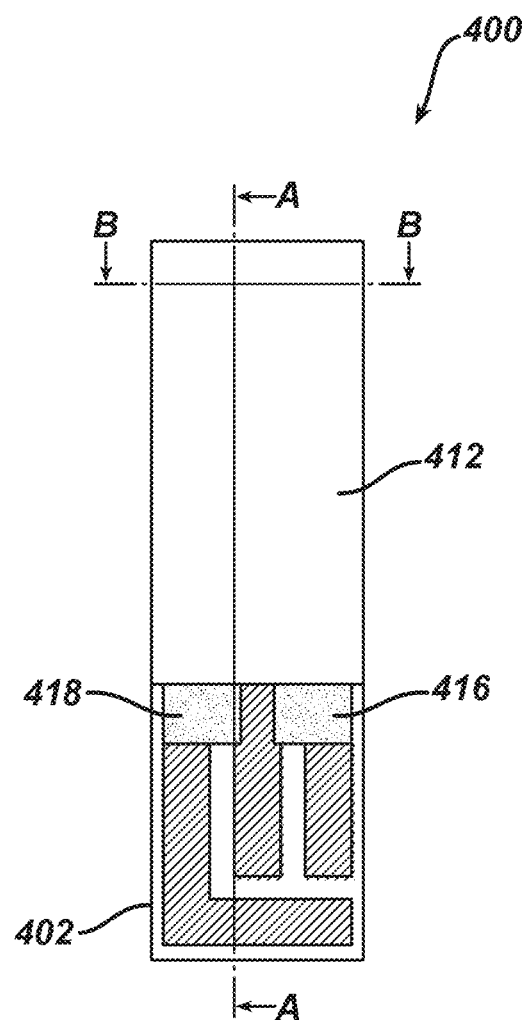
FIG. 3H is a simplified top view of the analytical test strip of FIG. 3G.
Figure 3I:
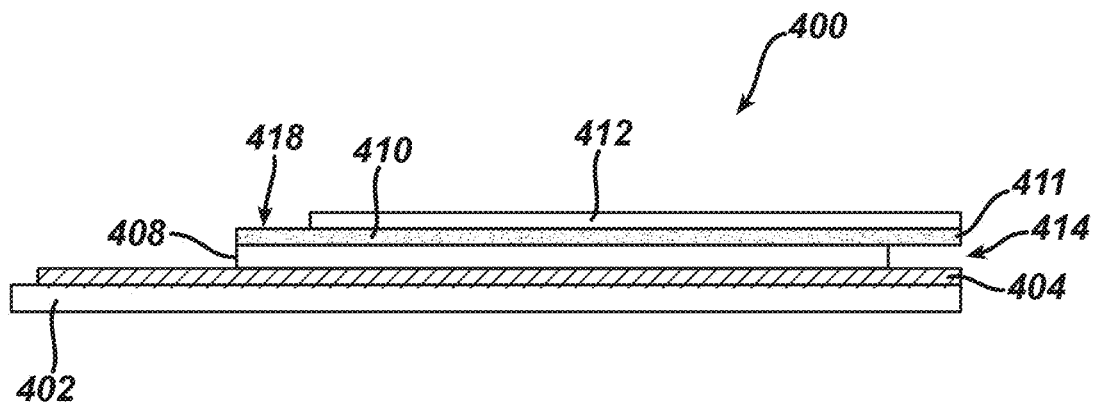
FIG. 3I is a simplified cross-sectional side view of the analytical test strip of FIG. 3H taken along line A-A of FIG. 3H.
Figure 3J:
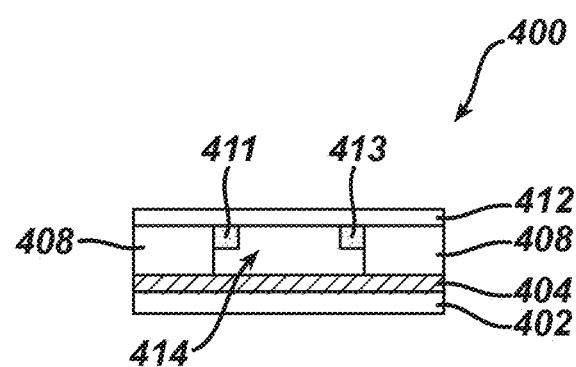
FIG. 3J is a simplified cross-sectional end view of the analytical test strip of FIG. 3H taken along line B-B of FIG. 3H.
Figure 3K:
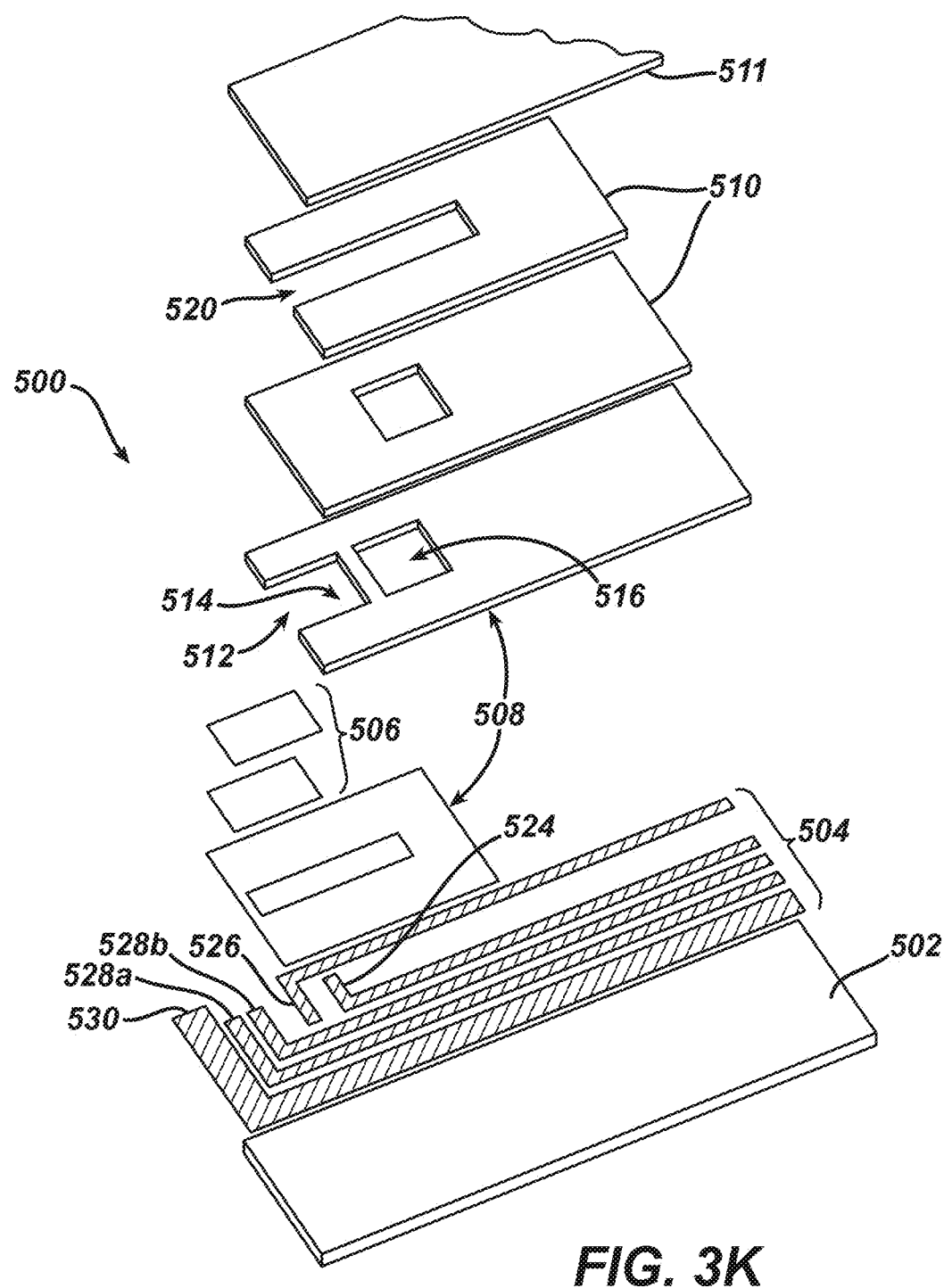
FIG. 3K is a simplified, perspective exploded view of an analytical test strip according to an embodiment of the present disclosure.
Figure 3L:
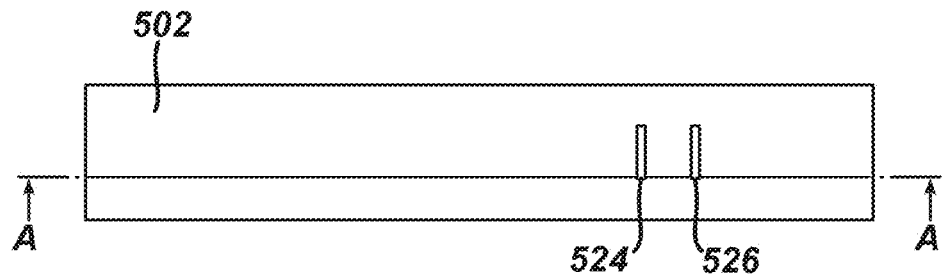
FIG. 3L is a simplified top view of the electrically-insulating substrate and a portion of a first patterned conductor layer of an analytical test strip of FIG. 3K.
Figure 3M:
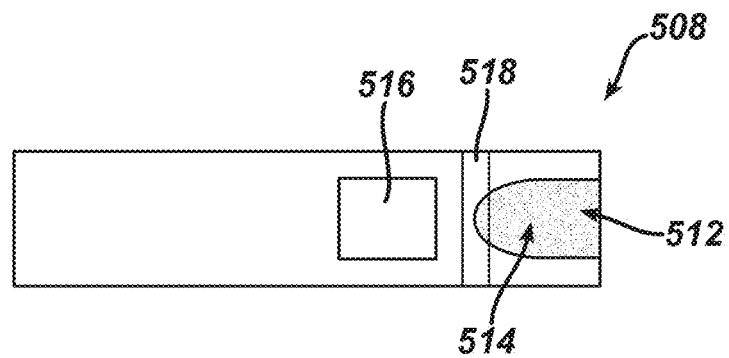
FIG. 3M is a simplified top view of the first patterned spacer layer of the analytical test strip of FIG. 3K.
Figure 3N:
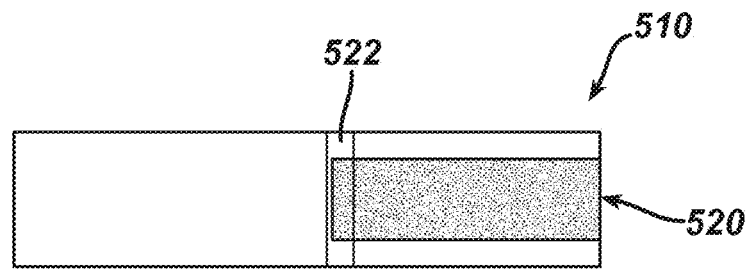
FIG. 3N is a simplified top view of the second patterned spacer layer of the analytical test strip of FIG. 3K.
Figure 3O:
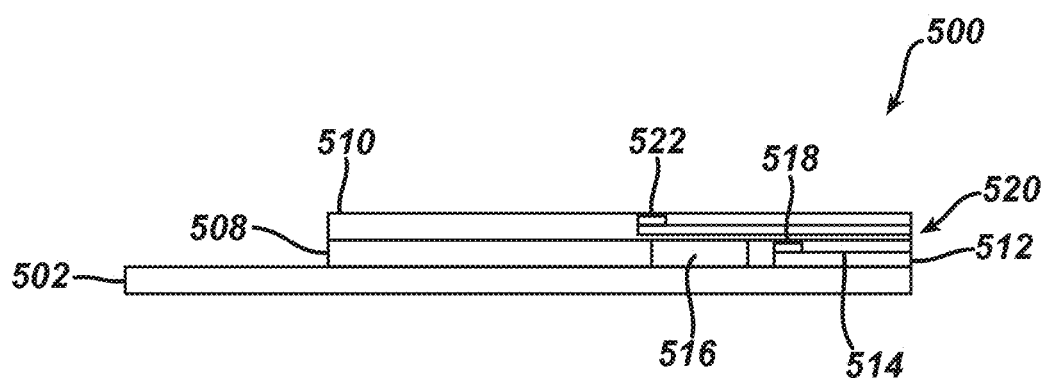
FIG. 3O is a simplified cross-sectional side view of the analytical test strip of FIG. 3K taken along line A-A of FIG. 2A.
Figure 3P:
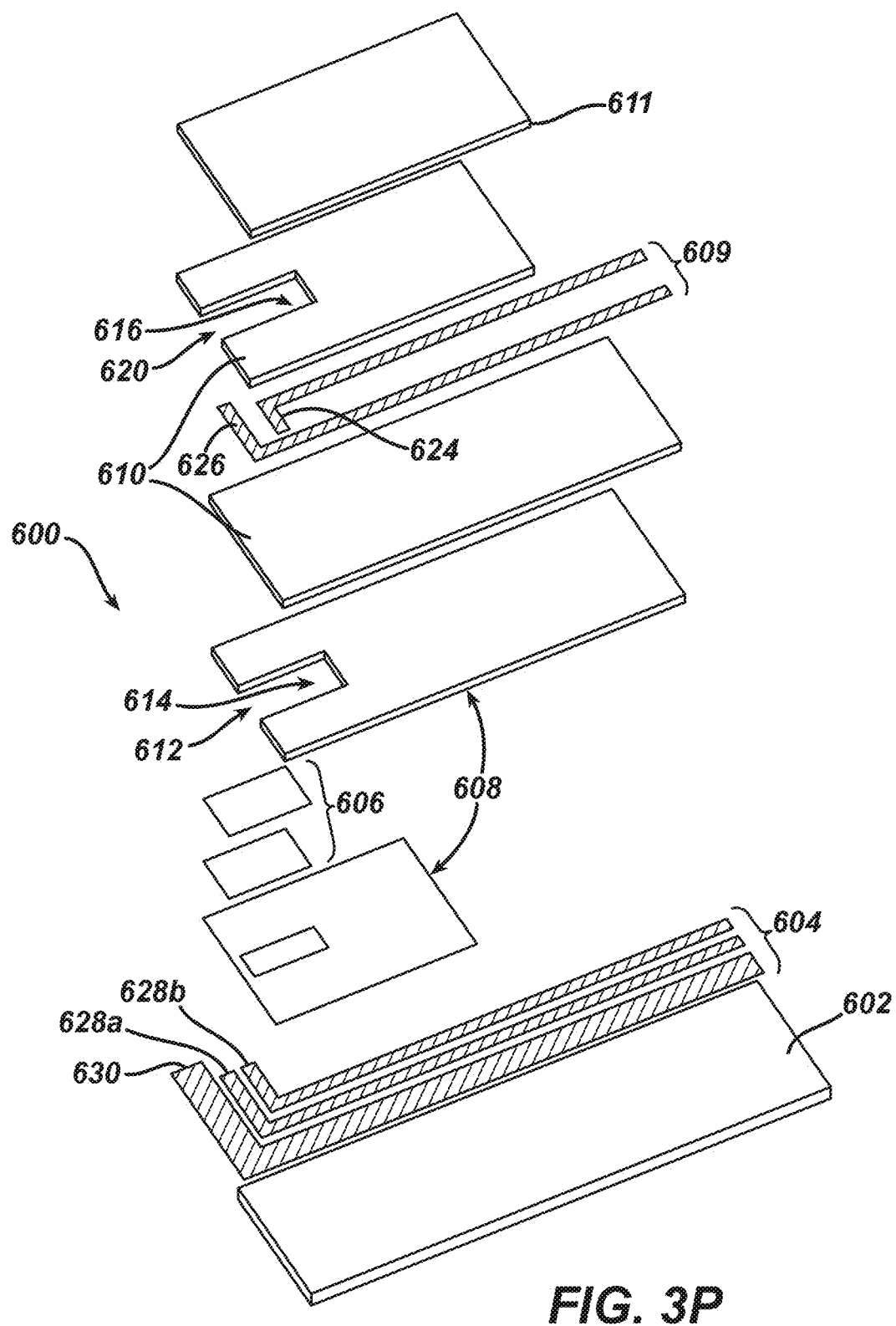
FIG. 3P is a simplified, perspective exploded view of an analytical test strip according to another embodiment of the present disclosure.
Figure 3Q:
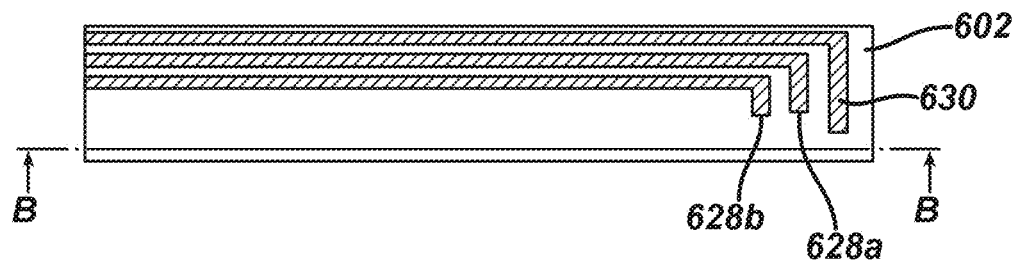
FIG. 3Q is a simplified top view of the electrically insulating substrate and first patterned conductor layer of the analytical test strip of FIG. 3P.
Figure 3R:
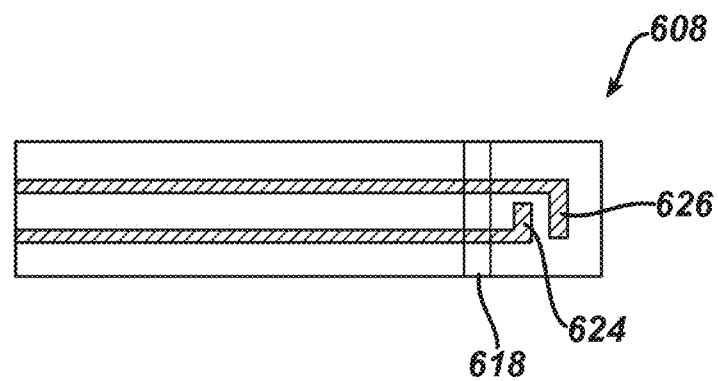
FIG. 3R is a simplified top view of a portion of a second patterned spacer layer and second patterned conductor layer of the analytical test strip of FIG. 3P.
Figure 3S:
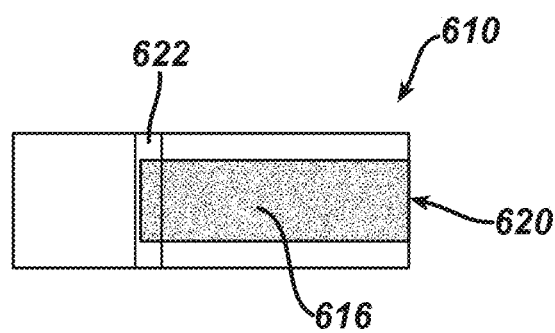
FIG. 3S is a simplified top view of a third patterned spacer layer of the analytical test strip of FIG. 3P.
Figure 3T:
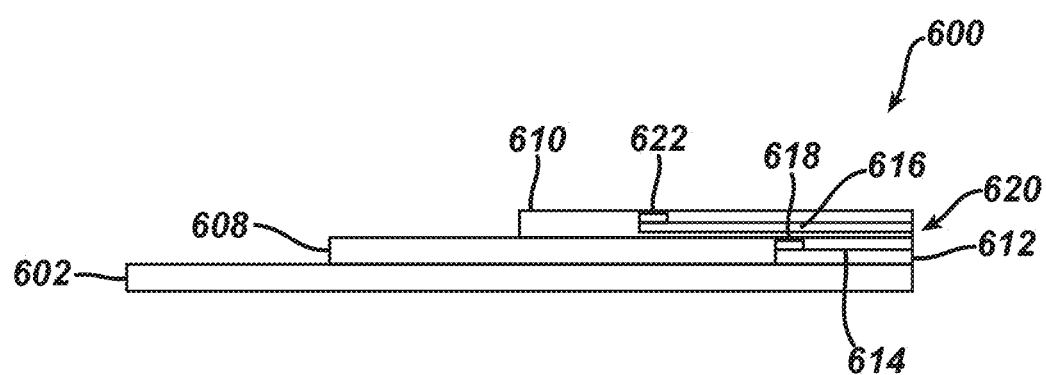
FIG. 3T is a simplified cross-sectional side view of the analytical test strip of FIG. 3P taken along line B-B of FIG. 3Q.

Variations of the test strip 100 (FIG. 3A(1), 3A(2), 3A(3), or 3A(4)) are shown in FIGS. 3B-3T. Briefly, with regard to variations of test strip 100 (illustrated exemplarily in FIGS. 3A(2), 3A(2) and 3B through 3T), these test strips include an enzymatic reagent layer disposed on the working electrode, a patterned spacer layer disposed over the first patterned conductive layer and configured to define a sample chamber within the analytical test strip, and a second patterned conductive layer disposed above the first patterned conductive layer. The second patterned conductive layer includes a first phase-shift measurement electrode and a second phase-shift measurement electrode. Moreover, the first and second phase-shift measurement electrodes are disposed in the sample chamber and are configured to measure, along with the hand-held test meter, a phase shift of an electrical signal forced through a bodily fluid sample introduced into the sample chamber during use of the analytical test strip. Such phase-shift measurement electrodes are also referred to herein as bodily fluid phase-shift measurement electrodes. Analytical test strips of various embodiments described herein are believed to be advantageous in that, for example, the first and second phase-shift measurement electrodes are disposed above the working and reference electrodes, thus enabling a sample chamber of advantageously low volume. This is in contrast to a configuration wherein the first and second phase-shift measurement electrodes are disposed in a co-planar relationship with the working and reference electrodes thus requiring a larger bodily fluid sample volume and sample chamber to enable the bodily fluid sample to cover the first and second phase-shift measurement electrodes as well as the working and reference electrodes.

In the embodiment of FIG. 3A(2) which is a variation of the test strip of FIG. 3A(1), an additional electrode 10a is provided as an extension of any of the plurality of electrodes 19a, 20a, 14, 12, and 10. It must be noted that the built-in shielding or grounding electrode 10a is used to reduce or eliminate any capacitance coupling between the finger or body of the user and the characteristic measurement electrodes 19a and 20a. The grounding electrode 10a allows for any capacitance to be directed away from the sensing electrodes 19a and 20a. To do this, the grounding electrode 10a can be connected any one of the other five electrodes or to its own separate contact pad (and track) for connection to ground on the meter instead of one or more of contact pads 15, 17, 13 via respective tracks 7, 8, and 9. In a preferred embodiment, the grounding electrode 10a is connected to one of the three electrodes that has reagent 22 disposed thereon. In a most preferred embodiment, the grounding electrode 10a is connected to electrode 10. Being the grounding electrode, it is advantageous to connect the grounding electrode to the reference electrode (10) so not to contribute any additional current to the working electrode measurements which may come from background interfering compounds in the sample. Further by connecting the shield or grounding electrode 10a to electrode 10 this is believed to effectively increase the size of the counter electrode 10 which can become limiting especially at high signals. In the embodiment of FIG. 3A(2), the reagent are arranged so that they are not in contact with the measurement electrodes 19a and 20a. Alternatively, in the embodiment of FIG. 3A(3), the reagent 22 is arranged so that the reagent 22 contacts at least one of the sensing electrodes 19a and 20a.

In alternate version of test strip 100, shown here in FIG. 3A(4), the top layer 38, hydrophilic film layer 34 and spacer 29 have been combined together to form an integrated assembly for mounting to the substrate 5 with reagent layer 22' disposed proximate insulation layer 16'.

In the embodiment of FIG. 3B, the analyte measurement electrodes 10, 12, and 14 are disposed in generally the same configuration as in FIG. 3A(1), 3A(2), or 3A(3). The electrodes 19a and 20a to sense physical characteristic (e.g., hematocrit) level, however, are disposed in a spaced apart configuration in which one electrode 19a is proximate an entrance 92a to the test chamber 92 and another electrode 20a is at the opposite end of the test chamber 92. Electrodes 10, 12, and 14 are disposed to be in contact with a reagent layer 22.

In FIGS. 3C, 3D, 3E and 3F, the physical characteristic (e.g., hematocrit) sensing electrodes 19a and 20a are disposed adjacent each other and may be placed at the opposite end 92b of the entrance 92a to the test chamber 92 (FIGS. 3C and 3D) or adjacent the entrance 92a (FIGS. 3E and 3F). In all of these embodiments, the physical characteristic sensing electrodes are spaced apart from the reagent layer 22 so that these physical characteristic sensing electrodes are not impacted by the electrochemical reaction of the reagent in the presence of a fluid sample (e.g., blood or interstitial fluid) containing glucose.

Referring to FIGS. 3G through 3J, electrochemical-based analytical test strip 400 includes an electrically-insulating substrate layer 402, a first patterned conductive layer 404 disposed on the electrically-insulating substrate layer, an enzymatic reagent layer 406 (for clarity depicted in FIG. 3G only), a patterned spacer layer 408, a second patterned conductive layer 410 disposed above first patterned conductive layer 404, and an electrically-insulating top layer 412. Patterned spacer layer 408 is configured such that electrochemical-based analytical test strip 400 also includes a sample chamber 414 formed therein with patterned spacer layer 408 defining outer walls of sample chamber 414.

First patterned conductive layer 404 includes three electrodes, a counter electrode 404a (also referred to as a reference electrode), a first working electrode 404b and a second working electrode 404c (see FIG. 3G).

Second patterned conductive layer 410 includes a first phase-shift measurement electrode 411 and a second phase shift measurement electrode 413. Second patterned conductive layer 410 also includes a first phase-shift probe contact 416 and a second phase-shift probe contact 418.

During use of electrochemical-based analytical test strip 400 to determine an analyte in a bodily fluid sample (e.g., blood glucose concentration in a whole physiological fluid sample), electrodes 404a, 404b and 404c are employed by an associated meter (not shown) to monitor an electrochemical response of the electrochemical-based analytical test strip. The electrochemical response can be, for example, an electrochemical reaction induced current of interest. The magnitude of such a current can then be correlated, taking into consideration the physical characteristic (e.g., hematocrit) of the bodily fluid sample as determined by the bodily fluid sample's phase shift, with the amount of analyte present in the bodily fluid sample under investigation. During such use, a bodily fluid sample is applied to electrochemical-based analytical test strip 400 and, thereby, received in sample chamber 414.

Electrically-insulating substrate layer 402 can be any suitable electrically-insulating substrate known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, a polystyrene substrate, a silicon substrate, ceramic substrate, glass substrate or a polyester substrate (e.g., a 7 millimeters thick polyester substrate). The electrically-insulating substrate can have any suitable dimensions including, for example, a width dimension of about 5 mm, a length dimension of about 27 mm and a thickness dimension of about 0.5 mm.

First patterned conductive layer 404 can be formed of any suitable electrically conductive material such as, for example, gold, palladium, carbon, silver, platinum, tin oxide, iridium, indium, or combinations thereof (e.g., indium doped tin oxide). Moreover, any suitable technique or combination of techniques can be employed to form first patterned conductive layer 404 including, for example, sputtering, evaporation, electro-less plating, screen-printing, contact printing, laser ablation or gravure printing. A typical but non-limiting thickness for the patterned conductive layer is in the range of 5 nanometers to 400 nanometers.

As is known, conventional electrochemical-based analyte test strips employ a working electrode along with an associated counter/reference electrode and enzymatic reagent layer to facilitate an electrochemical reaction with an analyte of interest and, thereby, determine the presence and/or concentration of that analyte. For example, an electrochemical-based analyte test strip for the determination of glucose concentration in a fluid sample can employ an enzymatic reagent that includes the enzyme glucose oxidase and the mediator ferricyanide (which is reduced to the mediator ferrocyanide during the electrochemical reaction). Such conventional analyte test strips and enzymatic reagent layers are described in, for example, U.S. Pat. Nos. 5,708,247; 5,951,836; 6,241,862; and 6,284,125; each of which is hereby incorporated by reference herein to this application. In this regard, the reagent layer employed in various embodiments provided herein can include any suitable sample-soluble enzymatic reagents, with the selection of enzymatic reagents being dependent on the analyte to be determined and the bodily fluid sample. For example, if glucose is to be determined in a fluid sample, enzymatic reagent layer 406 can include glucose oxidase or glucose dehydrogenase along with other components necessary for functional operation.

In general, enzymatic reagent layer 406 includes at least an enzyme and a mediator. Examples of suitable mediators include, for example, ruthenium, Hexaammine Ruthenium (III) Chloride, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Enzymatic reagent layer 406 can be applied during manufacturing using any suitable technique including, for example, screen printing.

Applicants note that enzymatic reagent layer 406 may also contain suitable buffers (such as, for example, Tris HCl, Citraconate, Citrate and Phosphate), hydroxyethylcelulose [HEC], carboxymethylcellulose, ethycellulose and alginate, enzyme stabilizers and other additives as are known in the field.

Further details regarding the use of electrodes and enzymatic reagent layers for the determination of the concentrations of analytes in a bodily fluid sample, albeit in the absence of the phase-shift measurement electrodes, analytical test strips and related methods described herein, are in U.S. Pat. No. 6,733,655, which is hereby fully incorporated by reference herein to this application.

Patterned spacer layer 408 can be formed of any suitable material including, for example, a 95 micrometers thick, double-sided pressure sensitive adhesive layer, a heat activated adhesive layer, or a thermo-setting adhesive plastic layer. Patterned spacer layer 408 can have, for example, a thickness in the range of from about 1 micron to about 500 microns, preferably between about 10 microns and about 400 microns, and more preferably between about 40 microns and about 200 microns.

Second patterned conductive layer 410 can be formed of any suitable conductive material including, for example, copper, silver, palladium, gold and conductive carbon materials. Second patterned conductive layer 410 can be, for example, disposed on a lower surface of electrically-insulating top layer 412 (as depicted in FIGS. 3G-3J) or embedded in the lower surface of electrically-insulating top layer 412. Second patterned conductive layer 410 can have any suitable thickness including, for example, a thickness in the range of 20 microns to 400 microns.

First phase-shift measurement electrode 411 and second phase shift measurement electrode 413 of second patterned conductive layer 410 are separated within sample chamber 414 by a gap (in the horizontal direction of FIG. 3J) that is suitable for phase-shift measurement. Such a gap can be, for example, in the range of 20 microns to 1,400 microns with a typical gap being 500 microns. Moreover, the surface area of first phase-shift measurement electrode 111 and second phase shift measurement electrode 113 that is exposed to a bodily fluid sample within sample chamber 414 is typically 0.5 mm$^2$ but can range, for example, from 0.1 mm$^2$ to 2.0 mm$^2$.

Electrochemical-based analytical test strip 400 can be manufactured, for example, by the sequential aligned formation of first patterned conductive layer 404, enzymatic reagent layer 406, patterned spacer layer 408, second patterned conductive layer 410 and electrically insulating top layer 412 onto electrically-insulating substrate layer 402. Any suitable techniques known to one skilled in the art can be used to accomplish such sequential aligned formation, including, for example, screen printing, photolithography, photogravure, chemical vapour deposition, sputtering, tape lamination techniques and combinations thereof.

Analytical test strips according to embodiments can be configured, for example, for operable electrical connection (via, for example, first and second phase shift probe contacts 416 and 418) and use with the analytical test strip sample cell interface of a hand-held test meter as described in co-pending patent application Ser. No. 13/250,525, which is hereby incorporated by reference herein to this application with a copy provided in the Appendix.

It has been determined that a relationship exists between the reactance of a whole fluid sample and the physical characteristic (e.g., hematocrit) of that sample. Electrical modeling of a bodily fluid sample (e.g., a whole blood sample) as parallel capacitive and resistive components indicates that when an alternating current (AC) signal is forced through the bodily fluid sample, the phase shift of the alternating signal will be dependent on both the frequency of the alternating signal voltage and the physical characteristic (e.g., hematocrit) of the sample. Therefore, the physical characteristic (e.g., hematocrit) of a bodily fluid sample can be measured by, for example, driving alternating signals of a known frequency (or known frequencies) through the bodily fluid sample and detecting their phase shift. The phase-shift measurement electrodes of analytical test strips of various embodiments described herein are particularly suitable for use in such phase shift measurements since the first and second phase shift measurement electrodes are in direct contact with a bodily fluid sample present in the sample chamber. Moreover, a bodily fluid sample physical characteristic (e.g., hematocrit) ascertained from a phase shift measurement(s) can be employed to compensate for the effect of physical characteristic (e.g., hematocrit) during analyte determination.

Applicants note that for various embodiments of analytical test strips (e.g., an electrochemical-based analytical test strip) described here for use with a hand-held test meter in the determination of an analyte (such as glucose) in a bodily fluid sample (for example, a whole blood sample) may include an electrically insulating substrate, a first patterned conductor layer disposed on the electrically insulating substrate and having a working electrode and a reference electrode. The analytical test strip may also include an enzymatic reagent layer disposed on the working electrode, a first patterned spacer layer disposed over the first patterned conductor layer and defining both a first sample-receiving channel and an analyte determination sample chamber within the analytical test strip, and a second patterned spacer layer disposed over the first patterned spacer layer and defining at least a second sample-receiving channel. In addition, the analytical test strip further includes a bodily fluid phase-shift sample chamber in fluidic communication with the second sample-receiving channel. Moreover, the first sample-receiving channel and analyte determination sample chamber of the analytical test strip are isolated from the second sample-receiving channel and bodily fluid phase-shift sample chamber of the analytical test strip.

Analytical test strips of various embodiments described herein are believed by applicants to be beneficial in that, for example, the isolation (fluidic and electrical) between the analyte determination sample chamber and the bodily fluid phase-shift sample chamber prevents potential interference between the determination of the analyte in the bodily fluid sample and a phase-shift measurement of the bodily fluid. Applicants note that certain advantages are obtained by having the first sample-receiving channel and analyte determination chamber separated from the second sample-receiving channel and bodily fluid phase-shift sample chamber by portions of the first and/or second patterned spacer layers that can be thinner, thus providing for an analytical test strip with a small, yet mechanically stable, cross-section.

Referring to FIGS. 3K-3O, electrochemical-based analytical test strip 500 includes an electrically-insulating substrate 502, a first patterned conductor layer 504 disposed on the electrically-insulating substrate layer, an enzymatic reagent layer 506 (for clarity depicted in FIG. 3K only), a first patterned spacer layer 508, a second patterned spacer layer 510, and a top cover 511. In the embodiment of FIG. 3K, first pattered spacer layer 508 and second patterned spacer layer 510 are depicted as bi-layer structures. However, the first and second patterned spacer layers employed in various embodiments provided herein can be unitary layers or any other suitably formed layer.

First patterned spacer layer 508 is configured such that electrochemical-based analytical test strip 500 also includes a first sample-receiving channel 512 and an analyte determination sample chamber 514. First patterned spacer layer 508 is also configured to define a bodily fluid phase-shift sample chamber 516 and an analyte determination sample chamber vent 518 (for clarity not depicted in FIG. 3K).

Second patterned spacer layer 510 is configured to define a second sample-receiving channel 520 and a bodily fluid phase-shift chamber vent 522 (for clarity not depicted in FIG. 3K).

First patterned conductor layer 504 includes a first phase-shift measurement electrode 524, a second phase-shift measurement electrode 526, two working electrodes 528a and 528b and a reference electrode 530. For clarity, FIG. 3L depicts only first phase-shift measurement electrode 524 and second phase-shift measurement electrode 526 and not the entirety of first patterned conductor layer 504.

First sample-receiving channel 512 and analyte determination sample chamber 514 are isolated, both fluidically and electrically, from second sample-receiving channel 520 and bodily fluid phase-shift sample chamber 516 (see FIG. 3O in particular wherein the first and second patterned conductor layers are omitted for clarity). Moreover, in the embodiment of FIG. 3O, the bodily fluid phase-shift sample chamber is disposed in a side-by-side configuration with the analyte determination sample chamber.

During use of electrochemical-based analytical test strip 500 to determine an analyte in a bodily fluid sample (e.g., blood glucose concentration in a whole blood sample), working and reference electrodes are employed by an associated meter (not shown) to monitor an electrochemical response of the electrochemical-based analytical test strip. The electrochemical response can be, for example, an electrochemical reaction induced current of interest. The magnitude of such a signal can then be correlated, taking into consideration the haematocrit of the bodily fluid sample as determined by the bodily fluid sample's phase shift, with the amount of analyte present in the bodily fluid sample under investigation. During such use, a bodily fluid sample is applied to electrochemical-based analytical test strip 500 and, thereby, received in both analyte determination sample chamber 514 and bodily fluid phase-shift sample chamber 516.

Electrically-insulating substrate 502 can be any suitable electrically-insulating substrate known to one skilled in the art including, for example, a nylon substrate, polycarbonate substrate, a polyimide substrate, a polyvinyl chloride substrate, a polyethylene substrate, a polypropylene substrate, a glycolated polyester (PETG) substrate, a polystyrene substrate, a silicon substrate, ceramic substrate, glass substrate or a polyester substrate (e.g., a 7 millimeters thick polyester substrate). The electrically-insulating substrate can have any suitable dimensions including, for example, a width dimension of about 5 mm, a length dimension of about 27 mm and a thickness dimension of about 0.5 mm.

First patterned conductor layer 504 can be formed of any suitable electrically conductive material such as, for example, gold, palladium, carbon, silver, platinum, tin oxide, iridium, indium, or combinations thereof (e.g., indium doped tin oxide). Moreover, any suitable technique or combination of techniques can be employed to form first patterned conductor layer 504 including, for example, sputtering, evaporation, electro-less plating, screen-printing, contact printing, laser ablation or gravure printing. A typical but non-limiting thickness for the patterned conductor layer is in the range of 5 nanometers to 500 nanometers.

Applicants note that conventional electrochemical-based analyte test strips employ a working electrode along with an associated counter/reference electrode and enzymatic reagent layer to facilitate an electrochemical reaction with an analyte of interest and, thereby, determine the presence and/or concentration of that analyte. For example, an electrochemical-based analyte test strip for the determination of glucose concentration in a fluid sample can employ an enzymatic reagent that includes the enzyme glucose oxidase and the mediator ferricyanide (which is reduced to the mediator ferrocyanide during the electrochemical reaction). Such conventional analyte test strips and enzymatic reagent layers are described in, for example, U.S. Pat. Nos. 5,708,247; 5,951,836; 6,241,862; and 6,284,125; each of which is hereby incorporated by reference herein to this application.

In this regard, the reagent layer employed in various embodiments provided herein can include any suitable sample-soluble enzymatic reagents, with the selection of enzymatic reagents being dependent on the analyte to be determined and the bodily fluid sample. For example, if glucose is to be determined in a fluid sample, enzymatic reagent layer 506 can include glucose oxidase or glucose dehydrogenase along with other components necessary for functional operation.

In general, enzymatic reagent layer 506 includes at least an enzyme and a mediator. Examples of suitable mediators include, for example, ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Enzymatic reagent layer 506 can be applied during manufacturing using any suitable technique including, for example, screen printing.

Applicants note that enzymatic reagent layer 506 may also contain suitable buffers (such as, for example, Tris HCl, Citraconate, Citrate and Phosphate), hydroxyethylcelulose [HEC], carboxymethylcellulose, ethycellulose and alginate, enzyme stabilizers and other additives as are known in the field.

Further details regarding the use of electrodes and enzymatic reagent layers for the determination of the concentrations of analytes in a bodily fluid sample, albeit in the absence of the phase-shift measurement electrodes, bodily-fluid phase-shift sample chambers and second sample receiving channels analytical test strips and related methods described herein, are in U.S. Pat. No. 6,733,655, which is hereby fully incorporated by reference herein to this application.

First and second patterned spacer layers 508 and 510 respectively can be formed of any suitable material including, for example, a 95 micrometers thick, double-sided pressure sensitive adhesive layer, a heat activated adhesive layer, or a thermo-setting adhesive plastic layer. First patterned spacer layer 508 can have, for example, a thickness in the range of from about 1 micron to about 500 microns, preferably between about 10 microns and about 400 microns, and more preferably between about 40 microns and about 600 microns.

Electrochemical-based analytical test strip 500 can be manufactured, for example, by the sequential aligned formation of first patterned conductor layer 504, enzymatic reagent layer 506, first patterned spacer layer 508, and second patterned spacer layer 510 onto electrically-insulating substrate 502. Any suitable techniques known to one skilled in the art can be used to accomplish such sequential aligned formation, including, for example, screen printing, photolithography, photogravure, chemical vapour deposition, sputtering, tape lamination techniques and combinations thereof.

Analytical test strips according to embodiments can be configured, for example, for operable electrical connection and use with the analytical test strip sample cell interface of a hand-held test meter as described in co-pending patent application Ser. No. 13/250,525, which is hereby incorporated by reference herein to this application with a copy provided in the Appendix.

It has been determined that a relationship exists between the reactance of a fluid sample and the physical characteristic (e.g., hematocrit) of that sample. Electrical modeling of a bodily fluid sample (e.g., a whole blood sample) as parallel capacitive and resistive components indicates that when an alternating signal such as, for example, alternating-current (AC) signal is forced through the bodily fluid sample, the phase shift of the alternating signal will be dependent on both the frequency of the alternating signal voltage and the physical characteristic (e.g., hematocrit) of the sample. Therefore, the physical characteristic (e.g., hematocrit) of a bodily fluid sample can be measured by, for example, driving alternating signals of known frequencies through the bodily fluid sample and detecting their phase shift. The phase-shift measurement electrodes of analytical test strips of various embodiments described herein are particularly suitable for use in such phase-shift measurements since the first and second phase shift measurement electrodes are in direct contact with a bodily fluid sample present in the sample chamber. Moreover, a bodily fluid sample physical characteristic (e.g., hematocrit) ascertained from a phase shift measurement(s) can be employed to compensate for the effect of physical characteristic (e.g., hematocrit) during analyte determination.

Referring to FIGS. 3P-3T, electrochemical-based analytical test strip 600 includes an electrically-insulating substrate 602, a first patterned conductor layer 604 disposed on the electrically-insulating substrate layer, an enzymatic reagent layer 606 (for clarity depicted in FIG. 3P only), a first patterned spacer layer 608, a second patterned conductor layer 609, a second patterned spacer layer 610, and a top cover 611. In the embodiment of FIG. 3P, first pattered spacer layer 608 and second patterned spacer layer 610 are depicted as bi-layer structures. However, the first and second patterned spacer layers employed in various embodiments provided herein can be unitary layers or any other suitably formatted layer.

First patterned spacer layer 608 is configured such that electrochemical-based analytical test strip 600 also includes a first sample-receiving channel 612, an analyte determination sample chamber 614 and an analyte determination sample chamber vent 618 (not depicted in FIG. 3P but depicted with dashed lines in FIG. 3R). Analyte determination sample chamber vent 618 is configured to aid in the introduction of a bodily fluid sample into analyte determination sample chamber 614 via first sample-receiving channel 612.

Second patterned spacer layer 610 is configured to define a second sample-receiving channel 620, a bodily fluid phase-shift sample chamber 616 and a bodily fluid phase-shift chamber vent 622 (not depicted in FIG. 3P but depicted with dashed lines in FIG. 3S). Bodily fluid phase-shift chamber vent 622 is configured to aid in the introduction of a bodily fluid sample into bodily fluid phase-shift sample chamber 616 via second sample-receiving channel 620.

First patterned conductor layer 604 includes two working electrodes 628a and 628b (depicted in FIGS. 3P and 3Q) and a reference electrode 630 (also depicted in FIGS. 3P and 3Q). Second patterned conductor layer 609 includes a first phase-shift measurement electrode 624 and a second phase-shift measurement electrode 626 and is disposed above first patterned spacer layer 608 and embedded in the bi-layer structure of second pattered spacer layer 610.

First sample-receiving channel 612 and analyte determination sample chamber 614 are isolated, both fluidically and electrically, from second sample-receiving channel 620 and bodily fluid phase-shift sample chamber 616 (see FIG. 3T in particular wherein the first and second patterned conductor layers are not depicted for clarity).

In the various embodiments of the test strip, there are two measurements that are made to a fluid sample deposited on the test strip. One measurement is that of the concentration of the analyte (e.g. glucose) in the fluid sample while the other is that of physical characteristic (e.g., hematocrit) in the same sample. The measurement of the physical characteristic (e.g., hematocrit) is used to modify or correct the glucose measurement so as to remove or reduce the effect of red blood cells on the glucose measurements. Both measurements (glucose and hematocrit) can be performed in sequence, simultaneously or overlapping in duration. For example, the glucose measurement can be performed first then the physical characteristic (e.g., hematocrit); the physical characteristic (e.g., hematocrit) measurement first then the glucose measurement; both measurements at the same time; or a duration of one measurement may overlap a duration of the other measurement. Each measurement is discussed in detail as follow with respect to FIGS. 4A, 4B and 5.

Figure 4A:
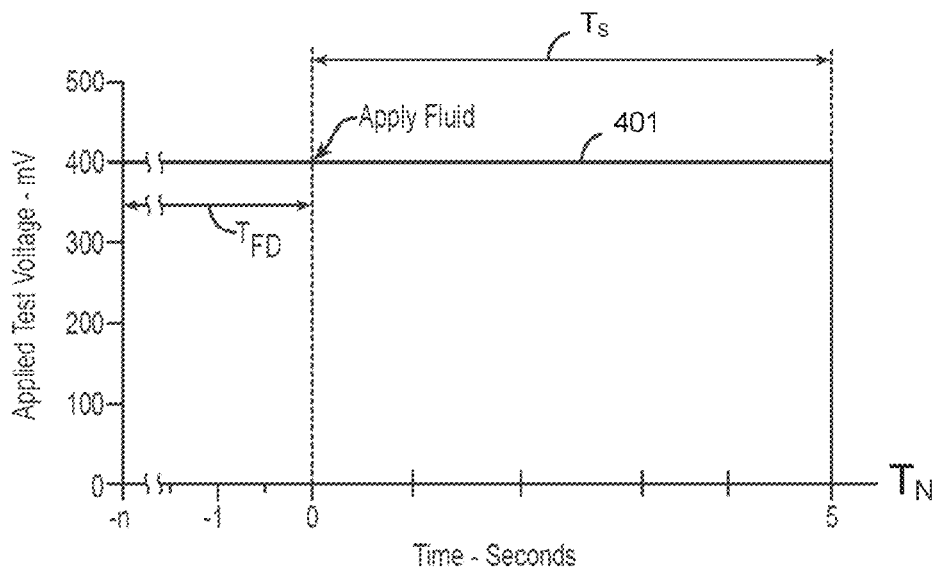
FIG. 4A illustrates a graph of time over applied potential to the test strip of FIG. 1.

FIG. 4A is an exemplary chart of a test signal applied to test strip 100 and its variations shown here in FIGS. 3A-3T. Before a fluid sample is applied to test strip 100 (or its variants 400, 500, or 600), test meter 200 is in a fluid detection mode in which a first test signal of about 400 millivolts is applied between second working electrode and reference electrode. A second test signal of about 400 millivolts is preferably applied simultaneously between first working electrode (e.g., electrode 12 of strip 100) and reference electrode (e.g., electrode 10 of strip 100). Alternatively, the second test signal may also be applied contemporaneously such that a time interval of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200 determines when a fluid is applied to test strip 100 (or its variants 400, 500, or 600) such that the fluid wets either the first working electrode 12 or second working electrode 14 (or both working electrodes) with respect to reference electrode 10. Once test meter 200 recognizes that the physiological fluid has been applied because of, for example, a sufficient increase in the measured test current at either or both of first working electrode 12 and second working electrode 14, test meter 200 assigns a zero second marker at zero time "0" and starts the test time interval $T_S$. Test meter 200 may sample the current transient output at a suitable sampling rate, such as, for example, every 1 milliseconds to every 100 milliseconds. Upon the completion of the test time interval $T_S$, the test signal is removed. For simplicity, FIG. 4A only shows the first test signal applied to test strip 100 (or its variants 400, 500, or 600).

Hereafter, a description of how glucose concentration is determined from the known signal transients (e.g., the measured electrical signal response in nanoamperes as a function of time) that are measured when the test voltages of FIG. 4A are applied to the test strip 100 (or its variants 400, 500, or 600).

Figure 4B:
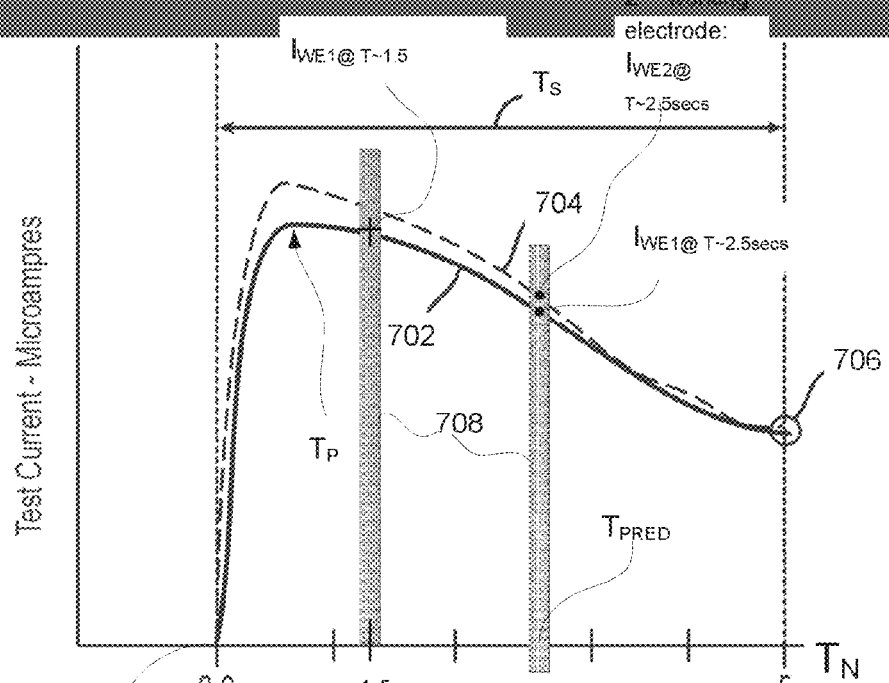
FIG. 4B illustrates a graph of time over output current from the test strip of FIG. 1.

In FIG. 4A, the first and second test voltages applied to test strip 100 (or its variants described herein) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 5 seconds after a reaction period and is typically about 3 seconds after a reaction period. Typically, test sequence time $T_S$ is measured relative to time $t_0$. As the voltage 401 is maintained in FIG. 4A for the duration of $T_S$, output signals are generated, shown here in FIG. 4B with the current transient 702 for the first working electrode 12 being generated starting at zero time and likewise the current transient 704 for the second working electrode 14 is also generated with respect to the zero time. It is noted that while the signal transients 702 and 704 have been placed on the same referential zero point for purposes of explaining the process, in physical term, there is a slight time differential between the two signals due to fluid flow in the chamber towards each of the working electrodes 12 and 14 along axis L-L. However, the current transients are sampled and configured in the microcontroller to have the same start time. In FIG. 4B, the current transients build up to a peak proximate peak time Tp at which time, the current slowly drops off until approximately one of 2.5 seconds or 5 seconds after zero time. At the point 706, approximately at 5 seconds, the output signal for each of the working electrodes 12 and 14 may be measured and added together. Alternatively, the signal from only one of the working electrodes 12 and 14 can be doubled.

Referring back to FIG. 2B, the system drives a signal to measure or sample the output signals $I_E$ from at least one the working electrodes (12 and 14) at any one of a plurality of time points or positions $T_1$, $T_2$, T3, and TN. As can be seen in FIG. 4B, the time position can be any time point or interval in the test sequence $T_S$. For example, the time position at which the output signal is measured can be a single time point $T_{1.5}$ at 1.5 seconds or an interval 708 (e.g., interval~10 milliseconds or more depending on the sampling rate of the system) overlapping the time point $T_{2.8}$ proximate 2.8 seconds.

From knowledge of the parameters of the test strip (e.g., batch calibration code offset and batch slope) for the particular test strip 100 and its variations, the analyte (e.g., glucose) concentration can be calculated. Output transient 702 and 704 can be sampled to derive signals $I_E$ (by summation of each of the current $I_{WE1}$ and $I_{WE2}$ or doubling of one of $I_{WE1}$ or $I_{WE2}$) at various time positions during the test sequence. From knowledge of the batch calibration code offset and batch slope for the particular test strip 100 and its variations in FIGS. 3B-3T, the analyte (e.g., glucose) concentration can be calculated.

It is noted that "Intercept" and "Slope" are the values obtained by measuring calibration data from a batch of test strips. Typically around 1500 strips are selected at random from the lot or batch. Physiological fluid (e.g., blood) from donors is spiked to various analyte levels, typically six different glucose concentrations. Typically, blood from 12 different donors is spiked to each of the six levels. Eight strips are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current) and a formula y=mx+c least squares fitted to the graph to give a value for batch slope m and batch intercept c for the remaining strips from the lot or batch. The applicants have also provided methods and systems in which the batch slope is derived during the determination of an analyte concentration. The "batch slope", or "Slope", may therefore be defined as the measured or derived gradient of the line of best fit for a graph of measured glucose concentration plotted against actual glucose concentration (or measured current versus YSI current). The "batch intercept", or "Intercept", may therefore be defined as the point at which the line of best fit for a graph of measured glucose concentration plotted against actual glucose concentration (or measured current versus YSI current) meets the y axis.

It is worthwhile here to note that the various components, systems and procedures described earlier allow for applicants to provide an analyte measurement system that heretofore was not available in the art. In particular, this system includes a test strip that has a substrate and a plurality of electrodes connected to respective electrode connectors. The system further includes an analyte meter 200 that has a housing, a test strip port connector configured to connect to the respective electrode connectors of the test strip, and a microcontroller 300, shown here in FIG. 2B. The microprocessor 300 is in electrical communication with the test strip port connector 220 to apply electrical signals or sense electrical signals from the plurality of electrodes.

Figure 2B:
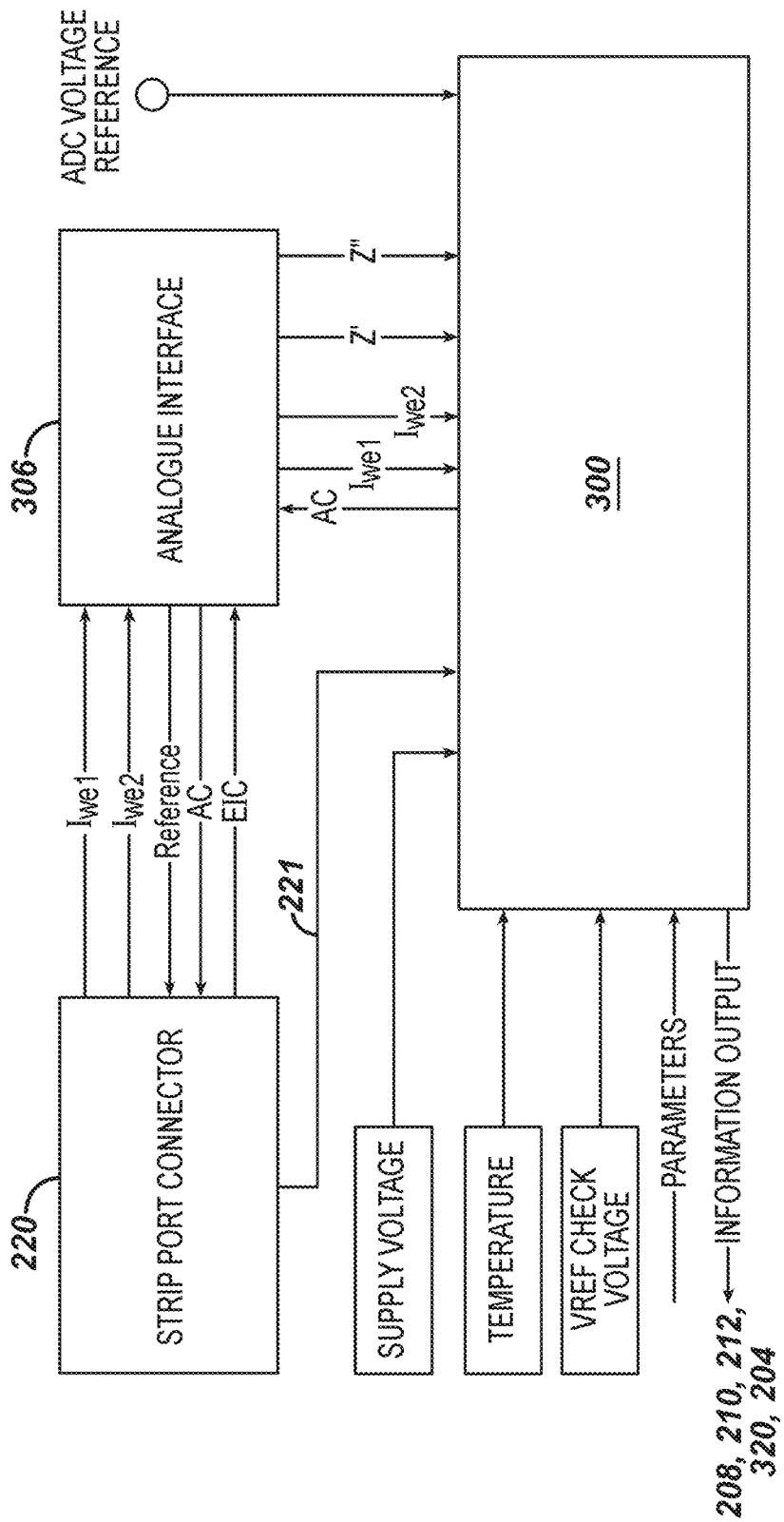
FIG. 2B illustrates in simplified schematic form a preferred implementation of a variation of meter 200.

Referring to FIG. 2B, details of a preferred implementation of meter 200 where the same numerals in FIGS. 2A and 2B have a common description. In FIG. 2B, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line for a reference electrode, and signal sensing lines from respective working electrode 1 and working electrode 2. A strip detection line 221 can also be provided for the connector 220 to indicate insertion of a test strip. The analog interface 306 provides four inputs to the processor 300: (1) real impedance Z'; (2) imaginary impedance Z"; (3) signal sampled or measured from working electrode 1 of the biosensor or $I_{we1}$; (4) signal sampled or measured from working electrode 2 of the biosensor or $I_{we2}$. There is one output from the processor 300 to the interface 306 to drive an oscillating signal AC of any value from 25 kHz to about 250 kHz or higher to the physical characteristic sensing electrodes. A phase differential P (in degrees) can be determined from the real impedance Z' and imaginary impedance Z" where:

$$P=\tan^{-1}\{Z''/Z'\} \qquad \text{Eq. 3.1}$$

and magnitude M (in ohms and conventionally written as |Z|) from line Z' and Z" of the interface 306 can be determined where $$M=\sqrt{(Z')^2+(Z'')^2} \qquad \text{Eq. 3.2}$$

In this system, the microprocessor is configured to: (a) apply a first signal to the plurality of electrodes so that a batch slope defined by a physical characteristic of a fluid sample is derived and (b) apply a second signal to the plurality of electrodes so that an analyte concentration is determined based on the derived batch slope. For this system, the plurality of electrodes of the test strip or biosensor includes at least two electrodes to measure the physical characteristic and at least two other electrodes to measure the analyte concentration. For example, the at least two electrodes and the at least two other electrodes are disposed in the same chamber provided on the substrate. Alternatively, the at least two electrodes and the at least two other electrodes are disposed in different chambers provided on the substrate. It is noted that for some embodiments, all of the electrodes are disposed on the same plane defined by the substrate. In particular, in some of the embodiments described herein, a reagent is disposed proximate the at least two other electrodes and no reagent is disposed on the at least two electrodes. One feature of note in this system is the ability to provide for an accurate analyte measurement within about 10 seconds of deposition of a fluid sample (which may be a physiological sample) onto the biosensor as part of the test sequence.

As an example of an analyte calculation (e.g., glucose) for strip 100 (FIG. 3A(1), 3A(2), or 3A(3) and its variants in FIGS. 3B-3T), it is assumed in FIG. 4B that the sampled signal value at 706 for the first working electrode 12 is about 1600 nanoamperes whereas the signal value at 706 for the second working electrode 14 is about 1300 nanoamperes and the calibration code of the test strip indicates that the Intercept is about 500 nanoamperes and the Slope is about 18 nanoamperes/mg/dL. Glucose concentration $G_0$ can be thereafter be determined from Equation 3.3 as follow:

$$G_0 = [(I_E) - \text{Intercept}]/\text{Slope} \qquad \text{Eq. 3.3}$$

where
- $I_E$ is a signal (proportional to analyte concentration) which is the total signal from all of the electrodes in the biosensor (e.g., for sensor 100, both electrodes 12 and 14 (or $I_{we1} + I_{we2}$));
- $I_{we1}$ is the signal measured for the first working electrode at the set sampling time;
- $I_{we2}$ is the signal measured for the second working electrode at the set sampling time;
- Slope is the value obtained from calibration testing of a batch of test strips of which this particular strip comes from;
- Intercept is the value obtained from calibration testing of a batch of test strips of which this particular strip comes from.

From Eq. 3.3; $G_0 = [(1600+1300) - 500]/18$ and therefore, $G_0 = 133.33$ nanoamp~133 mg/dL.

It is noted here that although the examples have been given in relation to a biosensor 100 which has two working electrodes (12 and 14 in FIG. 3A(1)) such that the measured currents from respective working electrodes have been added together to provide for a total measured current $I_E$, the signal resulting from only one of the two working electrodes can be multiplied by two in a variation of test strip 100 where there is only one working electrode (either electrode 12 or 14). Instead of a total signal, an average of the signal from each working electrode can be used as the total measured current $I_E$ for Equations 3.3, 6, and 8-11 described herein, and of course, with appropriate modification to the operational coefficients (as known to those skilled in the art) to account for a lower total measured current $I_E$ than as compared to an embodiment where the measured signals are added together. Alternatively, the average of the measured signals can be multiplied by two and used as $I_E$ in Equations 3.3, 6, and 8-11 without the necessity of deriving the operational coefficients as in the prior example. It is noted that the analyte (e.g., glucose) concentration here is not corrected for any physical characteristic (e.g., hematocrit) value) and that certain offsets may be provided to the signal values $I_{we1}$ and $I_{we2}$ to account for errors or delay time in the electrical circuit of the meter 200. Temperature compensation can also be utilized to ensure that the results are calibrated to a referential temperature such as for example room temperature of about 20 degrees Celsius.

Figure 5:
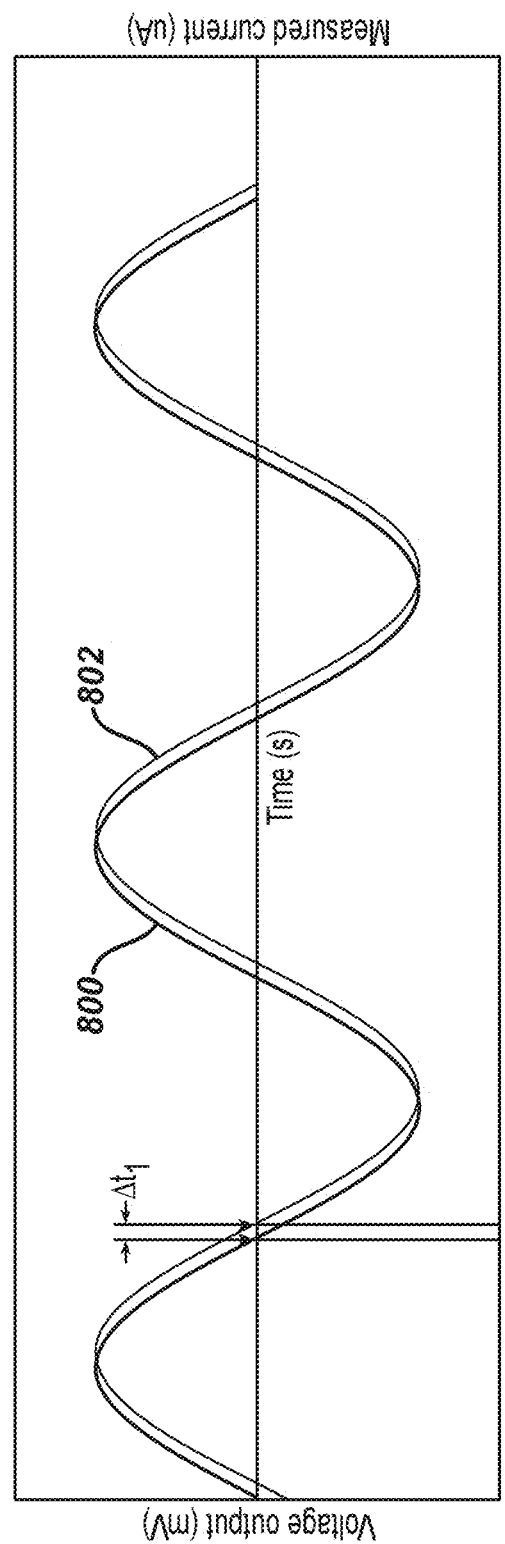
FIG. 5 illustrates an exemplary waveform applied to the test chamber and a waveform as measured from the test chamber to show a time delay between the waveforms.

Now that a glucose concentration ($G_0$) can be determined from the signal $I_E$, a description of applicant's technique to determine the physical characteristic (e.g., hematocrit) of the fluid sample is provided in relation to FIG. 5. In FIG. 5, the system 200 (FIG. 2) applies a first oscillating input signal 800 at a first frequency (e.g., of about 25 kilo-Hertz) to a pair of sensing electrodes. The system is also set up to measure or detect a first oscillating output signal 802 from the third and fourth electrodes, which in particular involve measuring a first time differential $\Delta t_1$ between the first input and output oscillating signals. At the same time or during overlapping time durations, the system may also apply a second oscillating input signal (not shown for brevity) at a second frequency (e.g., about 100 kilo-Hertz to about 1 MegaHertz or higher, and preferably about 250 kilo Hertz) to a pair of electrodes and then measure or detect a second oscillating output signal from the third and fourth electrodes, which may involve measuring a second time differential $\Delta t_2$ (not shown) between the first input and output oscillating signals. From these signals, the system estimates a physical characteristic (e.g., hematocrit) of the fluid sample based on the first and second time differentials $\Delta t_1$ and $\Delta t_2$. Thereafter, the system is able to derive a glucose concentration. The estimate of the physical characteristic (e.g., hematocrit) can be done by applying an equation of the form $$HCT_{EST} = \frac{(C_1 \Delta t_i - C_2 \Delta t_2 - C_3)}{m_1} \qquad \text{Eq. 4.1}$$

where
- each of $C_1$, $C_2$, and $C_3$ is an operational constant for the test strip and
- $m_1$ represent a parameter from regressions data.

Details of this exemplary technique can be found in Provisional U.S. Patent Application Ser. No. 61/530,795 filed on Sep. 2, 2011, entitled, "Hematocrit Corrected Glucose Measurements for Electrochemical Test Strip Using Time Differential of the Signals", which is hereby incorporated by reference.

Another technique to determine physical characteristic (e.g., hematocrit) can be by two independent measurements of physical characteristic (e.g., hematocrit). This can be obtained by determining: (a) the impedance of the fluid sample at a first frequency and (b) the phase angle of the fluid sample at a second frequency substantially higher than the first frequency. In this technique, the fluid sample is modeled as a circuit having unknown reactance and unknown resistance. With this model, an impedance (as signified by notation "|Z|") for measurement (a) can be determined from the applied voltage, the voltage across a known resistor (e.g., the intrinsic strip resistance), and the voltage across the unknown impedance Vz; and similarly, for measurement (b) the phase angle can be measured from a time difference between the input and output signals by those skilled in the art. Details of this technique is shown and described in provisional patent application Ser. No. 61/530,808 filed Sep. 2, 2011, which is incorporated by reference. Other suitable techniques for determining the physical characteristic (e.g., hematocrit, viscosity, temperature or density) of the fluid sample can also be utilized such as, for example, U.S. Pat. No. 4,919,770, U.S. Pat. No. 7,972,861, US Patent Application Publication Nos. 2010/0206749, 2009/0223834, or "Electric Cell—Substrate Impedance Sensing (ECIS) as a Noninvasive Means to Monitor the Kinetics of Cell Spreading to Artificial Surfaces" by Joachim Wegener, Charles R. Keese, and Ivar Giaever and published by Experimental Cell Research 259, 158-166 (2000) doi:10.1006/excr.2000.4919, available online at http://www.idealibrary.com1; "Utilization of AC Impedance Measurements for Electrochemical Glucose Sensing Using Glucose Oxidase to Improve Detection Selectivity" by Takuya Kohma, Hidefumi Hasegawa, Daisuke Oyamatsu, and Susumu Kuwabata and published by Bull. Chem. Soc. Jpn. Vol. 80, No. 1, 158-165 (2007), all of these documents are incorporated by reference.

Another technique to determine the physical characteristic (e.g., hematorcrits, density, or temperature) can be obtained by knowing the phase difference (e.g., phase angle) and magnitude of the impedance of the sample. In one example, the following relationship is provided for the estimate of the physical characteristic or impedance characteristic of the sample ("IC"):

$$IC = M^2 * y_1 + M * y_2 + y_3 + P^2 * y_4 + P * y_5 \qquad \text{Eq. 4.2}$$

where:
M represents a magnitude |Z| of a measured impedance in ohms);
P represents a phase difference between the input and output signals (in degrees)
$y_1$ is about −3.2e−08 and ±10%, 5% or 1% of the numerical value provided hereof (and depending on the frequency of the input signal, can be zero);
$y_2$ is about 4.1e−03 and ±10%, 5% or 1% of the numerical value provided hereof (and depending on the frequency of the input signal, can be zero);
$y_3$ is about −2.5e+01 and ±10%, 5% or 1% of the numerical value provided hereof;
$y_4$ is about 1.5e−01 and ±10%, 5% or 1% of the numerical value provided hereof (and depending on the frequency of the input signal, can be zero); and
$y_5$ is about 5.0 and ±10%, 5% or 1% of the numerical value provided hereof (and depending on the frequency of the input signal, can be zero).

It is noted here that where the frequency of the input AC signal is high (e.g., greater than 75 kHz) then the parametric terms $y_1$ and $y_2$ relating to the magnitude of impedance M may be ±200% of the exemplary values given herein such that each of the parametric terms may include zero or even a negative value. On the other hand, where the frequency of the AC signal is low (e.g., less than 75 kHz), the parametric terms $y_4$ and $y_5$ relating to the phase angle P may be ±200% of the exemplary values given herein such that each of the parametric terms may include zero or even a negative value. It is noted here that a magnitude of H or HCT, as used herein, is generally equal to the magnitude of IC. In one exemplary implementation, H or HCT is equal to IC as H or HCT is used herein this application.

In another alternative implementation, Equation 4.3 is provided. Equation 4.3 is the exact derivation of the quadratic relationship, without using phase angles as in Equation 4.2.

$$IC = \frac{-y_2 + |\sqrt{y_2^2 - (4y_3(y_1 - M))}|}{2y_1} \qquad \text{Eq. 4.3}$$

where:
IC is the Impedance Characteristic [%];
M is the magnitude of impedance [Ohm];
$y_1$ is about 1.2292e1 and ±10%, 5% or 1% of the numerical value provided hereof;
$y_2$ is about −4.3431e2 and ±10%, 5% or 1% of the numerical value provided hereof;
$y_3$ is about 3.5260e4 and ±10%, 5% or 1% of the numerical value provided hereof.

By virtue of the various components, systems and insights provided herein, at least four techniques of determining an analyte concentration from a fluid sample (which may be a physiological sample) (and variations of such method) are achieved by applicants.

With reference to FIG. 6A1, the method involves depositing a fluid sample (which may be a physiological sample) on a biosensor at step 904A (e.g., in the form of a test strip as show in FIG. 3A (1), 3A (2), or 3A (3)-3T) that has been inserted into a meter (step 902A). Once the meter 200 is turned on, a voltage is applied to the strip 100 (or its variants 400, 500, or 600) and when the sample is deposited onto the test chamber, the applied voltage physically transforms the analyte in the sample into a different form due to the enzymatic reaction of the analyte with the reagent in the test chamber. As the sample flows into the capillary channel of the test cell, at least one physical characteristic of the sample is obtained (step 908A). In particular, the step of obtaining the physical characteristic (step 908A) may include applying a first signal to the sample to measure a physical characteristic of the sample, while the step 906A of initiating an enzymatic reaction may involve driving a second signal to the sample, and the step of measuring (step 912A) may entail evaluating an output signal from the at least two electrodes at a point in time after the start of the test sequence, in which a new batch slope is set (at step 910A) as a function of at least the measured or estimated physical characteristic (step 908A).

Figure 7:
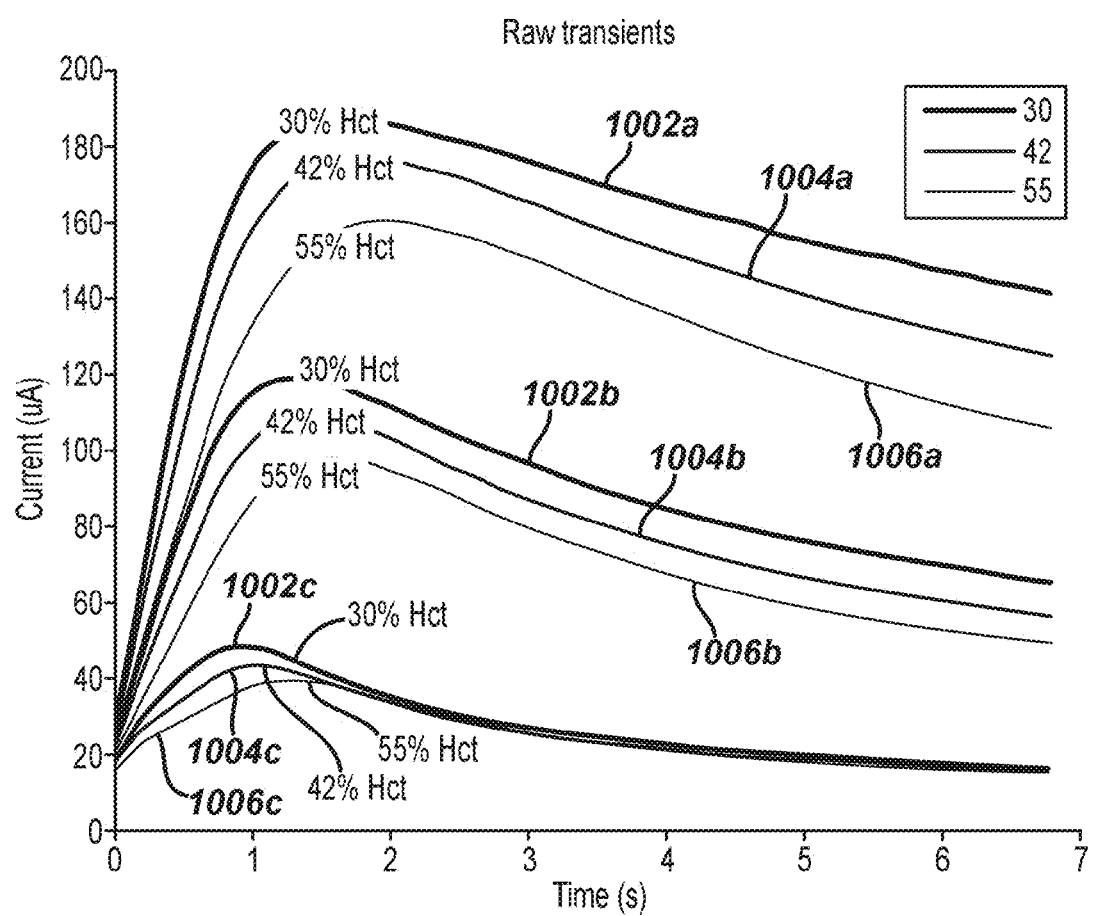
FIG. 7 illustrates a signal output transient of the biosensor and the range of time point utilized for determination of the analyte, as well as the estimation of the analyte concentration.

The setting of a new batch slope to derive a more accurate analyte concentration measurement merits a discussion with reference to FIGS. 7 and 6A2. Applicants have found that the existing glucose test strip made by LifeScan (marketed under the Ultra brand) has variations in the signal output transients depending on the glucose concentration and hematocrit. These variations can be seen in FIG. 7 in which at high level of glucose ("High G") or mid-level of glucose ("Mid-G"), the signal transient varies distinctly as a function of the physical characteristic (e.g., hematocrit) level and at low glucose level ("Lo-G") the signal transient does not vary as distinctly as in the High-G or Mid-G as a function of hematocrit. Specifically, at the High G, the signal transients 1000a, 1002a, and 1004a (for 30%, 42% and 55% Hct) maintain a generally consistent separation in signal output over time after the peak at about 1.5 seconds after the start of the test sequence. Similarly, at the Mid-G, the signal transients 1000b, 1002b, and 1004b (for 30%, 42%, and 55% Hct) maintains a consistent separation in signal output over time after the peak at about 1.5 seconds after the start of the test sequence. At the Low-G, the signal transients 1000c, 1002c, and 1004c (for 30%, 42%, and 55% Hct) generally converge together after the peak at about 1.5 seconds after the start of the test sequence.

Based on these observations, applicants have found that a relationship exists between the batch slope of these test strips tested at the Lo-G, Mid-G, and Hi-G levels with respect to 30%, 42%, and 55% hematocrit levels. In particular, applicants have found that the batch slope for these strips is generally curved with respect to hematocrit level, shown here in FIG. 6A2. In FIG. 6A2, the batch slope declines in a generally curved manner at low (e.g., 30%), medium (e.g., 42%), and high (e.g., 55%) hematocrits. As a consequence, by knowing the physical characteristic of the sample (e.g., hematocrit) from Equation 4 above, the relationship in FIG. 6A2 can be exploited to allow the slope in Equation 3.3 to accommodate the different levels of physical characteristic (e.g., hematocrit) so as to achieve much more accurate glucose concentration measurements.

It should be noted that while slope "x" in FIG. 6A2 appears to be a linear line, slope "x" is in fact a curved line and a curve has been fitted for the relationship between physical characteristic (e.g., hematocrit) and slope implicit in FIG. 6A2. This fitted curve for FIG. 6A2 is found by applicants to be a second order equation of the form:

$$\text{NewSlope} = aH^2 + bH + c \qquad \text{Eq. 5}$$

where

NewSlope is the derived or calculated new batch slope;

H is measured or estimated physical characteristic (e.g., hematocrit);

a is about 1.35e-6, b is about -3.79e-4, c is about 3.56e-2.

Equation 5 can be used instead of plotting against FIG. 6A2, depending on the available computing power of the processor. The viability of this approach can be seen here in FIG. 6A3 which is a plot of a large number of test strips at different glucose ranges and hematocrit levels versus percent bias by use of Equations 5 and 6. In FIG. 6A3, it can be seen that virtually all of the glucose concentration at different glucose ranges (low, medium, and high) across about 30%, 42%, and about 55% hematocrit have a bias of less than +10%.

Continuing on with the exemplary process of FIG. 6A1, once the physical characteristic is known at step 908A from Equation 4, such as for example Hct~55%, the graph of FIG. 6A2 is utilized to determine the appropriate batch slope, designated here as "NewSlope" which is about 0.019. Alternatively, Equation 5 can be utilized to derive the NewSlope from the measured or estimated physical characteristic (e.g., hematocrit). This NewSlope (from FIG. 6A2 or Eq. 5) is used along with the batch intercept (Intercept) of the particular batch of test strip in Equation 3.3, as set forth below in Equation 6.

$$G_0 = \left[ \frac{I_E - \text{Intercept}}{x} \right]. \qquad \text{Eq. 6}$$

where $G_0$ represents an analyte concentration $I_E$ is a signal (proportional to analyte concentration) as measured at the specified SamplingTime point;

x or "NewSlope" is the value obtained from the relationship in FIG. 6A2 or from Eq. 5;

Intercept is the value obtained from calibration testing of a batch of test strips of which this particular strip comes from.

Once the signal output $I_E$ of the test chamber is measured at the designated time, typically at about 2.5 seconds or about 5 seconds, the signal $I_E$ is thereafter used with the NewSlope (of the batch) and Intercept (of the batch) in the calculation of the analyte concentration (in this case glucose) with Eq. 6 above. It is noted here that $I_E$ could be a current from only one working electrode where the biosensor has only one working electrode, a sum of current outputs from two working electrodes, a current from one working electrode multiplied by two or an average current from the two working electrodes. It should be noted that the step of applying the first signal and the driving of the second signal is in sequential order in that the order may be the first signal then the second signal or both signals overlapping in sequence; alternatively, the second signal first then the first signal or both signals overlapping in sequence. Alternatively, the applying of the first signal and the driving of the second signal may take place simultaneously.

In the method, the step of applying of the first signal involves directing an alternating signal provided by an appropriate power source (e.g., the meter 200) to the sample so that a physical characteristic of the sample is determined from an output of the alternating signal. The physical characteristic being detected may be one or more of viscosity, hematocrit, temperature or density. The directing step may include driving first and second alternating signals at different respective frequencies in which a first frequency is lower than the second frequency. Preferably, the first frequency is at least one order of magnitude lower than the second frequency. As an example, the first frequency may be any frequency in the range of about 10 kHz to about 100 kHz and the second frequency may be from about 250 kHz to about 1 MHz or more. As used herein, the phrase "alternating signal" can have some portions of the signal alternating in polarity or all alternating current signal or an alternating current with a direct current offset or even a multi-directional signal combined with a direct-current signal.

Although the method may specify only one sampling time point, the method may include sampling as many time points as required, such as, for example, sampling the signal output continuously (e.g., at specified sampling time such as, every 10 milliseconds to 100 milliseconds) from the start of the test sequence until at least about 10 seconds after the start and the results stored for processing near the end of the test sequence. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. In this variation, the sampled signal output at the specified sampling time is the value used to calculate the analyte concentration.

It is noted that in the preferred embodiments, the measure of a signal output for the glucose concentration is performed prior to the measurement or estimation of the hematocrit. Alternatively, the hematocrit level can be measured or estimated prior to the measurement of the glucose concentration.

Thus, as another benefit of the teaching provided herein, a method of demonstrating increased accuracy of a test strip than heretofore is achieved. This method involves providing a batch of test strips, typically in a batch of at least about 1500 test strips (and in some cases up to 1 million test strips per batch), introducing a referential sample containing a referential concentration of an analyte to each of the batch of test strips to initiate a test sequence (a "referential sample" contains a "referential" or "known" concentration of an analyte, e.g. glucose). The method involves, reacting the analyte with a reagent on the test strip to cause a physical transformation of the analyte proximate the two electrodes, determining a physical characteristic of the referential sample, deriving a biosensor parameter (e.g., a batch slope) for the batch of test strips based on the determined physical characteristics of the referential sample; sampling an electrical output of the referential sample at a predetermined time point during the test sequence, and calculating an analyte concentration based on the derived biosensor parameter and sampled electrical output to provide for a final analyte concentration value for each of the batch of test strips such that at least 95% of the analyte concentration values of the batch of test strips are within about +15% of the referential analyte concentration for the range of hematocrit from about 30% to about 55%, shown here in FIG. 6A3 (an example of a "physical transformation", specifically an "enzymatic reaction", of an analyte to form a different material is the oxidation of glucose to D-glucono-δ-lactone and hydrogen peroxide by glucose oxidase (e.g. where the analyte is glucose and the reagent comprises glucose oxidase)).

In FIG. 6A3, experiments were performed to quantify the improvement in the glucose measurements from the method noted above. The quantification of the improvement can be shown by the "bias" at different levels of hematocrit. The bias, which is an estimate of the relative error in the glucose measurement, was calculated for each glucose concentrations determined with the method described in this example. The bias for each glucose concentration was determined with equations of the form:

$$Bias_{abs} = G_{calculated} - G_{reference} \text{ for } G_{reference} \text{ less than 100 mg/dL glucose}$$

and $$Bias_{\%} = \frac{G_{calculated} - G_{reference}}{G_{reference}} \text{ for}$$

$$G_{reference} \text{ greater than or equal to 100 mg/dL glucose}$$

where
  $Bias_{abs}$ is absolute bias,
  $Bias_{\%}$ is percent bias,
  $G_{calculated}$ is the glucose concentration determined by the method herein
and
  $G_{reference}$ is the reference glucose concentration.

As can be seen in FIG. 6A3, most or virtually all of the glucose concentration using this technique are within about ±15% bias for hematocrit from about 30% hematocrit to about 55% hematocrit. Specifically, at region 1010A, only one glucose concentration greater than 100 mg/dL is outside the bias of −15%; at region 1012A of intermediate hematocrit, a few glucose concentrations are outside the bias range of −15% and at region 1014A of high hematocrit, more glucose concentrations are dispersed outside the bias of −15% as compared to regions 1010A and 1012A.

With reference to FIG. 6B1, another technique involves depositing a fluid sample (which may be a physiological sample) on a biosensor at step 904B (e.g., in the form of a test strip as show in FIG. 3A (1), 3A(2), or 3A(3)-3T) that has been inserted into a meter (step 902B). Once the meter 200 is turned on, a voltage is applied to the strip 100 (or its variants 400, 500, or 600) and when the sample is deposited onto the test chamber, the applied voltage physically transforms the analyte in the sample into a different form due to the enzymatic reaction of the analyte with the reagent in the test chamber. As the sample flows into the capillary channel of the test cell, at least one physical characteristic of the sample is obtained (step 908B). In particular, the step of obtaining or measuring the physical characteristic (step 908B) may include applying a first signal to the sample to derive a physical characteristic of the sample, while the step 906B of initiating an enzymatic reaction (e.g., by applying electrical signals to the sample and reagent) may involve driving a second signal to the sample, and the step of measuring (step 912B) may entail measuring an output signal from the at least two electrodes at a point in time after the start of the test sequence, in which a sampling time point is specified (at step 910B) as a function of at least the measured or estimated physical characteristic (step 908B).

In a variation of the method, the step of applying of the first signal involves directing an alternating signal provided by an appropriate power source (e.g., the meter 200) to the sample so that a physical characteristic of the sample is determined from an output of the alternating signal. The physical characteristic being detected may be one or more of viscosity, hematocrit or density of the sample (which may not be physiological fluid such as, for example, calibration fluid). The directing step may include driving first and second alternating signals at different respective frequencies in which a first frequency is lower than the second frequency. Preferably, the first frequency is at least one order of magnitude lower than the second frequency. As an example, the first frequency may be any frequency in the range of about 10 kHz to about 100 kHz and the second frequency may be from about 250 kHz to about 1 MHz or more. As used herein, the phrase "alternating signal" can have some portions of the signal alternating in polarity or all alternating current signal or an alternating current with a direct current offset or even a multi-directional signal combined with a direct-current signal.

Once the physical characteristic of the sample is determined or obtained from a suitable technique, the physical characteristic can be used to specify a sampling time point at which point during the test sequence the output signal of the test chamber could be measured. In particular, applicants have found a relationship between the physical characteristic and the sampling time point, as shown here in FIG. 7. This relationship has been further explored such that applicants were able to derive a direct relationship between the sampling time point of the sample and the physical characteristic of the sample (e.g., hematocrit), shown here in FIG. 6B2. As a consequence, by knowing the physical characteristic of the sample (e.g., hematocrit) from Equation 4 above, the relationship in FIG. 6B2 can be exploited to allow the sampling time point to be specified to accommodate the different levels of physical characteristic (e.g., hematocrit) so as to achieve much more accurate glucose concentration measurements than heretofore.

Referring back to FIG. 7, it can be seen that as the analyte concentration (proportional to the signal output) increases, the peak of the high glucose concentration (denoted by 1002a, 1004a, and 1006a) is shifted to the right as compared to the medium glucose concentration (denoted by 1002b, 1004b, and 1006b). Similarly, the peak of the medium glucose concentration is further to the right of FIG. 7 as compared to low glucose concentration (denoted by 1002c, 1004c, and 1006c). It can also be seen here that the steady-state of the low glucose concentrations (1002c, 1004c, and 1006c) is reached earlier than the medium glucose concentrations (1002b, 1004b, and 1006b). This pattern is repeated for high glucose concentration (1002a, 1004a, and 1006b) as compared to medium glucose concentrations.

From data in FIG. 7, applicants were able to derive a second degree relationship between the sensed physical characteristic and the sampling time, shown here in FIG. 6B2. In FIG. 6B2, a curve is fitted to hematocrit values at about 30%, 42% and about 55% and glucose values for these ranges of hematocrits (from FIG. 7). This fitted curve is found by applicants to be an equation of the form:

$$SamplingTime = x_1 H^{x_2} + x_3 \qquad \text{Eq. 7}$$

where,
"Sampling Time" is designated (for convenience) as a time point from the start of the test sequence at which to sample the output signal of the test strip,
H represents the physical characteristic of the sample;
$x_1$ is about 4.3e5;
$x_2$ is about −3.9; and
$x_3$ is about 4.8.

Although the method may specify only one sampling time point, the method may include sampling as many time points as required, such as, for example, sampling the signal output continuously (e.g., at specified sampling time such as, every 10 milliseconds to 100 milliseconds) from the start of the test sequence until at least about 10 seconds after the start and the results stored for processing near the end of the test sequence. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. In this variation, the sampled signal output at the specified sampling time is the value used to calculate the analyte concentration.

Referring back to FIG. 6B1, the method can now determine the analyte concentration (step 914B) based on the measured signal (step 912B) sampled at the specified time point, which specified time point is a function of the obtained or measured or estimated physical characteristic of the sample (e.g., from plot of FIG. 6B2 or Equation 7). That is, once the sampling time T has been specified from Equation 7, the method provides for measuring the output signal from the test chamber (e.g., chamber 92) so that the sampled output can be utilized with Equation 3.3 to provide for an analyte (e.g., glucose) concentration.

Alternatively, a look-up table, represented exemplarily here with reference to Table 1 can also be utilized in place of Equation 7 or in addition to Equation 7 to specify an appropriate sampling time point. In Table 1, the value of the physical characteristic is used by the processor of the system to look up the appropriate time at which the signal output of the biosensor is sampled or measured to determine the analyte concentration. For example, once the physical characteristic has been determined, in this case about 33% hematocrit, the time at which the signal output of the biosensor 100 is utilized in determining the analyte concentration can be gleaned from Table 1, which shows that the time at which the system must sample the signal output is at approximately 5.32 seconds after the start of the test sequence.

TABLE 1

| Physical Characteristic (e.g., Hematocrit %) | Sampling Time T (seconds) |
|---|---|
| 30 | 5.56 |
| 31 | 5.46 |
| 32 | 5.38 |
| 33 | 5.32 |
| 34 | 5.26 |
| 35 | 5.2 |
| 36 | 5.16 |
| 37 | 5.12 |
| 38 | 5.08 |
| 39 | 5.06 |
| 40 | 5.02 |
| 41 | 5 |
| 42 | 5 |
| 43 | 4.98 |
| 44 | 4.96 |
| 45 | 4.96 |
| 46 | 4.94 |
| 47 | 4.92 |
| 48 | 4.92 |
| 49 | 4.9 |
| 50 | 4.9 |
| 51 | 4.9 |
| 52 | 4.88 |
| 53 | 4.88 |
| 54 | 4.88 |
| 55 | 4.86 |

It should be noted that the step of applying the first signal and the driving of the second signal is in sequential order in that the order may be the first signal then the second signal or both signals overlapping in sequence; alternatively, the second signal first then the first signal or both signals overlapping in sequence. Alternatively, the applying of the first signal and the driving of the second signal may take place simultaneously.

It is noted that in the preferred embodiments, the measurement of a signal output for the glucose concentration is performed prior to the estimation of the physical characteristic (e.g., hematocrit). Alternatively, the physical characteristic (e.g., hematocrit) level can be estimated, measured, or obtained prior to the measurement of the glucose concentration.

Thus, as another benefit of the teaching provided herein, a method of demonstrating increased accuracy of a test strip than heretofore is achieved. This method involves providing a batch of test strips, typically in a batch of at least about 1500 test strips (and in some cases up to 1 million test strips per batch), introducing a referential sample containing a referential concentration of an analyte to each of the batch of test strips to initiate a test sequence. The method involves reacting the analyte to cause a physical transformation of the analyte with the reagent between the two electrodes, determining a physical characteristic of the referential sample, estimating the analyte concentration, sampling an electrical output of the referential sample at a specified time point during the test sequence defined by the measured or estimated physical characteristic of the sample and the estimated analyte concentration, and calculating an analyte concentration based on the specified sampling time such that at least 95% of the analyte concentration values of the batch of test strips are within about 25% of the referential analyte concentration for the range of hematocrit from about 30% to about 55%, shown here in FIG. 6B3.

As can be seen in FIG. 6B3, most or virtually all of the glucose concentration using this technique are within about ±25% bias for hematocrit from about 30% hematocrit to about 55% hematocrit. Specifically, at region 1010B, only one glucose concentration greater than 100 mg/dL is outside the bias of −15%; at region 1012B of intermediate hematocrit, a few glucose concentrations are outside the bias range of about −25% and at region 1014B of high hematocrit, more glucose concentrations are dispersed outside the bias of about −25% as compared to regions 1010B and 1012B.

Yet another technique can be understood with reference to FIG. 6C1. This technique involves depositing a fluid sample (which may be a physiological sample) on a biosensor at step 904C (e.g., in the form of a test strip as show in FIG.

3A (1), 3A(2), or 3A(3)-3T) that has been inserted into a meter (step 902C). Once the meter 200 is turned on, a voltage is applied to the strip 100 (or its variants 400, 500, or 600) and when the sample is deposited onto the test chamber, the applied voltage physically transforms the analyte in the sample into a different form due to the enzymatic reaction of the analyte with the reagent in the test chamber. As the sample flows into the capillary channel of the test cell, at least one physical characteristic of the sample is obtained (step 908C). In particular, the step of obtaining or measuring the physical characteristic (step 908C) may include applying a first signal to the sample to derive a physical characteristic of the sample, while the step 906C of initiating an enzymatic reaction (e.g., by applying signals to the sample and reagent) may involve driving a second signal to the sample, and the step of measuring (step 912C) may entail measuring an output signal from the at least two electrodes at a point in time after the start of the test sequence, in which a sampling time point is specified (at step 909) and a batch slope (step 910C) is derived and as a function of at least the measured or estimated physical characteristic (step 908C).

In a variation of the method, the step of applying of the first signal involves directing an alternating signal provided by an appropriate power source (e.g., the meter 200) to the sample so that a physical characteristic of the sample is determined from an output of the alternating signal. The physical characteristic being detected may be one or more of viscosity, hematocrit or density. The directing step may include driving first and second alternating signal at different respective frequencies in which a first frequency is lower than the second frequency. Preferably, the first frequency is at least one order of magnitude lower than the second frequency. As an example, the first frequency may be any frequency in the range of about 10 kHz to about 100 kHz and the second frequency may be from about 250 kHz to about 1 MHz or more. As used herein, the phrase "alternating signal" can have some portions of the signal alternating in polarity or all alternating current signal or an alternating current with a direct current offset or even a multi-directional signal combined with a direct-current signal.

Once the physical characteristic of the sample is determined or obtained from a suitable technique, the physical characteristic can be used to specify a sampling time point (step 909) at which point during the test sequence the output signal of the test chamber could be measured. In particular, applicants have found a relationship between the physical characteristic and the sampling time point, as shown here in FIG. 7. This relationship has been further explored such that applicants were able to derive a direct relationship between the sampling time point of the sample and the physical characteristic of the sample (e.g., hematocrit), shown here in FIG. 6C2. As a consequence, by knowing the physical characteristic of the sample (e.g., hematocrit) from Equation 4 above, the relationship in FIG. 6C2 can be exploited to allow the sampling time point to be specified to accommodate the different levels of physical characteristic (e.g., hematocrit) so as to achieve much more accurate analyte (e.g., glucose) concentration measurements.

Referring back to FIG. 7, it can be seen that as the analyte concentration (proportional to the signal output) increases, the peak of the high glucose concentration (denoted by 1002a, 1004a, and 1006a) is shifted to the right as compared to the medium glucose concentration (denoted by 1002b, 1004b, and 1006b). Similarly, the peak of the medium glucose concentration is further to the right of FIG. 7 as compared to low glucose concentration (denoted by 1002c, 1004c, and 1006c). It can also be seen here that the steady-state of the low glucose concentrations (1002c, 1004c, and 1006c) is reached earlier than the medium glucose concentrations (1002b, 1004b, and 1006b). This pattern is repeated for high glucose concentration (1002a, 1004a, and 1006b) as compared to medium glucose concentrations.

Although the method may specify only one sampling time point, the method may include sampling as many time points as required, such as, for example, sampling the signal output continuously (e.g., at specified sampling time such as, every one millisecond to 100 milliseconds) from the start of the test sequence until at least about 10 seconds after the start and the results stored for processing near the end of the test sequence. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. In this variation, the sampled signal output at the specified sampling time T is the value used to calculate the analyte concentration.

Alternatively, a look-up table, represented exemplarily here with reference to Table 1 can also be utilized in place of Equation 7 or in addition to Equation 7 to determine the appropriate sampling time point T. In Table 1, the value of the physical characteristic is used by the processor of the system to look up the appropriate time at which the signal output of the biosensor is sampled or measured to determine the analyte concentration. For example, once the physical characteristic has been determined, in this case about 33% hematocrit, the time at which the signal output of the biosensor 100 is utilized in determining the analyte concentration can be gleaned from Table 1, which shows that the time at which the system must sample the signal output is at approximately 5.32 seconds after the start of the test sequence.

To further improve the accuracy of the results, the method may entail evaluating an output signal from the at least two electrodes at a point in time after the start of the test sequence, in which a new batch slope is derived (at step 910C) as a function of at least the measured or estimated physical characteristic (step 908C).

The setting of a new batch slope (step 910C) to derive a more accurate analyte concentration measurement merits a discussion with reference to FIGS. 7 and 6C3. Applicants have further found that another relationship exists between the batch slope of these test strips tested at the Lo-G, Mid-G, and Hi-G levels with respect to 30%, 42%, and 55% hematocrit levels of FIG. 7. In particular, applicants have found that the batch slope for these strips is generally curved with respect to hematocrit level, shown here in FIG. 6C3. In FIG. 6C3, the batch slope declines in a generally curved manner at low (e.g., 30%), medium (e.g., 42%), and high (e.g., 55%) hematocrits. As a consequence, by knowing the physical characteristic of the sample (e.g., hematocrit) from Equation 4 above, the relationship in FIG. 6C3 can be exploited to allow the slope in Equation 3.3 to be calculated for the different levels of physical characteristic (e.g., hematocrit) so as to achieve much more accurate glucose concentration measurements.

It should be noted that while slope "x" in FIG. 6C3 appears to be a linear line, slope "x" is in fact a curved line and a curve has been fitted for the relationship between physical characteristic (e.g., hematocrit) and slope implicit in FIG. 6C3. This fitted curve for FIG. 6C3 was found by applicants and defined in Equation 5 previously. It is noted that due to an adjustment at which the sampling time was taken for the embodiment described herein, Equation 5 is preferably used with the following coefficients: a is about −1.98e−6; b is about −2.87e−5; and c is about 2.67e−2 and ±10% for each of the magnitudes provided. The adjustment stems from the fact that the new coefficients (a, b, and c) are calculated at different sampling time, whereas before, the sampling time was fixed at about 5 seconds. This will cause coefficients a, b and c to be different in order to maximise accuracy. If one skilled in the art were to use the same coefficients a, b and c as before, such skilled person can still obtain the analyte concentration but the resulting estimates will deteriorate. The driver here is that slope of glucose relation to haematocrit is changing within the signal transient, so different slopes are needed as the sampling time is varied between about 3.5 seconds to about 6 seconds.

It is noted that Equation 5 can be used instead of plotting against FIG. 6C3, depending on the available computing power of the processor. Continuing on with the exemplary process of FIG. 6C1, once the physical characteristic is known at step 908C from Equation 4, such as for example Hct~55%, the graph of FIG. 6C3 or Equation 5 is utilized to determine the appropriate batch slope, designated here as "NewSlope" which is about 0.019. Alternatively, Equation 5 can be utilized to derive the NewSlope from the measured or estimated physical characteristic (e.g., hematocrit). This NewSlope (from FIG. 6C3 or Eq. 5) is used along with the batch intercept (Intercept) with the sampling time relationship that applicants have found, as set forth previously with respect to Eq. 5.

Referring back to FIG. 6C1, the method can now determine the analyte concentration (step 914C) based on a new batch slope (i.e., NewSlope) derived from the measured or estimated physical characteristic of the sample (at step 910C) along with the measured signal (step 912C) sampled at the specified time point (at step 909), which specified time point is a function of the obtained or measured or estimated physical characteristic of the sample (e.g., from plot of FIG. 6C2 or Equation 5). That is, once the sampling time has been specified from Equation 5 and the NewSlope from Equation 6, the method provides for measuring the output signal from the test chamber (e.g., chamber 92) so that the sampled output can be utilized with Equation 3.3 to provide for an analyte (e.g., glucose) concentration.

In one embodiment the analyte (e.g., glucose) concentration is determined based on a modified form of Equation 3.3, delineated here as Equation 8:

$$G_0 = \left[\frac{I_E - \text{Intercept}}{\text{NewSlope}}\right] \quad \text{Eq. 8}$$

where
$G_0$ represents an analyte concentration
$I_E$ is a signal (proportional to analyte concentration) as measured at the specified SamplingTime point;
"NewSlope" is the value obtained from the relationship in FIG. 6C3 or from Eq. 5;
Intercept is the value obtained from calibration testing of a batch of test strips of which this particular strip comes from.
Once the signal output $I_E$ of the test chamber is measured at the specified time (step 909) at any point between about 3 seconds to about 8 seconds, the signal $I_E$ is thereafter used with the NewSlope (of the batch) and Intercept (of the batch) in the calculation of the analyte concentration (in this case glucose) with Eq. 8 above. Intercept comprises a manufacturing parameter for a batch of biosensors, and in the embodiments described herein, Intercept typically varies from about 0.7 to about 0.6. It should be noted that the step of applying the first signal and the driving of the second signal is in sequential order in that the order may be the first signal then the second signal or both signals overlapping in sequence; alternatively, the second signal first then the first signal or both signals overlapping in sequence. Alternatively, the applying of the first signal and the driving of the second signal may take place simultaneously.

It is noted that in the preferred embodiments, the measurement of a signal output for the analyte (e.g., glucose) concentration is performed prior to the estimation of the physical characteristic (e.g., hematocrit). Alternatively, the physical characteristic (e.g., hematocrit) level can be estimated, measured, or obtained prior to the measurement of the analyte (e.g., glucose) concentration.

Thus, as another benefit of the teaching provided herein, a method of demonstrating increased accuracy of a test strip is heretofore is achieved. This method involves providing for a batch of test strips, typically in a batch of at least about 1500 test strips (and in some cases up to 1 million test strips per batch), introducing a referential sample containing a referential concentration of an analyte to each of the batch of test strips to initiate a test sequence. The method involves reacting the analyte to cause a physical transformation of the analyte with the reagent between the two electrodes, determining a physical characteristic of the referential sample, deriving a batch slope for the test strip, sampling an electrical output of the referential sample at a specified time point during the test sequence defined by the measured or estimated physical characteristic of the sample, and calculating an analyte concentration based on the dictated time and the derive batch slope such that at least 95% of the analyte concentration values of the batch of test strips are within about ±15% of the referential analyte concentration for the range of hematocrit from about 30% to about 55%, shown here in FIG. 6C4.

As can be seen in FIG. 6C4, most or virtually all of the glucose concentration using this technique are within about ±15% bias for hematocrit from about 30% hematocrit to about 55% hematocrit. Specifically, at region 1010C, none of the glucose concentration greater than 100 mg/dL is outside the bias of −15%; at region 1012C of intermediate hematocrit, a few glucose concentrations are outside the bias range of 15% and at region 1014C of high hematocrit, a few more glucose concentrations are dispersed outside the bias of 15% as compared to regions 1010C and 1012C.

Yet a further technique can be understood with reference to FIG. 6D1. This technique involves depositing a fluid sample (which may be a physiological sample) on a biosensor at step 904 (e.g., in the form of a test strip as show in FIG. 3A(1), 3A(2), or 3A(3)-3T) that has been inserted into a meter (step 902). Once the meter 200 is turned on, a voltage is applied to the strip 100 (or its variants 400, 500, or 600) and when the sample is deposited onto the test chamber, the applied signal physically transforms the analyte in the sample into a different form due to the enzymatic reaction of the analyte with the reagent in the test chamber. As the sample flows into the capillary channel of the test cell, at least one physical characteristic of the sample is obtained (step 908) along with estimate of the analyte concentration (step 910). From the obtained physical characteristic (step 908) and estimated analyte concentration (step 910), a sampling time point is defined at which the signal output from the sample during the test sequence is measured (at step 914) and used for calculating the analyte concentration in step 916. In particular, the step of obtaining the physical characteristic (step 908) may include applying a first signal to the sample to measure a physical characteristic of the sample, while the step 906 of initiating an enzymatic reaction may involve driving a second signal to the sample, and the step of measuring (step 914) may entail evaluating an output signal from the at least two electrodes at a point in time after the start of the test sequence, in which the point in time is set (at step 912) as a function of at least the measured or estimated physical characteristic (step 908) and estimated analyte concentration (step 910).

The determination of the appropriate point in time as a function of the measured or estimated physical characteristic(s) in step 912 can be determined by the use of a look-up table programmed into the microprocessor of the system. For example, a look-up table may be provided that allows for the system to select the appropriate sampling time for the analyte (e.g., glucose or ketone) with measured or known physical characteristic (e.g., hematocrit or viscosity) of the sample.

In particular, an appropriate sampling time point may be based on an early estimation of the analyte and the measured or known physical characteristic to arrive at the appropriate sampling time that gives the lowest error or bias as compared to referential values. In this technique, a look up table is provided in which the defined sampling time point is correlated to (a) the estimated analyte concentration and (b) the physical characteristic of the sample. For example, Table 2 may be programmed into the meter to provide a matrix in which qualitative categories (low, medium, and high glucose) of the estimated analyte form the main column and the qualitative categories (low, medium, and high) of the measured or estimated physical characteristic form the header row. In the second column, t/Hct is a value determined experimentally of the time shift per % hematocrit difference from nominal hematocrit of 42%. As one example, for 55% hematocrit at "Mid-Glucose" would indicate a time shift of (42−55)*90=−1170 ms. The time of −1170 milliseconds is added to the original test time of about 5000 milliseconds giving (5000−1170=3830 milliseconds)~3.9 seconds.

TABLE 2

| Estimated Analyte | t/Hct (in milli-seconds) | Sampling Time Point T for Lo Hct (from start of test sequence, in seconds) | Sampling Time Point T for Mid Hct (from start of test sequence, in seconds) | Sampling Time Point T for High Hct (from start of test sequence, in seconds) |
|---|---|---|---|---|
| Lo-Glucose | 40 | 5.5 | 5 | 4.5 |
| Mid-Glucose | 90 | 6.1 | 5 | 3.9 |
| Hi-Glucose | 110 | 6.3 | 5 | 3.6 |

The time T at which the system should be sampling the output signal of the biosensor is based on both the qualitative category of the estimated analyte and measured or estimated physical characteristic and is predetermined based on regression analysis of a large sample size of actual physiological fluid samples. Applicants note that the appropriate sampling time is measured from the start of the test sequence but any appropriate datum may be utilized in order to determine when to sample the output signal. As a practical matter, the system can be programmed to sample the output signal at an appropriate time sampling interval during the entire test sequence such as for example, one sampling every 100 milliseconds or even as little as about 1 milliseconds. By sampling the entire signal output transient during the test sequence, the system can perform all of the needed calculations near the end of the test sequence rather than attempting to synchronize the sampling time with the set time point, which may introduce timing errors due to system delay.

Applicants hereafter will discuss the look-up Table 2 in relation to the particular analyte of glucose in physiological fluid samples. Qualitative categories of blood glucose are defined in the first column of Table 2 in which low blood glucose concentrations of less than about 70 mg/dL are designated as "Lo-Glucose"; blood glucose concentrations of higher than about 70 mg/dL but less than about 250 mg/dL are designated as "Mid-Glucose"; and blood glucose concentrations of higher than about 250 mg/dL are designated as "Hi-Glucose".

During a test sequence, an "Estimated Analyte" can be obtained by sampling the signal at a convenient time point, typically at five seconds during a typical 10 seconds test sequence. The measurement sampled at this five second time point allows for an accurate estimate of the analyte (in this case blood glucose). The system may then refer to a look-up table (e.g., Table 2) to determine when to measure the signal output from the test chamber at a specified sampling time T based on two criteria: (a) estimated analyte and (b) qualitative value of the physical characteristic of the sample. For criteria (b), the qualitative value of the physical characteristic is broken down into three sub-categories of Low Hct, Mid Hct and High Hct. Thus, in the event that the measured or estimated physical characteristic (e.g., hematocrit) is high (e.g., greater than 46%) and the estimated glucose is also high, then according to Table 2, the test time for the system to measure the signal output of test chamber would be about 3.6 seconds. On the other hand, if the measured hematocrit is low (e.g., less than 38%) and the estimated glucose is low then according to Table 2, the test time T for the system to measure the signal output of test chamber would be about 5.5 seconds.

Once the signal output $I_T$ of the test chamber is measured at the designated time (which is governed by the measured or estimated physical characteristic), the signal $I_T$ is thereafter used in the calculation of the analyte concentration (in this case glucose) with Equation 9 below.

$$G_0 = \left[\frac{I_T - \text{Intercept}}{\text{Slope}}\right] \quad \text{Eq. 9}$$

where $G_0$ represents an analyte concentration;

$I_T$ represents a signal (proportional to analyte concentration) determined from the sum of the end signals measured at a specified sampling time T, which may be the total current measured at the specified sampling time T;

Slope represents the value obtained from calibration testing of a batch of test strips of which this particular strip comes from and is typically about 0.02; and Intercept represents the value obtained from calibration testing of a batch of test strips of which this particular strip comes from and is typically from about 0.6 to about 0.7.

It should be noted that the step of applying the first signal and the driving of the second signal is sequential in that the order may be the first signal then the second signal or both signals overlapping in sequence; alternatively, the second signal first then the first signal or both signals overlapping in sequence. Alternatively, the applying of the first signal and the driving of the second signal may take place simultaneously.

In the method, the step of applying of the first signal involves directing an alternating signal provided by an appropriate power source (e.g., the meter 200) to the sample so that a physical characteristic of the sample is determined from an output of the alternating signal. The physical characteristic being detected may be one or more of viscosity, hematocrit or density. The directing step may include driving first and second alternating signal at different respective frequencies in which a first frequency is lower than the second frequency. Preferably, the first frequency is at least one order of magnitude lower than the second frequency. As an example, the first frequency may be any frequency in the range of about 10 kHz to about 100 kHz and the second frequency may be from about 250 kHz to about 1 MHz or more. As used herein, the phrase "alternating signal" or "oscillating signal" can have some portions of the signal alternating in polarity or all alternating current signal or an alternating current with a direct current offset or even a multi-directional signal combined with a direct-current signal.

Further refinements of Table 2 based on additional investigations of the technique allowed applicants to devise Table 3, shown below.

TABLE 3

Sampling Time S to Estimated G and Measured or Estimated Physical Characteristic

| Estimated G | Measured or Estimated Physical Characteristic (e.g., HCT [%]) | | | | | | | | | | | | |
|---|---|---|---|---|---|---|---|---|---|---|---|---|---|
| [mg/dL] | 24 | 27 | 30 | 33 | 36 | 39 | 42 | 45 | 48 | 51 | 54 | 57 | 60 |
| 25 | 4.6 | 4.6 | 4.5 | 4.4 | 4.4 | 4.4 | 4.3 | 4.3 | 4.3 | 4.2 | 4.1 | 4.1 | 4.1 |
| 50 | 5 | 4.9 | 4.8 | 4.7 | 4.7 | 4.6 | 4.5 | 4.4 | 4.3 | 4.2 | 4.1 | 4 | 4 |
| 75 | 5.3 | 5.3 | 5.2 | 5 | 4.9 | 4.8 | 4.7 | 4.5 | 4.4 | 4.3 | 4.1 | 4 | 3.8 |
| 100 | 5.8 | 5.6 | 5.4 | 5.3 | 5.1 | 5 | 4.8 | 4.6 | 4.4 | 4.3 | 4.1 | 3.9 | 3.7 |
| 125 | 6.1 | 5.9 | 5.7 | 5.5 | 5.3 | 5.1 | 4.9 | 4.7 | 4.5 | 4.3 | 4.1 | 3.8 | 3.6 |
| 150 | 6.4 | 6.2 | 5.9 | 5.7 | 5.5 | 5.3 | 5 | 4.8 | 4.6 | 4.3 | 4 | 3.8 | 3.5 |
| 175 | 6.6 | 6.4 | 6.2 | 5.9 | 5.6 | 5.4 | 5.2 | 4.9 | 4.6 | 4.3 | 4 | 3.7 | 3.4 |
| 200 | 6.8 | 6.6 | 6.4 | 6.1 | 5.8 | 5.5 | 5.2 | 4.9 | 4.6 | 4.3 | 4 | 3.7 | 3.4 |
| 225 | 7.1 | 6.8 | 6.5 | 6.2 | 5.9 | 5.6 | 5.3 | 5 | 4.7 | 4.3 | 4 | 3.6 | 3.2 |
| 250 | 7.3 | 7 | 6.7 | 6.4 | 6 | 5.7 | 5.3 | 5 | 4.7 | 4.3 | 4 | 3.6 | 3.2 |
| 275 | 7.4 | 7.1 | 6.8 | 6.4 | 6.1 | 5.8 | 5.4 | 5 | 4.7 | 4.3 | 4 | 3.5 | 3.2 |
| 300 | 7.5 | 7.1 | 6.8 | 6.5 | 6.2 | 5.8 | 5.5 | 5.1 | 4.7 | 4.3 | 4 | 3.5 | 3.1 |
| w325 | 7.6 | 7.3 | 6.9 | 6.5 | 6.2 | 5.8 | 5.5 | 5.1 | 4.7 | 4.3 | 3.9 | 3.5 | 3.1 |
| 350 | 7.6 | 7.3 | 7 | 6.6 | 6.2 | 5.8 | 5.5 | 5.1 | 4.7 | 4.3 | 3.9 | 3.5 | 3.1 |
| 375 | 7.7 | 7.3 | 7 | 6.6 | 6.2 | 5.8 | 5.5 | 5.1 | 4.7 | 4.3 | 3.9 | 3.5 | 3.1 |
| 400 | 7.7 | 7.3 | 6.9 | 6.5 | 6.2 | 5.8 | 5.4 | 5 | 4.7 | 4.3 | 3.9 | 3.5 | 3.1 |
| 425 | 7.6 | 7.3 | 6.9 | 6.5 | 6.2 | 5.8 | 5.4 | 5 | 4.6 | 4.3 | 3.8 | 3.5 | 3.1 |
| 450 | 7.6 | 7.2 | 6.8 | 6.4 | 6.1 | 5.7 | 5.3 | 5 | 4.6 | 4.3 | 3.8 | 3.5 | 3.1 |
| 475 | 7.4 | 7.1 | 6.7 | 6.4 | 6 | 5.6 | 5.3 | 4.9 | 4.6 | 4.2 | 3.8 | 3.5 | 3.1 |
| 500 | 7.3 | 7 | 6.6 | 6.2 | 5.9 | 5.5 | 5.2 | 4.9 | 4.5 | 4.1 | 3.8 | 3.5 | 3.2 |
| 525 | 7.1 | 6.8 | 6.5 | 6.1 | 5.8 | 5.5 | 5.1 | 4.8 | 4.4 | 4.1 | 3.8 | 3.5 | 3.2 |
| 550 | 7 | 6.7 | 6.3 | 5.9 | 5.6 | 5.3 | 5 | 4.7 | 4.4 | 4.1 | 3.8 | 3.5 | 3.2 |
| 575 | 6.8 | 6.4 | 6.1 | 5.8 | 5.5 | 5.2 | 4.9 | 4.6 | 4.3 | 4.1 | 3.8 | 3.5 | 3.4 |
| 600 | 6.5 | 6.2 | 5.9 | 5.6 | 5.3 | 5 | 4.7 | 4.5 | 4.3 | 4 | 3.8 | 3.6 | 3.4 |

As in Table 2, a measured or estimated physical characteristic is used in Table 3 along with an estimated analyte concentration to derive a time S at which the sample is to be measured. For example, if the measured characteristic is about 30% and the estimated glucose (e.g., by sampling at about 2.5 to 3 seconds) is about 350, the time at which the microcontroller should sample the fluid is about 7 seconds. In another example, where the estimated glucose is about 300 mg/dL and the measured or estimated physical characteristic is 60%, specified sampling time would be about 3.1 seconds.

For the embodiments utilized with Table 3, the estimated glucose concentration is provided with an equation:

$$G_{est} = \frac{(I_E - x_2)}{x_1} \qquad \text{Eq. 10}$$

where $G_{est}$ represents the estimated glucose concentration;
$I_E$ is the signal measured at about 2.5 seconds;
$x_1$ is the slope (e.g., $x_1$=1.3e01);
$x_2$ is the intercept (e.g., $x_2$=6.9e02)

From the estimated glucose, the glucose concentration can be determined from:

$$G_o = \frac{(I_s - x_4)}{x_3} \qquad \text{Eq. 11}$$

where:

$G_O$ represents the glucose concentration;
$I_S$ is the signal measured at a specified sampling time S from Table 3;
$x_3$ is the slope (e.g., $x_3$=9.6); and
$x_4$ is the intercept (e.g., $x_4$=4.8e02).

Although the method may specify only one sampling time point, the method may include sampling as many time points as required, such as, for example, sampling the signal output continuously (e.g., at specified sampling time such as, every 1 milliseconds to 100 milliseconds) from the start of the test sequence until at least about 10 seconds after the start and the results stored for processing near the end of the test sequence. In this variation, the sampled signal output at the specified sampling time (which may be different from the predetermined sampling time point) is the value used to calculate the analyte concentration.

It is noted that in the preferred embodiments, the measurement of a signal output for the value that is somewhat proportional to analyte (e.g., glucose) concentration is performed prior to the estimation of the hematocrit. Alternatively, the hematocrit level can be estimated prior to the measurement of the preliminary glucose concentration. In either case, the estimated glucose measurement $G_E$ is obtained by Equation 3.3 with $I_E$ sampled at about one of 2.5 seconds or 5 seconds, as in FIG. 6D2, the physical characteristic (e.g., Hct) is obtained by Equation 4 and the glucose measurement G is obtained by using the measured signal output $I_D$ at the designated sampling time point(s) (e.g., the measured signal output $I_D$ being sampled at 3.5 seconds or 6.5 seconds) for the signal transient 1000.

Thus, as another benefit of the teaching provided herein, a method of demonstrating increased accuracy of a test strip is heretofore is achieved. This method involves providing for a batch of test strips, typically in a batch of at least about 1500 test strips (and up to a million or more test strips in certain cases), introducing a referential sample containing a referential concentration of an analyte to each of the batch of test strips to initiate a test sequence. The method involves, reacting the analyte to cause a physical transformation of the analyte with the reagent between the two electrodes, determining a physical characteristic of the referential sample, estimating the analyte concentration, sampling an electrical output of the referential sample at a dictated time point during the test sequence defined by the measured or estimated physical characteristic of the sample and the estimated analyte concentration, and calculating an analyte concentration based on the dictated time such that at least 95% of the analyte concentration values of the batch of test strips are within ±10% of the referential analyte concentration for the range of hematocrit from about 30% to about 55%, shown here in FIG. 6D3.

In FIG. 6D3, experiments were performed to quantify the improvement in the glucose measurements from the method noted above. The quantification of the improvement can be shown by the "bias" at different levels of hematocrit. The bias, which is an estimate of the relative error in the glucose measurement, was calculated for each glucose concentration determined with the method described in this example.

As can be seen in FIG. 6D3, most or virtually all of the glucose concentration using this technique are within about ±10% bias for hematocrit from about 30% hematocrit to about 55% hematocrit. This is believed to be a breakthrough as the prior technique of sampling the output signal transient at a fixed time point (typically at about one of 2.5 seconds or 5 seconds from the start of test sequence) for this specific type of test strip generally fails to show any bias of less than ±20%.

By virtue of the descriptions and teachings provided herein, we were able to devise a glucose test strip that has a substrate, a plurality of electrodes disposed on the substrate and connected to respective electrode connectors. The test strip 100 includes at least a reagent disposed on at least one of the plurality of electrodes, in which at least one of the electrodes is configured to sense a physical characteristic of fluid sample deposited on the at least one electrode and at least another of the electrodes is configured to measure output signal from the sample upon application of input signal to the sample. Included with the test strip are instructions for use with a glucose meter. The instructions include indicia embedded in an appropriate communication medium (e.g., paper, computer, internet, audio or visual medium or the like) to a user to insert the electrode connectors of the test strip to a test strip port of the glucose meter. The meter indicated for use with the glucose test strip includes a test strip port connector configured to connect to respective electrode connectors of a test strip, and a microprocessor in electrical communication with the test strip port connector to apply electrical signals or sense electrical signals from a plurality of electrodes of the test strip connected to the respective electrode connectors of the test strip during a test sequence. The instructions further include indicia embedded in an appropriate communication medium (e.g., paper, computer, internet, audio or visual medium or the like) to the user to deposit a fluid sample proximate at least one of the plurality of electrodes so that the microprocessor 300 is operable to: (a) apply a first signal to the plurality of electrodes so that a physical characteristic of a fluid sample deposited on the plurality of electrodes is determined; (b) estimate an analyte concentration based on a predetermined sampling time point during a test sequence; and (c) apply a second signal to the plurality of electrodes at a sampling time point during the test sequence dictated by the determined physical characteristic so that an analyte concentration is calculated from the second signal.

Similarly, we were able to devise a glucose test strip 100 that has a substrate, a plurality of electrodes disposed on the substrate and connected to respective electrode connectors. The test strip includes at least a reagent disposed on at least one of the plurality of electrodes, in which at least one of the electrodes is configured to sense a physical characteristic of fluid sample deposited on the at least one electrode and at least another of the electrodes is configured to measure output signal from the sample upon application of input signal to the sample. Included with the test strip are instructions for use with a glucose meter. The instructions includes indicia embedded in an appropriate communication medium (e.g., paper, computer, internet, audio or visual means and the like) to a user to insert the electrode connectors of the test strip to a test strip port of the glucose meter. The meter indicated for use with the glucose test strip includes a test strip port connector configured to connect to respective electrode connectors of a test strip, and a microprocessor in electrical communication with the test strip port connector to apply electrical signals or sense electrical signals from a plurality of electrodes of the test strip connected to the respective electrode connectors of the test strip during a test sequence. The instructions further include indicia to the user to deposit a fluid sample proximate at least one of the plurality of electrodes so that the microprocessor is operable to: (a) apply a first signal to the plurality of electrodes so that a specific sampling time determined from a physical characteristic of a fluid sample is derived, (b) apply a second signal to the plurality of electrodes, and (c) measure a signal output from one of the plurality of electrodes at the specified sampling time so that an analyte concentration is determined.

Likewise, we were able to devise a glucose test strip that has a substrate, a plurality of electrodes disposed on the substrate and connected to respective electrode connectors. The test strip includes at least a reagent disposed on at least one of the plurality of electrodes, in which at least one of the electrodes is configured to sense a physical characteristic of fluid sample deposited on the at least one electrode and at least another of the electrodes is configured to measure output signal from the sample upon application of input signal to the sample. Included with the test strip are instructions for use with a glucose meter. The instructions includes indicia embedded in an appropriate communication medium (e.g., paper, computer, internet, audio or visual means and the like) to a user to insert the electrode connectors of the test strip to a test strip port of the glucose meter. The meter indicated for use with the glucose test strip includes a test strip port connector configured to connect to respective electrode connectors of a test strip, and a microprocessor in electrical communication with the test strip port connector to apply electrical signals or sense electrical signals from a plurality of electrodes of the test strip connected to the respective electrode connectors of the test strip during a test sequence. The instructions further include indicia to the user to deposit a fluid sample proximate at least one of the plurality of electrodes so that the microprocessor is operable to: (a) apply a first signal to the plurality of electrodes so that a specified sampling time and a batch slope determined from a physical characteristic of a fluid sample are derived, (b) apply a second signal to the plurality of electrodes, and (c) measure a signal output from one of the plurality of electrodes at the specified sampling time so that an analyte concentration is determined based on the measured signal at the specified sampling time and the batch slope.

Similarly, applicant was able to devise a glucose test strip that has a substrate, a plurality of electrodes disposed on the substrate and connected to respective electrode connectors. The test strip includes at least a reagent disposed on at least one of the plurality of electrodes, in which at least one of the electrodes is configured to sense a physical characteristic of fluid sample deposited on the at least one electrode and at least another of the electrodes is configured to measure output signal from the sample upon application of input signal to the sample. Included with the test strip are instructions for use with a glucose meter. The instructions include indicia embedded in an appropriate communication medium (e.g., paper, computer, internet, audio or visual means and the like) to a user to insert the electrode connectors of the test strip to a test strip port of the glucose meter. The meter indicated for use with the glucose test strip includes a test strip port connector configured to connect to respective electrode connectors of a test strip, and a microprocessor in electrical communication with the test strip port connector to apply electrical signals or sense electrical signals from a plurality of electrodes of the test strip connected to the respective electrode connectors of the test strip during a test sequence. The instructions further include indicia to the user to deposit a fluid sample proximate at least one of the plurality of electrodes so that the microprocessor is operable to: (a) apply a first signal to the plurality of electrodes so that a batch slope defined by a physical characteristic of a fluid sample is derived, and (b) apply a second signal to the plurality of electrodes so that an analyte concentration is determined based on the derived batch slope.

Although the techniques described herein have been directed to determination of glucose, the techniques can also be applied to other analytes (with appropriate modifications by those skilled in the art) that are affected by physical characteristic(s) of the fluid sample in which the analyte(s) is disposed in the fluid sample. For example, the physical characteristic (e.g., hematocrit, viscosity or density and the like) of a physiological fluid sample could be accounted for in determination of ketone or cholesterol in the fluid sample, which may be physiological fluid, calibration, or control fluid. Other biosensor configurations can also be utilized. For example, the biosensors shown and described in the following US Patents can be utilized with the various embodiments described herein: U.S. Pat. Nos. 6,179,979; 6,193,873; 6,284,125; 6,413,410; 6,475,372; 6,716,577; 6,749,887; 6,863,801; 6,890,421; 7,045,046; 7,291,256; 7,498,132, all of which are incorporated by reference in their entireties herein.

As is known, the detection of the physical characteristic does not have to be done by alternating signals but can be done with other techniques. For example, a suitable sensor can be utilized (e.g., US Patent Application Publication No. 20100005865 or EP1804048 B1) to determine the viscosity or other physical characteristics. Alternatively, the viscosity can be determined and used to derive for hematocrits based on the known relationship between hematocrits and viscosity as described in "Blood Rheology and Hemodynamics" by Oguz K. Baskurt, M.D., Ph.D., 1 and Herbert J. Meiselman, Sc. D., *Seminars in Thrombosis and Hemostasis*, volume 29, number 5, 2003.

As described earlier, the microcontroller or an equivalent microprocessor (and associated components that allow the microcontroller to function for its intended purpose in the intended environment such as, for example, the processor 300 in FIG. 2B) can be utilized with computer codes or software instructions to carry out the methods and techniques described herein. Applicants note that the exemplary microcontroller 300 (along with suitable components for functional operation of the processor 300) in FIG. 2B is embedded with firmware or loaded with computer software representative of the logic diagrams in FIG. 6A(1), 6B(1); 6C(1); or 6D(1) and the microcontroller 300, along with associated connector 220 and interface 306 and equivalents thereof, are the means for: (a) determining a specified sampling time based on a sensed or estimated physical characteristic, the specified sampling time being at least one time point or interval referenced from a start of a test sequence upon deposition of a sample on the test strip and (b) determining an analyte concentration based on the specified sampling time. Alternatively, the means for determining may include means for applying a first signal to the plurality of electrodes so that a batch slope defined by a physical characteristic of a fluid sample is derived and for applying a second signal to the plurality of electrodes so that an analyte concentration is determined based on the derived batch slope and the specified sampling time. Furthermore, the means for determining may include means for estimating an analyte concentration based on a predetermined sampling time point from the start of the test sequence and for selecting a specified sampling time from a matrix of estimated analyte concentration and sensed or estimated physical characteristic. Yet further, the means for determining may include means for selecting a batch slope based on the sensed or estimated physical characteristic and for ascertaining the specified sampling time from the batch slope.

A short discussion of the embodiments of the meter for the present disclosure is worthwhile at this point. In particular, hand-held test meters for use with an analytical test strip in the determination of an analyte (such as glucose) in a bodily fluid sample (i.e., a whole blood sample) according to embodiments of the present disclosure include a housing, a microcontroller block disposed in the housing, and a phase-shift-based hematocrit measurement block (also referred to as a phase-shift-based hematocrit circuit). In such hand-held test meters, the phase-shift-based hematocrit measurement block includes a signal generation sub-block, a low pass filter sub-block, an analytical test strip sample cell interface sub-block, a transimpedance amplifier sub-block, and a phase detector sub-block. In addition, the phase-shift-based hematocrit measurement block and microcontroller block are configured to measure the phase shift of a bodily fluid sample in a sample cell of an analytical test strip inserted in the hand-held test meter and the microcontroller block is also configured to compute the hematocrit of the bodily fluid sample based on the measured phase shift.

Hand-held test meters according to embodiments of the present disclosure are beneficial in that they provide improved accuracy of analyte determination (such as glucose determination) in whole blood samples by measuring the hematocrit of the whole blood sample and then employing the measured hematocrit during analyte determination.

Once one skilled in the art is apprised of the present disclosure, he or she will recognize that an example of a hand-held test meter that can be readily modified as a hand-held test meter according to the present disclosure is the commercially available OneTouch® Ultra® 2 glucose meter from LifeScan Inc. (Milpitas, Calif.). Additional examples of hand-held test meters that can also be modified are found in U.S. Patent Application Publications Nos. 2007/0084734 (published on Apr. 19, 2007) and 2007/0087397 (published on Apr. 19, 2007) and in International Publication Number WO2010/049669 (published on May 6, 2010), each of which is hereby incorporated herein in full by reference.

Figure 8:
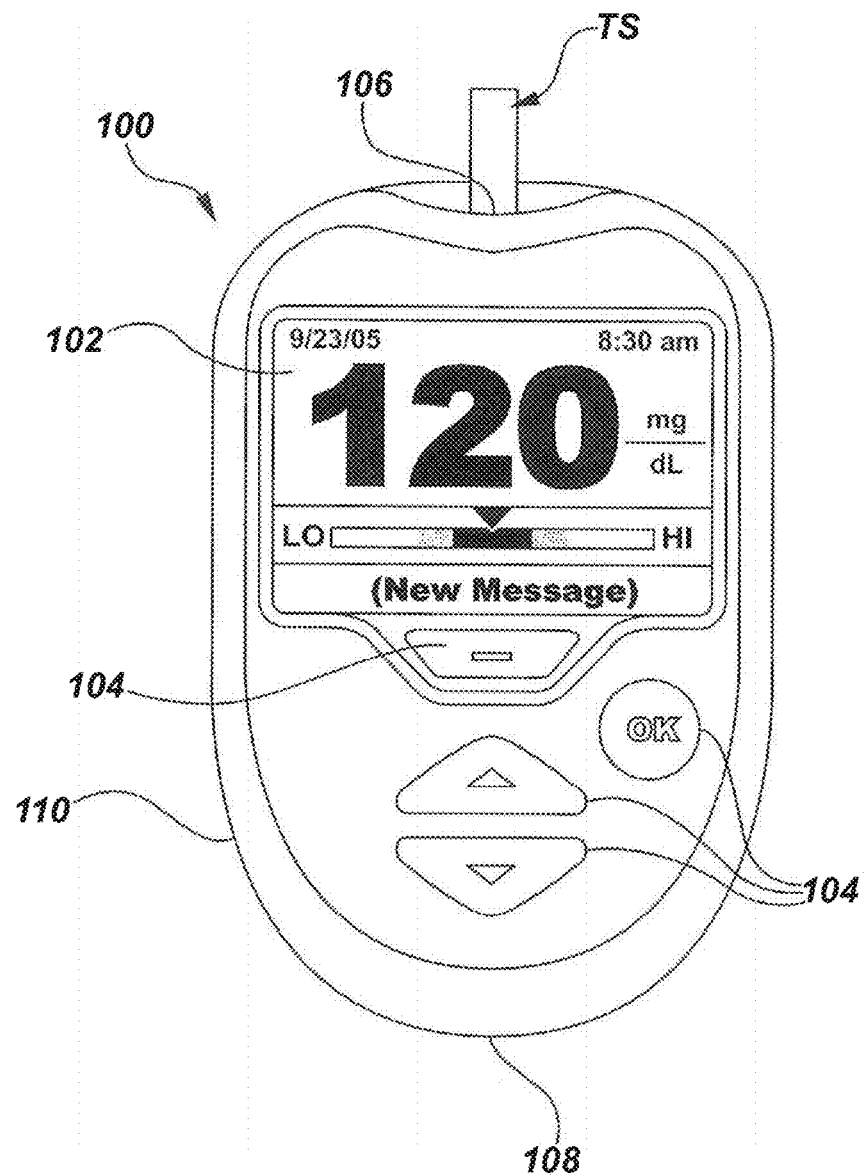
FIG. 8 is a simplified depiction of a hand-held test meter according to an embodiment of the present disclosure.
Figure 9:
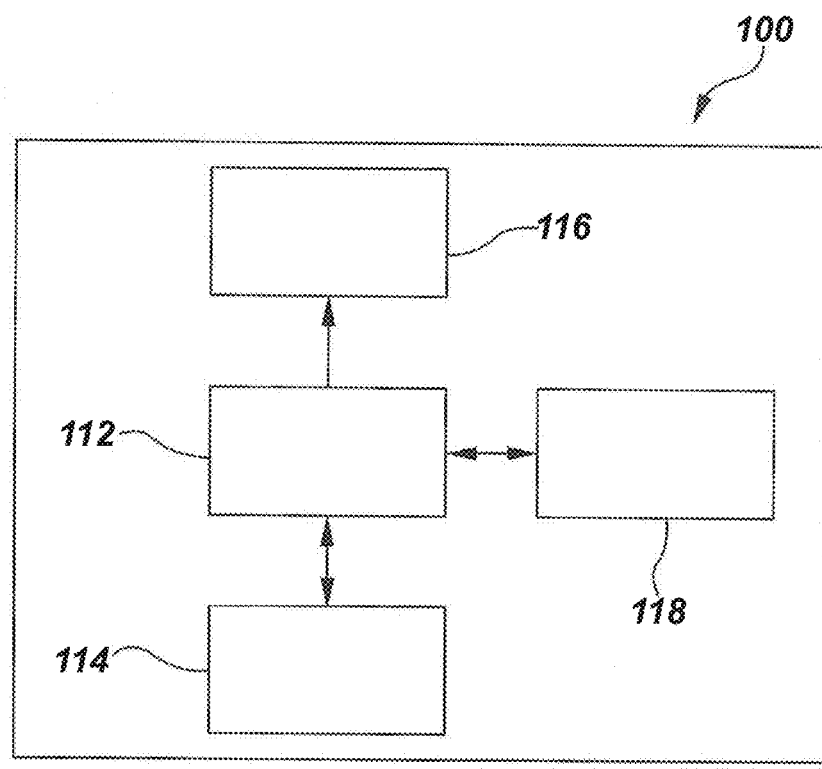
FIG. 9 is a simplified block diagram of various blocks of the hand-held test meter of FIG. 8.
Figure 10:
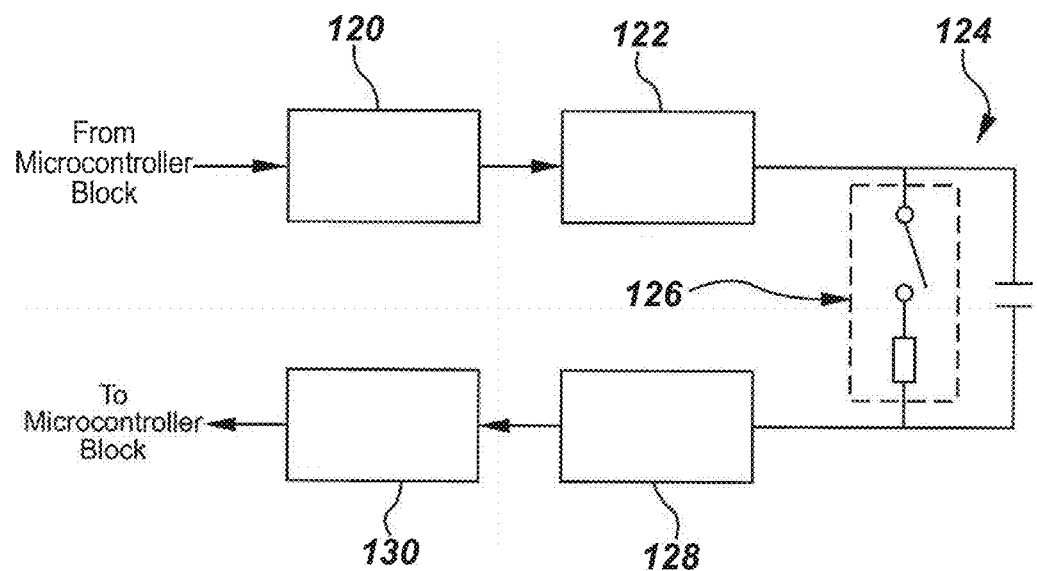
FIG. 10 is a simplified block diagram of a phase-shift-based hematocrit measurement block as can be employed in embodiments according to the present disclosure.
Figure 11:
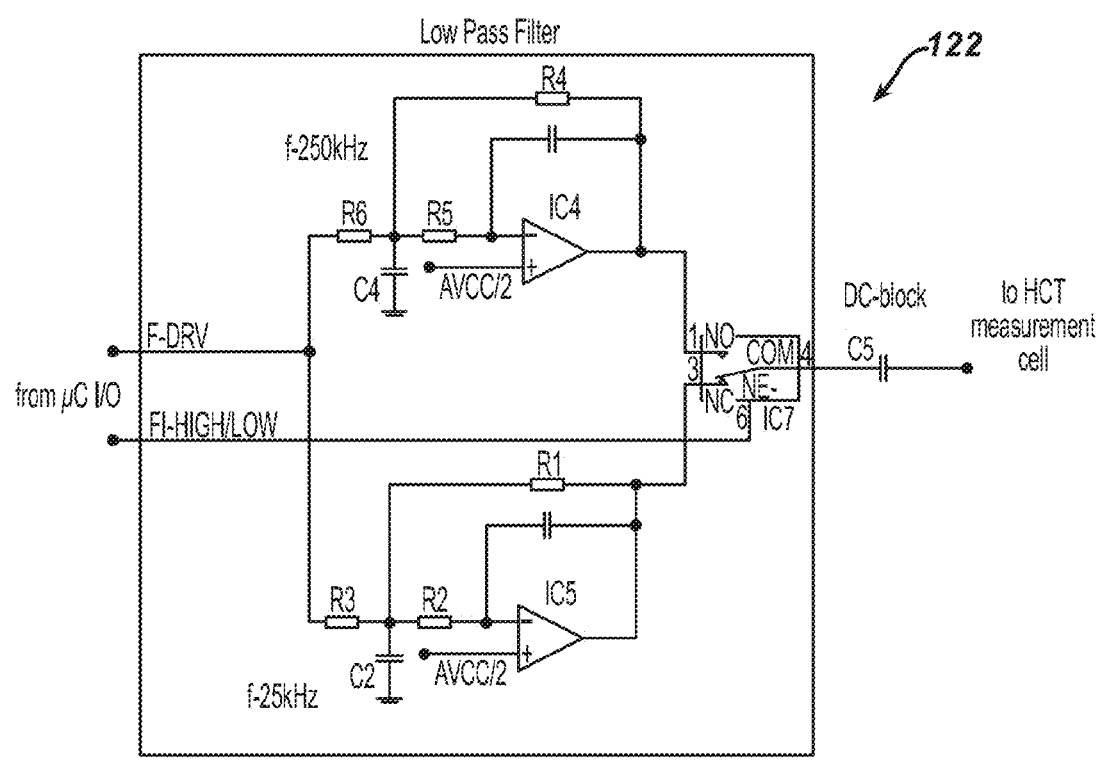
FIG. 11 is a simplified annotated schematic diagram of a dual low pass filter sub-block as can be employed in embodiments of the present disclosure.
Figure 12:
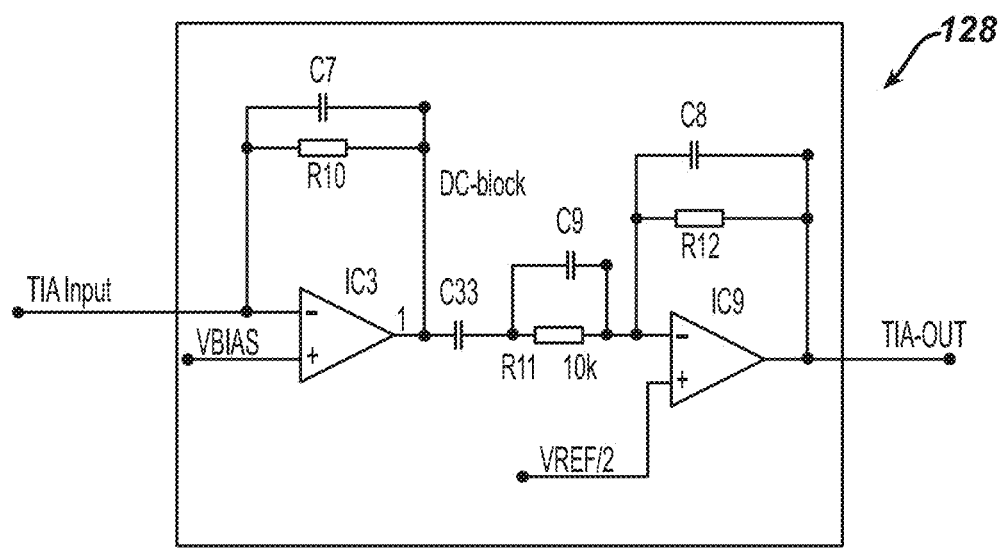
FIG. 12 is a simplified annotated schematic diagram of a transimpedance amplifier (TIA) sub-block as can be employed in embodiments of the present disclosure.
Figure 13:
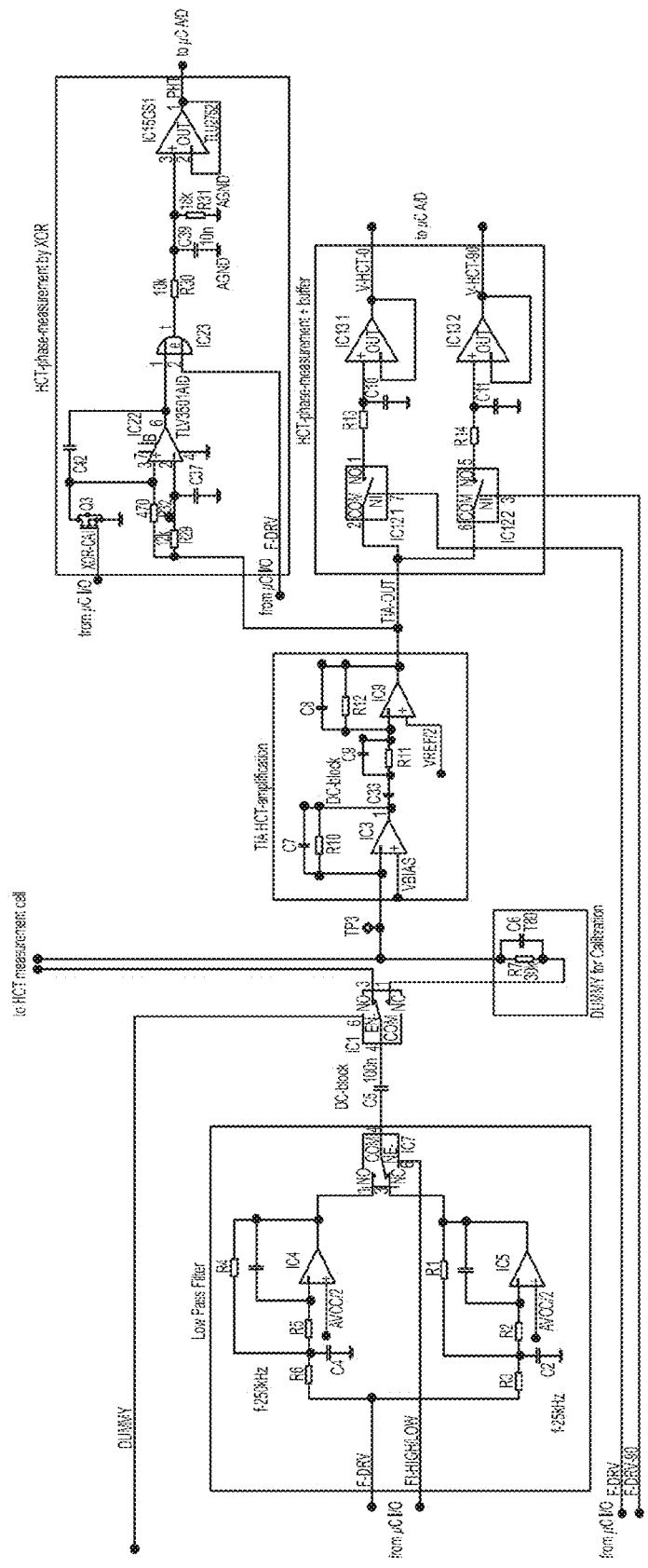
FIG. 13 is a simplified annotated schematic block diagram depicting a dual low pass filter sub-block, a calibration load sub-block, an analytical test strip sample cell interface sub-block, a transimpedance amplifier sub-block, an XOR phase shift measurement sub-block and a Quadratur DEMUX phase-shift measurement sub-block as can be employed in a phase-shift-based hematocrit measurement block of embodiments of the present disclosure.

FIG. 8 is a simplified depiction of a hand-held test meter 100 according to an embodiment of the present disclosure. FIG. 9 is a simplified block diagram of various blocks of hand-held test meter 100. FIG. 10 is a simplified combined block diagram of a phase-shift-based hematocrit measurement block of hand-held test meter 100. FIG. 11 is a simplified annotated schematic diagram of a dual low pass filter sub-block of hand-held test meter 100. FIG. 12 is a simplified annotated schematic diagram of a transimpedance amplifier sub-block of hand-held test meter 100. FIG. 13 is a simplified annotated schematic block diagram of portions of a phase-shift-based hematocrit measurement block of hand-held test meter 100.

Referring to FIGS. 8 through 13, hand-held test meter 100 includes a display 102, a plurality of user interface buttons 104, a strip port connector 106, a USB interface 108, and a housing 110 (see FIG. 8). Referring to FIG. 9 in particular, hand-held test meter 100 also includes a microcontroller block 112, a phase-shift-based hematocrit measurement block 114, a display control block 116, a memory block 118 and other electronic components (not shown) for applying a test voltage to analytical test strip (labeled TS in FIG. 8), and also for measuring an electrochemical response (e.g., plurality of test current values) and determining an analyte based on the electrochemical response. To simplify the current descriptions, the figures do not depict all such electronic circuitry.

Display 102 can be, for example, a liquid crystal display or a bi-stable display configured to show a screen image. An example of a screen image may include a glucose concentration, a date and time, an error message, and a user interface for instructing an end user how to perform a test.

Strip port connector 106 is configured to operatively interface with an analytical test strip TS, such as an electrochemical-based analytical test strip configured for the determination of glucose in a whole blood sample. Therefore, the analytical test strip is configured for operative insertion into strip port connector 106 and to operatively interface with phase-shift-based hematocrit measurement block 114 via, for example, suitable electrical contacts.

USB Interface 108 can be any suitable interface known to one skilled in the art. USB Interface 108 is essentially a passive component that is configured to power and provide a data line to hand-held test meter 100.

Once an analytical test strip is interfaced with hand-held test meter 100, or prior thereto, a bodily fluid sample (e.g., a whole blood sample) is introduced into a sample chamber of the analytical test strip. The analytical test strip can include enzymatic reagents that selectively and quantitatively transform an analyte into another predetermined chemical form. For example, the analytical test strip can include an enzymatic reagent with ferricyanide and glucose oxidase so that glucose can be physically transformed into an oxidized form.

Memory block 118 of hand-held test meter 100 includes a suitable algorithm and can be configured, along with microcontroller block 112 to determine an analyte based on the electrochemical response of analytical test strip and the hematocrit of the introduced sample. For example, in the determination of the analyte blood glucose, the hematocrit can be used to compensate for the effect of hematocrit on electrochemically determined blood glucose concentrations.

Microcontroller block 112 is disposed within housing 110 and can include any suitable microcontroller and/or microprocesser known to those of skill in the art. One such suitable microcontroller is a microcontroller commercially available from Texas Instruments, Dallas, Tex. USA and part number MSP430F5138. This microcontroller can generate a square wave of 25 to 250 kHz and a 90 degree phase-shifted wave of the same frequency and, thereby, function as a signal generation s-block described further below. MSP430F5138 also has Analog-to-Digital (A/D) processing capabilities suitable for measuring voltages generated by phase shift based hematocrit measurement blocks employed in embodiments of the present disclosure.

Referring in particular to FIG. 10, phase-shift-based hematocrit measurement block 114 includes a signal generation sub-block 120, a low pass filter sub-block 122, an analytical test strip sample cell interface sub-block 124, an optional calibration load block 126 (within the dashed lines of FIG. 10), a transimpedance amplifier sub-block 128, and a phase detector sub-block 130.

As described further below, phase-shift-based hematocrit measurement block 114 and microcontroller block 112 are configured to measure the phase shift of a bodily fluid sample in a sample cell of an analytical test strip inserted in the hand-held test meter by, for example, measuring the phase shift of one or more high frequency electrical signals driven through the bodily fluid sample. In addition, microcontroller block 112 is configured to compute the hematocrit of the bodily fluid based on the measured phase shift. Microcontroller 112 can compute the hematocrit by, for example, employing an A/D converter to measure voltages received from a phase-detector sub-block, convert the voltages into a phase-shift and then employing a suitable algorithm or look-up table to convert the phase-shift into a hematocrit value. Once apprised of the present disclosure, one skilled in the art will recognize that such an algorithm and/or look-up table will be configured to take into account various factors such as strip geometry (including electrode area and sample chamber volume) and signal frequency.

It has been determined that a relationship exists between the reactance of a whole blood sample and the hematocrit of that sample. Electrical modeling of a bodily fluid sample (i.e., a whole blood sample) as parallel capacitive and resistive components indicates that when an alternating current (AC) signal is forced through the bodily fluid sample, the phase shift of the AC signal will be dependent on both the frequency of the AC voltage and the hematocrit of the sample. Moreover, modeling indicates that hematocrit has a relatively minor effect on the phase shift when the frequency of the signal is in the range of approximately 10 kHz to 25 kHz and a maximum effect on the phase shift when the frequency of the signal is in the range of approximately 250 kHz to 500 KHz. Therefore, the hematocrit of a bodily fluid sample can be measured by, for example, driving AC signals of known frequency through the bodily fluid sample and detecting their phase shift. For example, the phase-shift of a signal with a frequency in the range of 10 kHz to 25 kHz can be used as a reference reading in such a hematocrit measurement while the phase shift of a signal with a frequency in the range of 250 kHz to 500 kHz can be used as the primary measurement.

Referring to FIGS. 10 through 13 in particular, signal generation sub-block 120 can be any suitable signal generation block and is configured to generate a square wave (0V to Vref) of a desired frequency. Such a signal generation sub-block can, if desired, be integrated into microcontroller block 112.

The signal generated by signal generation sub-block 120 is communicated to dual low pass filter sub-block 122, which is configured to convert the square wave signal to a sine wave signal of a predetermined frequency. The dual LPF of FIG. 11 is configured to provide both a signal of a first frequency (such as a frequency in the range of 10 kHz to 25 kHz) and a signal of a second frequency (such as a frequency in the range of 250 kHz to 500 kHz) to the analytical test strip sample cell interface sub-block and an analytical test strips' sample chamber (also referred to as the HCT measurement cell). Selection of the first and second frequency is accomplished using switch IC7 of FIG. 11. The dual LPF of FIG. 11 includes employs two suitable operational amplifiers (IC4 and IC5) such as the operational amplifier available from Texas Instruments, Dallas, Tex., USA as high-speed, voltage feedback, CMOS operational amplifier part number OPA354.

Referring to FIG. 11, F-DRV represents a square wave input of either a low or high frequency (e.g., 25 kHz or 250 kHz) and is connected to both IC4 and IC5. Signal Fi-HIGH/LOW (from the microcontroller) selects the output of dual low pass filter sub-block 122 via switch IC7. C5 in FIG. 11 is configured to block the operating voltage of dual low pass filter sub-block 122 from the HCT measurement cell.

Although a specific dual LPF is depicted in FIG. 11, dual low pass filter sub-block 122 can be any suitable low pass filter sub-block known to one skilled in the art including, for example, any suitable multiple feedback low pass filter, or a Sallen and Key low pass filter.

The sine wave produced by low pass filter sub-block 122 is communicated to analytical test strip sample cell interface sub-block 124 where it is driven across the sample cell of the analytical test strip (also referred to as an HCT measurement cell). Analytical test strip sample cell interface block 124 can be any suitable sample cell interface block including, for example, an interface block configured to operatively interface with the sample cell of the analytical test strip via first electrode and second electrodes of the analytical test strip disposed in the sample cell. In such a configuration, the signal can be driven into the sample cell (from the low pass filter sub-block) via the first electrode and picked-up from the sample cell (by the transimpedance amplifier sub-block) via the second electrode as depicted in FIG. 13.

The current produced by driving the signal across the sample cell is picked-up by transimpedance amplifier sub-block 128 and converted into a voltage signal for communication to phase detector sub-block 130.

Transimpedance sub-block 128 can be any suitable transimpedance sub-block known to one skilled in the art. FIG. 12 is a simplified annotated schematic block diagram of one such transimpedance amplifier sub-block (based on two OPA354 operational amplifiers, IC3 and IC9). The first stage of TIA sub-block 128 operates at, for example, 400 mV, which limits the AC amplitude to +/−400 mV. The second stage of TIA sub-block 128 operates at Vref/2, a configuration which enables the generation of an output of the full span of the microcontroller A/D inputs. C9 of TIA sub-block 128 serves as a blocking component that only allows an AC sine wave signal to pass.

Phase detector sub-block 130 can be any suitable phase detector sub-block that produces either a digital frequency that can be read back by microcontroller block 112 using a capture function, or an analog voltage that can be read back by microcontroller block 112 using an analog to digital converter. FIG. 13 depicts a schematic that includes two such phase detector sub-blocks, namely an XOR phase detector (in the upper half of FIG. 13 and including IC22 and IC23) and a Quadrature DEMUX phase detector (in the lower half of FIG. 13 and including IC12 and IC13).

FIG. 13 also depicts a calibration load sub-block 126 that includes a switch (IC16) and a dummy load R7 and C6. Calibration load sub-block 126 is configured for the dynamic measurement of a phase offset for the known phase shift of zero degrees produced by resistor R7, thus providing a phase offset for use in calibration. C6 is configured to force a predetermined slight phase shift, e.g. to compensate for phase delays caused by parasitic capacities in the signal traces to the sample cell, or for phase delays in the electrical circuits (LPF and TIA).

The Quadrature DEMUX phase detector circuit of FIG. 13 includes two portions, one portion for a resistive part of the incoming AC signal and one portion for the reactive portion of the incoming AC signal. Use of such two portions enables the simultaneous measurement of both the resistive and reactive portion of the AC signal and a measurement range that covers 0 degrees to 360 degrees. The Quadrature DEMUX circuit of FIG. 13 generates two separate output voltages. One of these output voltages represents the "in phase measurement" and is proportional to the "resistive" part of the AC signal, the other output voltage represents the "Quadrature Measurement" and is proportional to the "reactive part of the signal. The phase shift is calculated as:

$$\Phi = \tan^{-1}(V_{QUAD\text{-}PHASE}/V_{IN\text{-}PHASE})$$

Such a Quadrature DEMUX phase detector circuit can also be employed to measure the impedance of a bodily fluid sample in the sample cell. It is hypothesized, without being bound, that the impedance could be employed along with the phase-shift, or independently thereof, to determine the hematocrit of the bodily sample. The amplitude of a signal forced through the sample cell can be calculated using the two voltage outputs of the Quadrature DEMUX circuit as follows:

$$\text{Amplitude} = \text{SQR}((V_{QUAD\text{-}PHASE}) + (V_{IN\text{-}PHASE}))$$

This amplitude can then be compared to an amplitude measured for the known resistor of calibration load block 126 to determine the impedance.

The XOR phase detector portion has a measurement range of 0° to 180°, or alternatively a measurement range of −90° to +90°, depending whether the "Square wave input from µC" is in phase to the sine wave or is set to a 90° phase shift. The XOR phase detector produces an output frequency that is always double the input frequency, however the duty cycle varies. If both inputs are perfectly in phase, the output is LOW, if both inputs are 180° shifted the output is always HIGH. By integrating the output signal (e.g. via a simple RC element) a voltage can be generated that is directly proportional to the phase shift between both inputs.

Once apprised of the present disclosure, one skilled in the art will recognize that phase detector sub-blocks employed in embodiments of the present disclosure can take any suitable form and include, for example, forms that employ rising edge capture techniques, dual edge capture techniques, XOR techniques and synchronous demodulation techniques.

Since low pass filter sub-block 122, transimpedance amplifier sub-block 128 and phase detector sub-block 130 can introduce a residual phase shift into phase-shift-based hematocrit measurement block 114, calibration load block 126 can be optionally included in the phase-shift-based hematocrit measurement block. Calibration load block 126 is configured to be essentially resistive in nature (for example a 33 k-ohm load) and, therefore, induces no phase shift between excitation voltage and generated current. Calibration load block 126 is configured to be switched in across the circuit to give a "zero" calibration reading. Once calibrated, the hand-held test meter can measure the phase shift of a bodily fluid sample, subtract the "zero" reading to compute a corrected phase shift and subsequently compute the bodily sample hematocrit based on the corrected phase shift.

Figure 14:
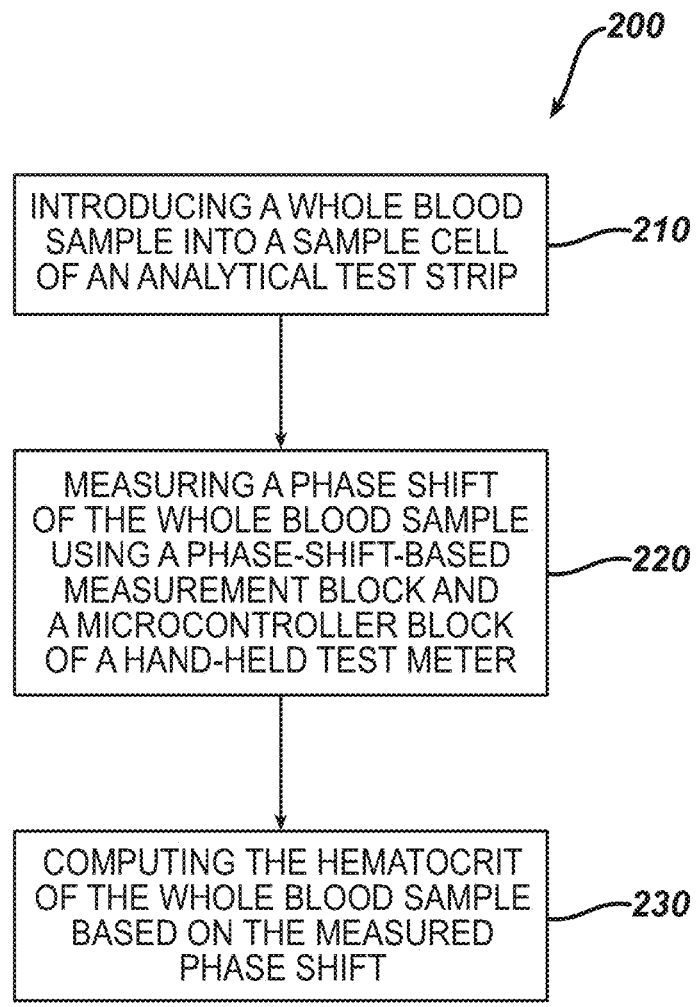
FIG. 14 is a flow diagram depicting stages in a method for employing a hand-held test meter according to an embodiment of the present disclosure.

FIG. 14 is a flow diagram depicting stages in a method 200 for employing a hand-held test meter and analytical test strip (e.g., an electrochemical-based analytical test strip). Method 200, at step 210, includes introducing a whole blood sample into a sample cell of the analytical test strip.

At step 220, a phase shift of the whole blood sample in the sample cell is measured using a phase-shift-based measurement block and a microcontroller block of a hand-held test meter. Method 200 further includes computing the hematocrit of whole blood sample based on the measured phase shift using the microcontroller block (see step 230 of FIG. 14).

Moreover, while the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

The invention claimed is:

1. A method of demonstrating increased accuracy of a test strip, the method comprising:
    providing a batch of test strips;
    introducing a referential sample containing a referential concentration of an analyte to each test strip of the batch of test strips to initiate a test sequence;
    reacting the analyte with a reagent on each test strip to cause a physical transformation of the analyte;
    determining a physical characteristic of the referential sample;
    deriving a defined batch slope for the batch of test strips based on the determined physical characteristics of the referential sample for selected test strips from the batch of test strips;
    determining an approximate analyte concentration of the referential analyte concentration as being in one of a low glucose range, a medium glucose range or a high glucose range;
    determining a sampling time point based on the approximate analyte concentration of the referential analyte concentration, the determined sampling time point being selected as a first sampling time point responsive to the approximate analyte concentration being in the low glucose range, a second sampling time point responsive to the approximate analyte concentration being in the medium glucose range, and a third sampling time point responsive to the approximate analyte concentration being in the high glucose range;
    sampling an electrical output of the referential sample at the determined sampling time point during the test sequence;
    calculating an analyte concentration based on the defined batch slope, the determined sampling time point and sampled electrical output to provide for a final analyte concentration value for each test strip of the batch of test strips such that at least 95% of the final analyte concentration values of the batch of test strips are within ±15% of the referential analyte concentration.

2. The method of claim 1, in which the determining comprises applying a first signal to the sample to measure the physical characteristic of the sample.

3. The method of claim 2, in which the sampling comprises driving a second signal to the sample.

4. The method of claim 3, in which the applying of the first signal and the driving of the second signal is in sequential order.

5. The method of claim 3, in which the applying of the first signal overlaps with the driving of the second signal.

6. The method of claim 2, in which the applying of the first signal comprises directing an optical signal to the sample so that a physical characteristic of the sample is determined from an output of the optical signal.

7. The method of claim 2, in which the applying of the first signal comprises directing an alternating signal to the sample so that a physical characteristic of the sample is determined from an output of the alternating signal.

8. The method of claim 2, in which the applying of the first signal comprises driving first and second alternating signals at different respective frequencies in which a first frequency is lower than the second frequency.

9. The method of claim 8, in which the first frequency is at least one order of magnitude lower than the second frequency.

10. The method of claim 8, in which the first frequency comprises any frequency in the range of about 10 kHz to about 250 kHz.

11. The method of claim 1, in which the physical characteristic comprises at least one of viscosity, hematocrit, temperature, and density of the sample, or combinations thereof.

12. The method of claim 1, in which the physical characteristic comprises hematocrit and the analyte comprises glucose.

13. The method of claim 1, in which the deriving comprises calculating a batch slope from an equation of the form:

$$x = aH^2 + bH + c$$

where
    x represents a derived batch slope from the deriving step;
    H represents the measured, determined or estimated physical characteristic of the sample;
    a represents about 1.4e−6,
    b represents about −3.8e−4,
    c represents about 3.6e−2.

14. The method of claim 13, in which the calculating of the analyte concentration comprises utilizing an equation of the form:

$$G_0 = \left[ \frac{I_E - \text{Intercept}}{x} \right]$$

where
    $G_0$ represents an analyte concentration
    $I_E$ represents, or is, a signal (value or measurement; proportional to analyte concentration) measured at a predetermined or specified sampling time;
    Intercept represents a calibration parameter for a batch of biosensors;
    x represents a derived batch slope from the deriving step.

15. The method of claim 14, in which the predetermined time is about 2.5 seconds after a start of the test sequence.

* * * * *